(12) United States Patent
Van Zuylen

(10) Patent No.: US 8,083,784 B2
(45) Date of Patent: Dec. 27, 2011

(54) PHOTON THERAPY METHOD AND APPARATUS

(75) Inventor: Jeffrey Van Zuylen, Mississauga (CA)

(73) Assignee: Photonx Health Corporation, Mississauga (CA)

( * ) Notice: Subject to any disclaimer, the term of this patent is extended or adjusted under 35 U.S.C. 154(b) by 1953 days.

(21) Appl. No.: 10/921,322

(22) Filed: Aug. 19, 2004

(65) Prior Publication Data

US 2005/0085875 A1    Apr. 21, 2005

Related U.S. Application Data

(60) Provisional application No. 60/495,883, filed on Aug. 19, 2003.

(51) Int. Cl.
*A61N 5/06* (2006.01)
(52) U.S. Cl. ............................................. 607/88; 607/90
(58) Field of Classification Search ............... 607/88–95; 606/8–12; 128/898
See application file for complete search history.

(56) References Cited

U.S. PATENT DOCUMENTS

| | | | | |
|---|---|---|---|---|
| 4,469,102 A | * | 9/1984 | Fish | 607/91 |
| 4,984,571 A | * | 1/1991 | Springer et al. | 607/94 |
| 5,067,049 A | * | 11/1991 | Milaire | 362/18 |
| 5,843,143 A | * | 12/1998 | Whitehurst | 607/88 |
| 6,196,010 B1 | * | 3/2001 | Mohrman | 62/184 |
| 6,663,659 B2 | * | 12/2003 | McDaniel | 607/88 |
| 7,198,634 B2 | * | 4/2007 | Harth et al. | 607/90 |
| 2001/0023363 A1 | * | 9/2001 | Harth et al. | 607/90 |

* cited by examiner

*Primary Examiner* — Ahmed Farah
(74) *Attorney, Agent, or Firm* — Bereskin & Parr LLP/S.E.N.C.R.L., s.r.l.

(57) ABSTRACT

A system and method of administering photon therapy to a treatment site of a patient are described. The system includes a plurality of treatment modules, each treatment module including a photon emitter, and a case for housing the photon emitter. The case includes linkers for linking each of the treatment modules to form an arbitrary modular pattern to cover the treatment site.

32 Claims, 43 Drawing Sheets

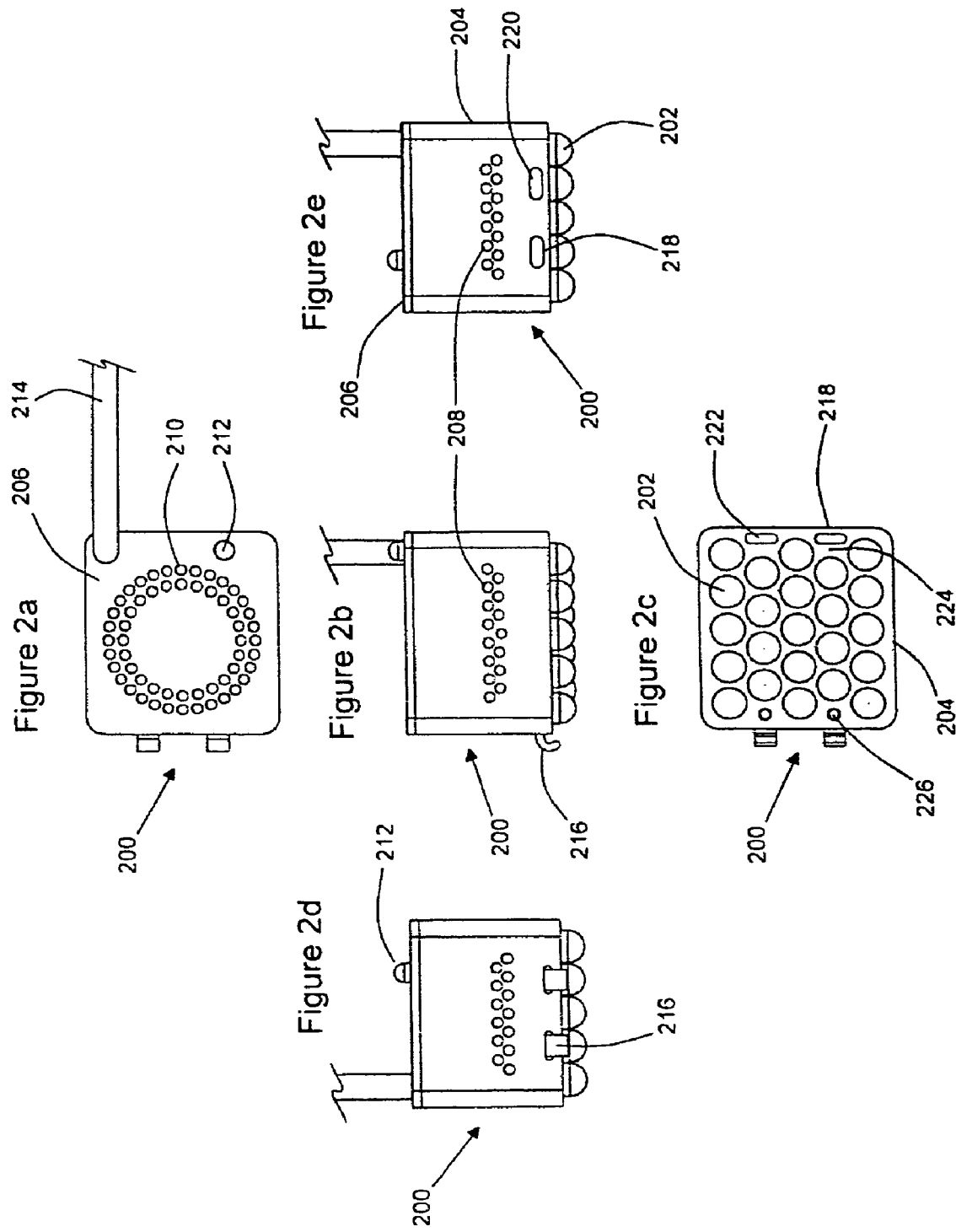

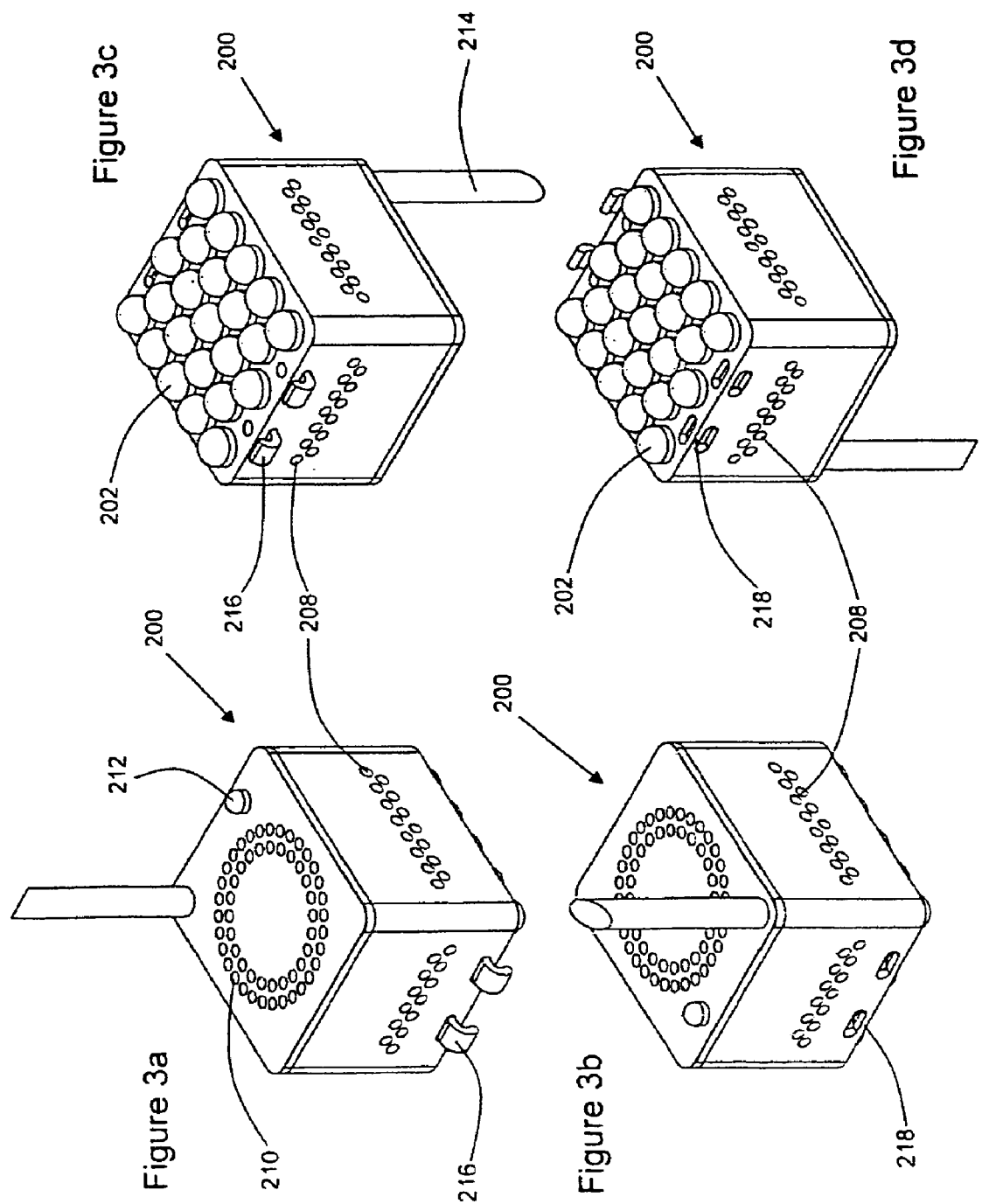

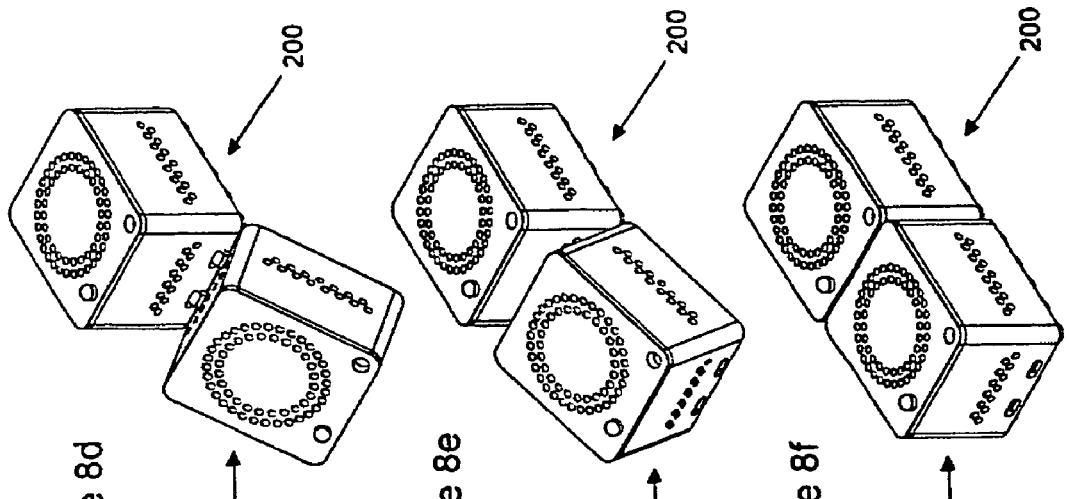
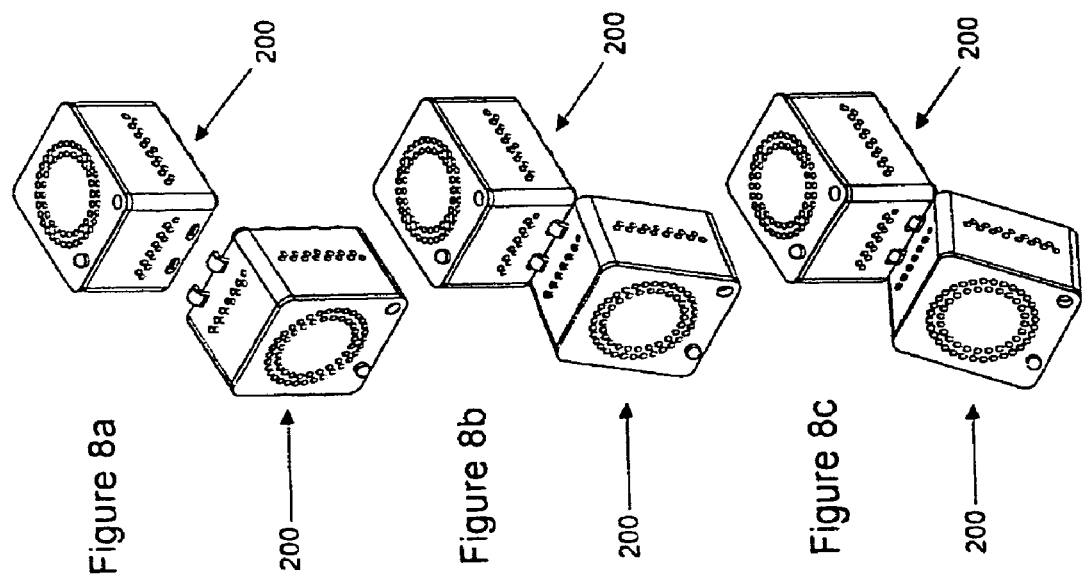

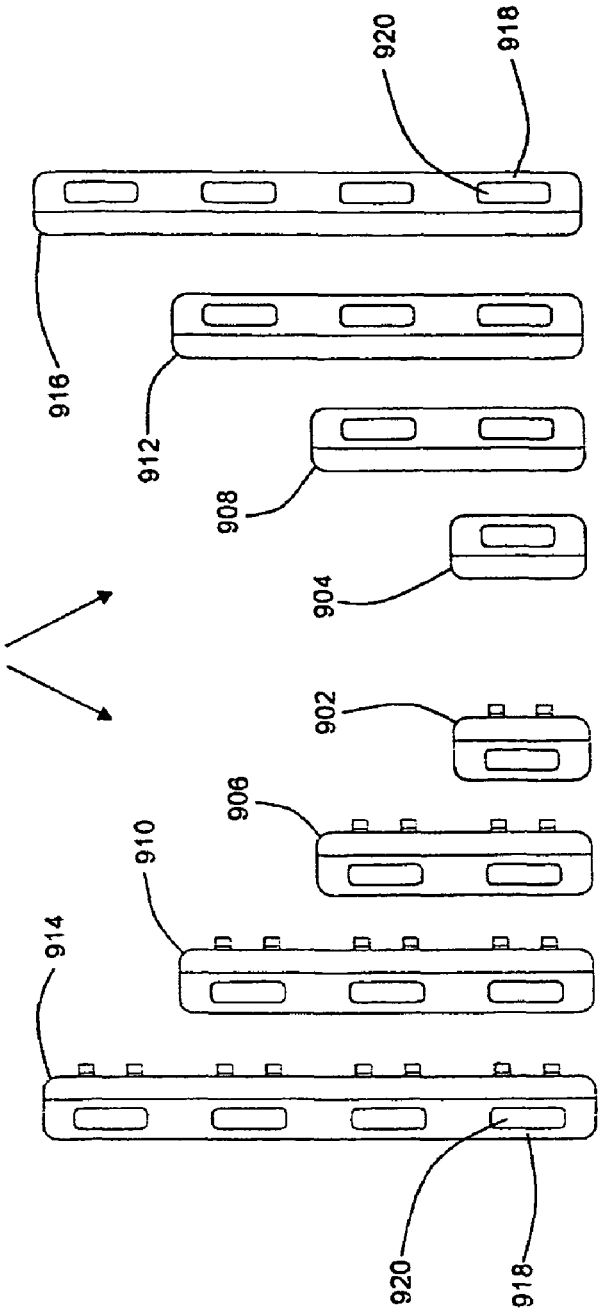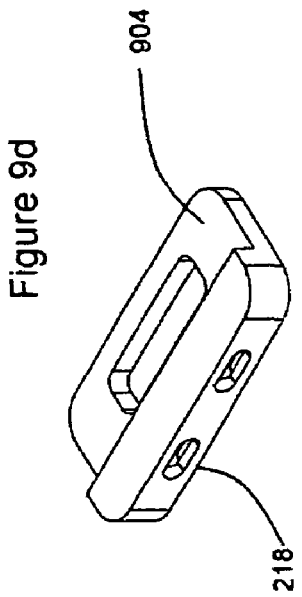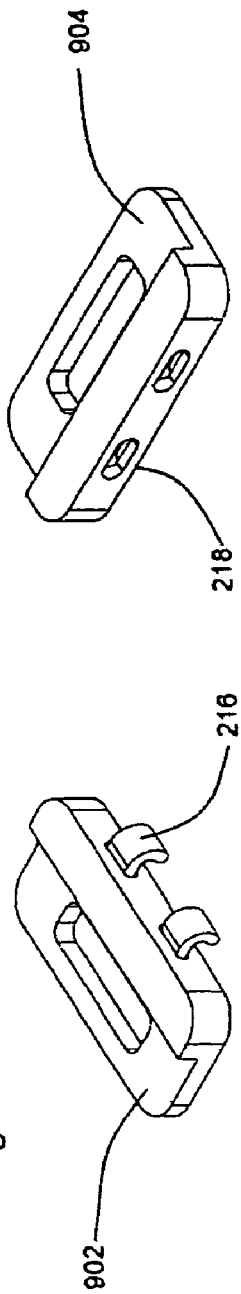

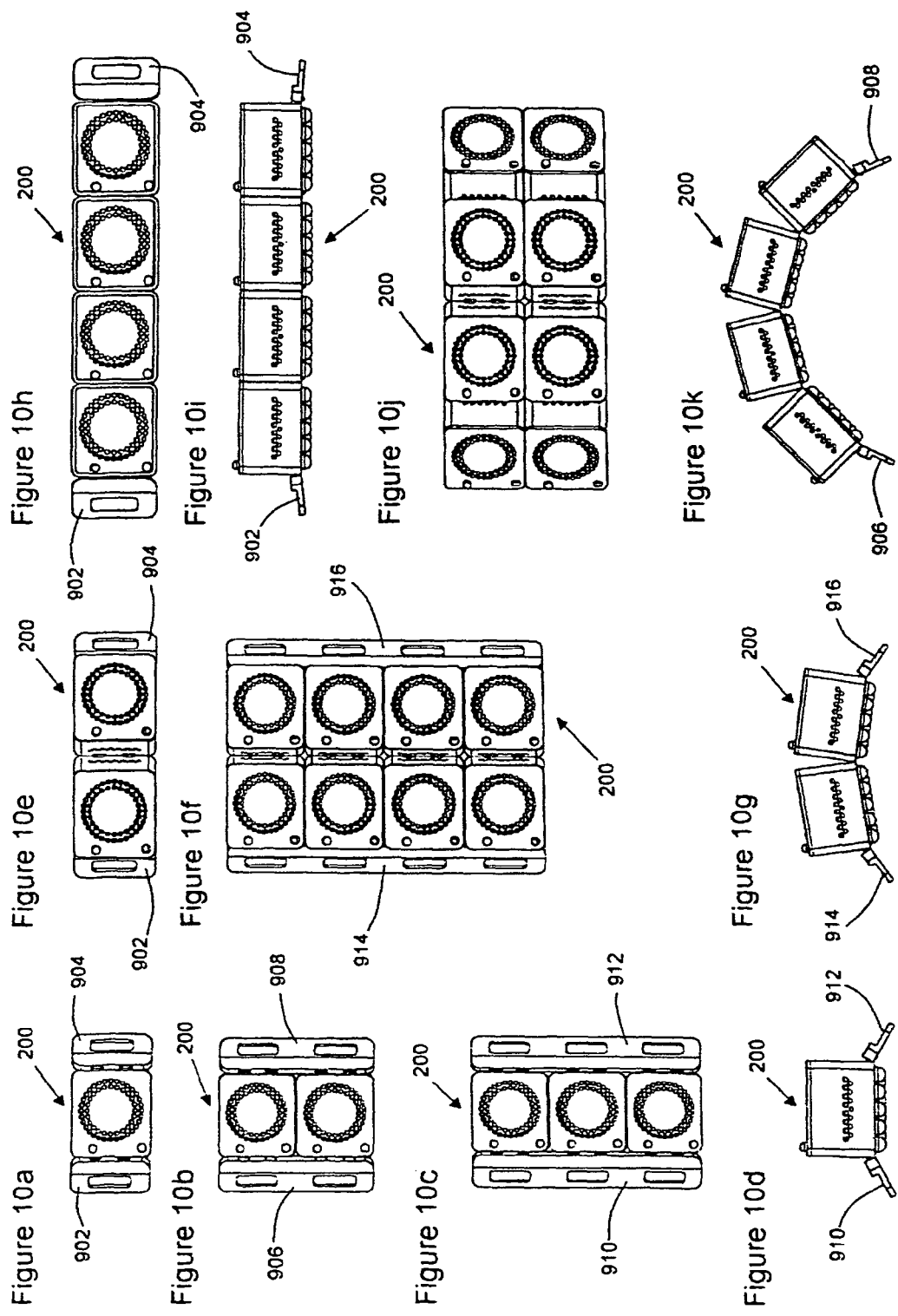

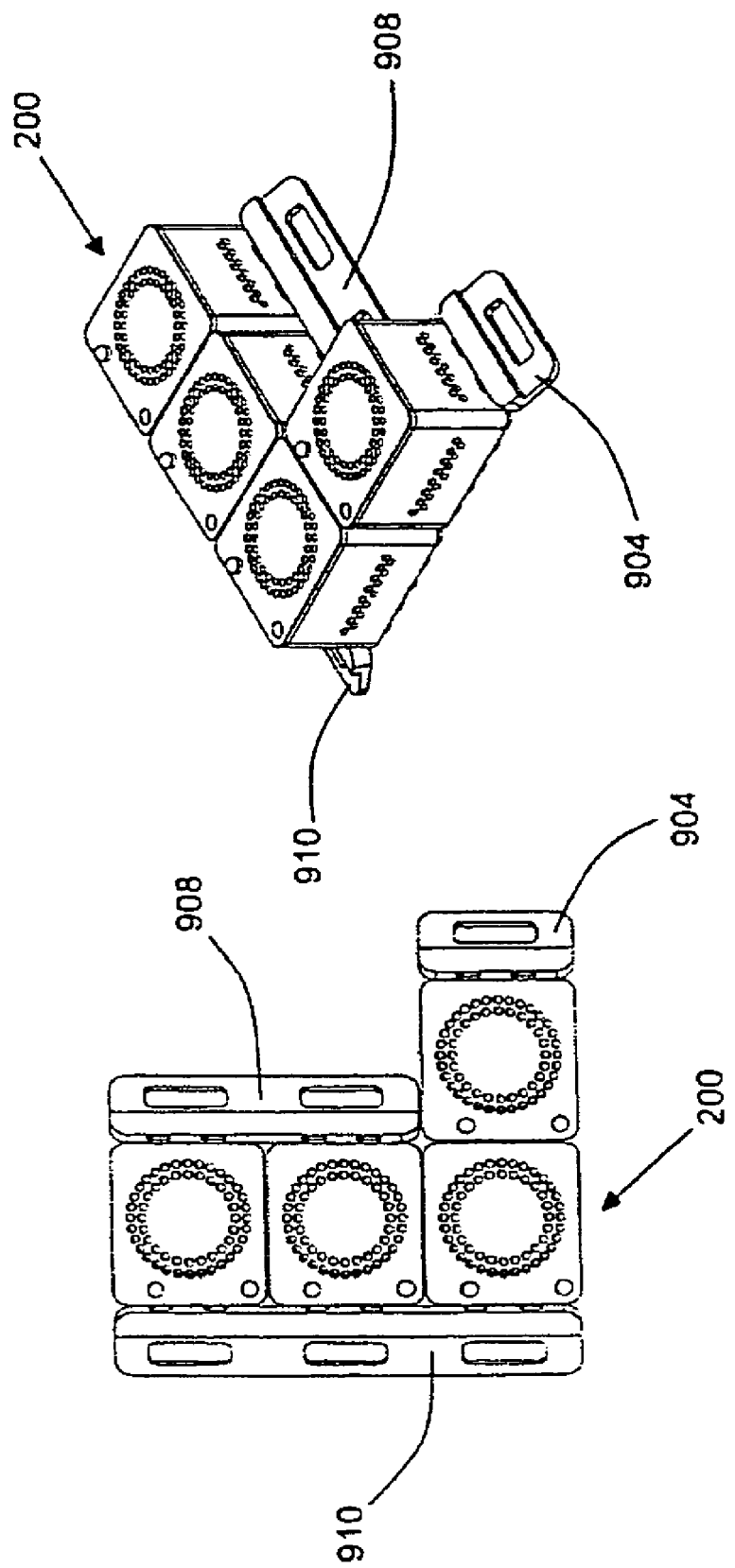

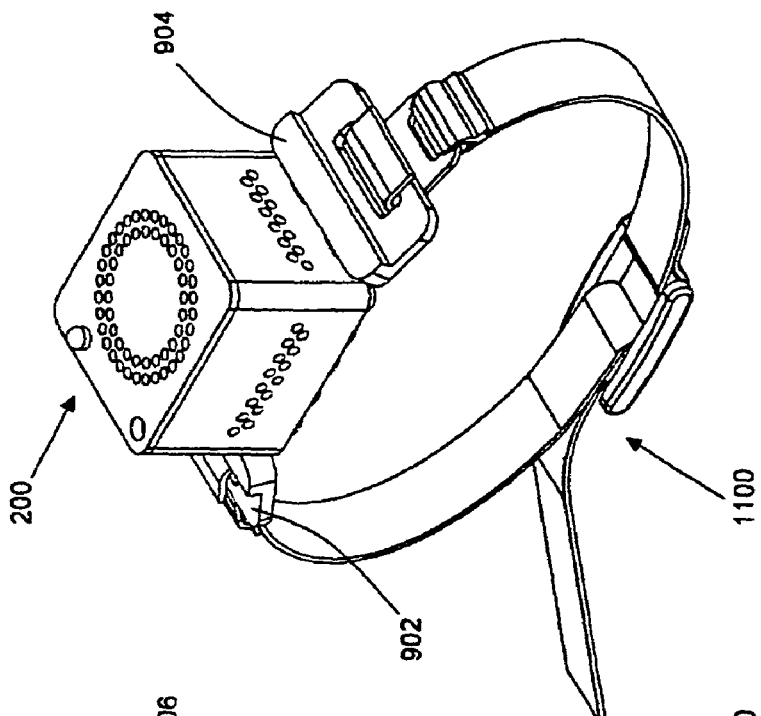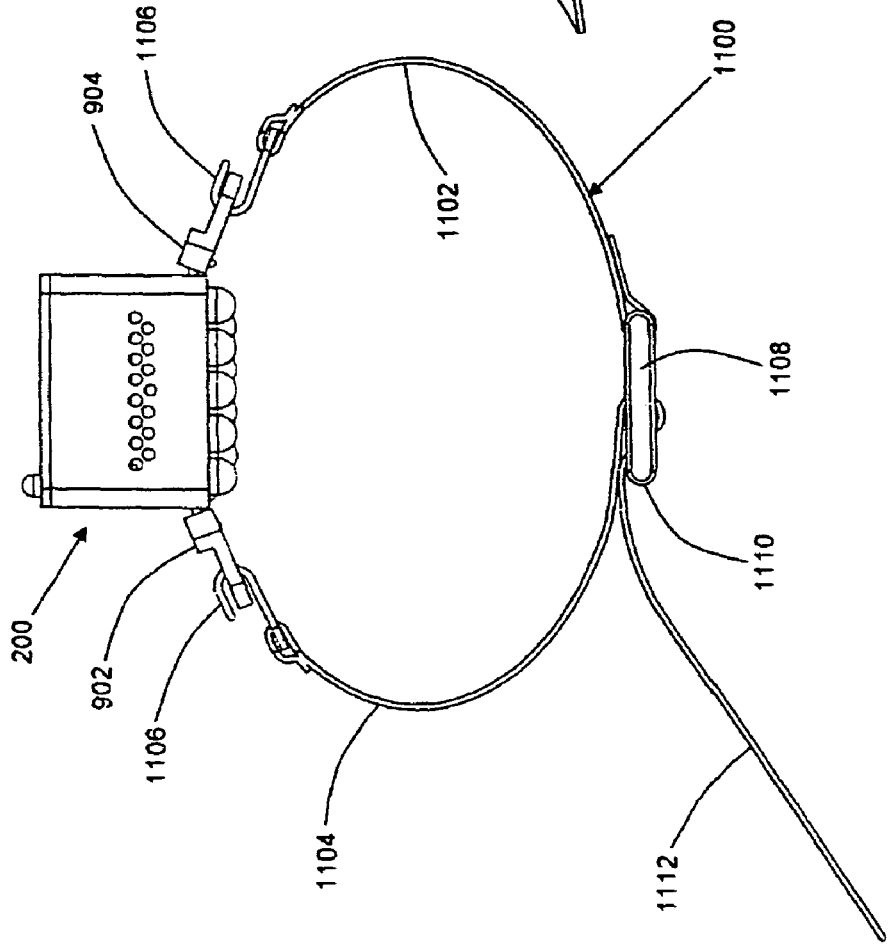

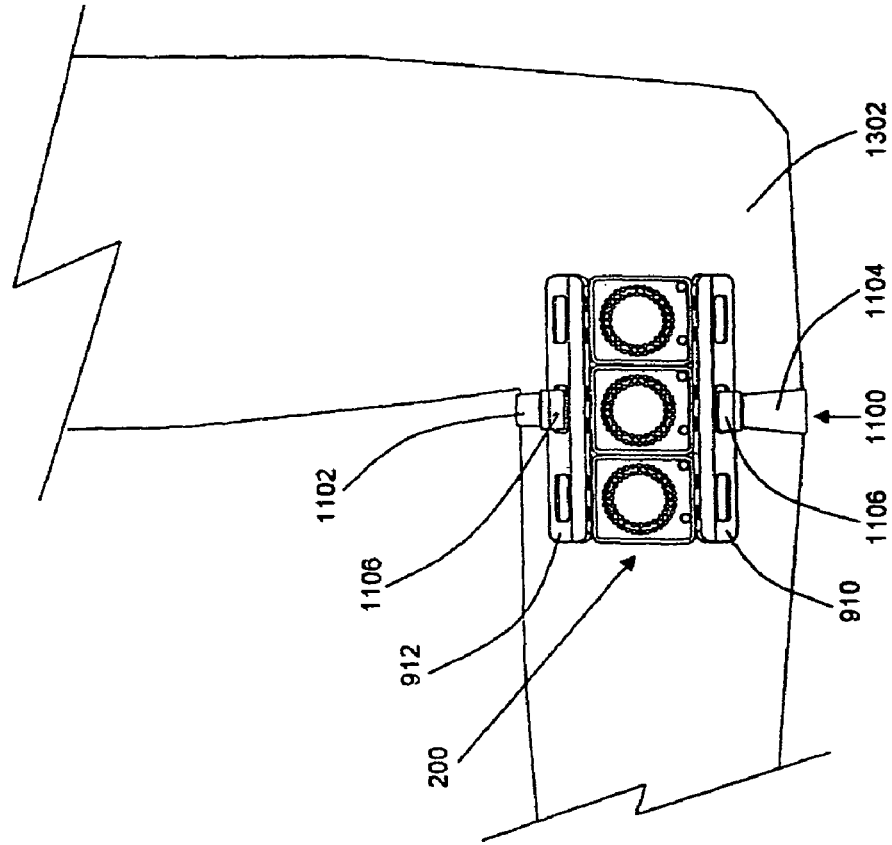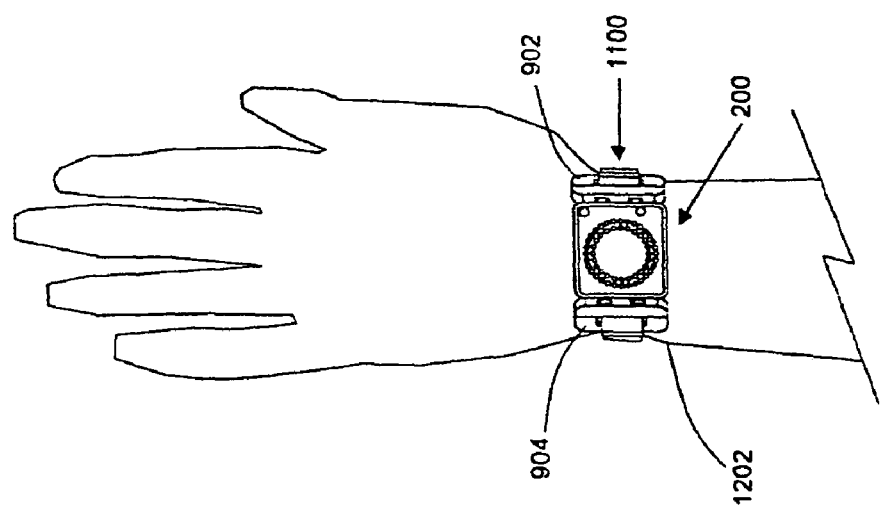

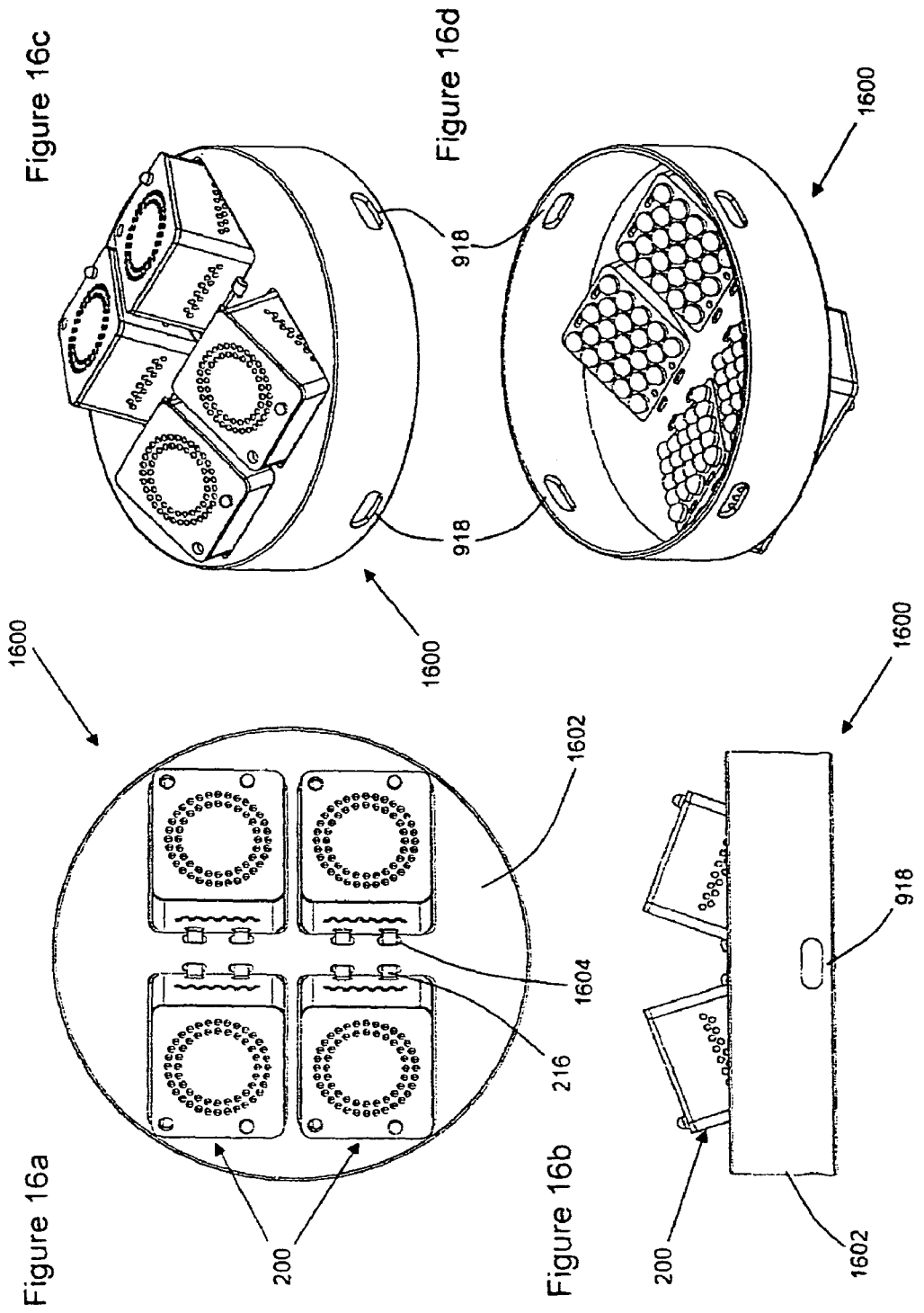

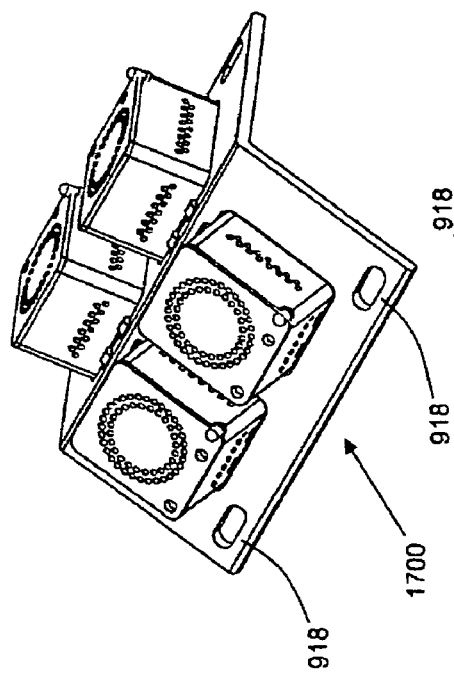
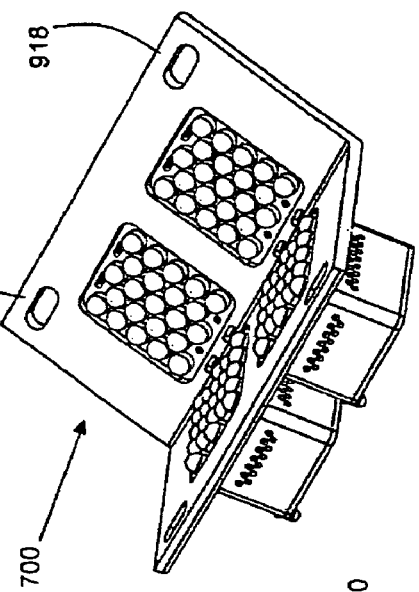
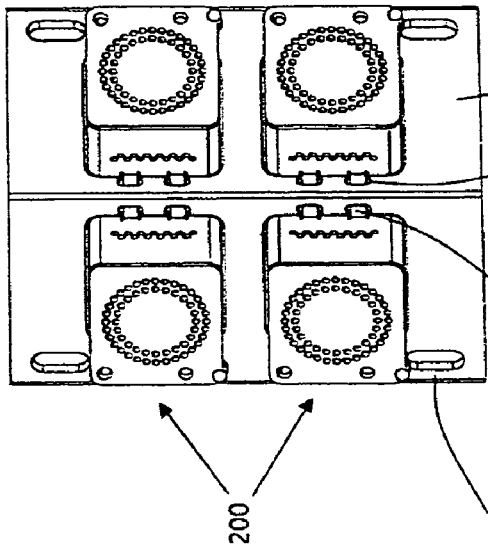
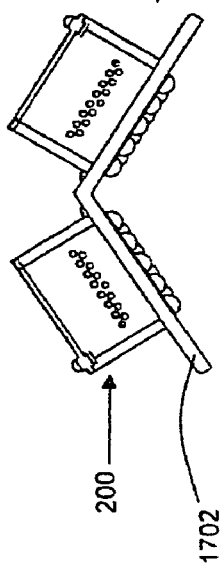
Figure 17a
Figure 17b
Figure 17c
Figure 17d

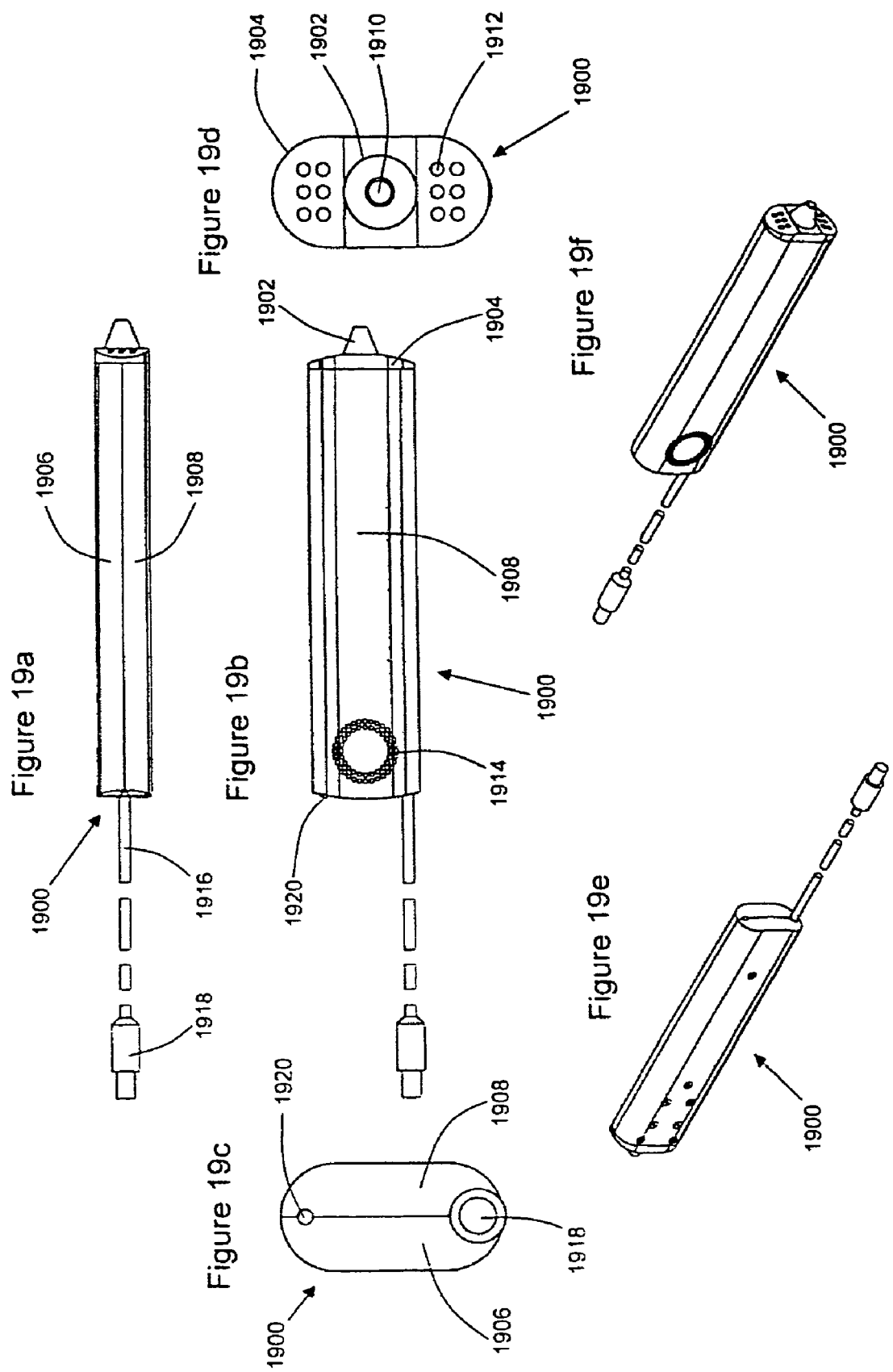

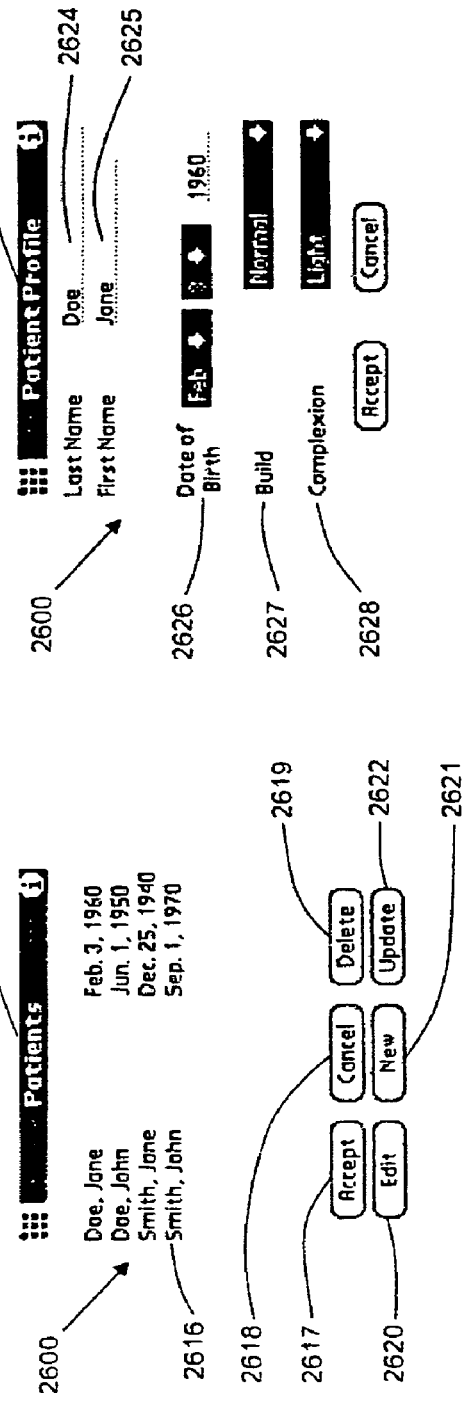
Figure 26f
Figure 26e
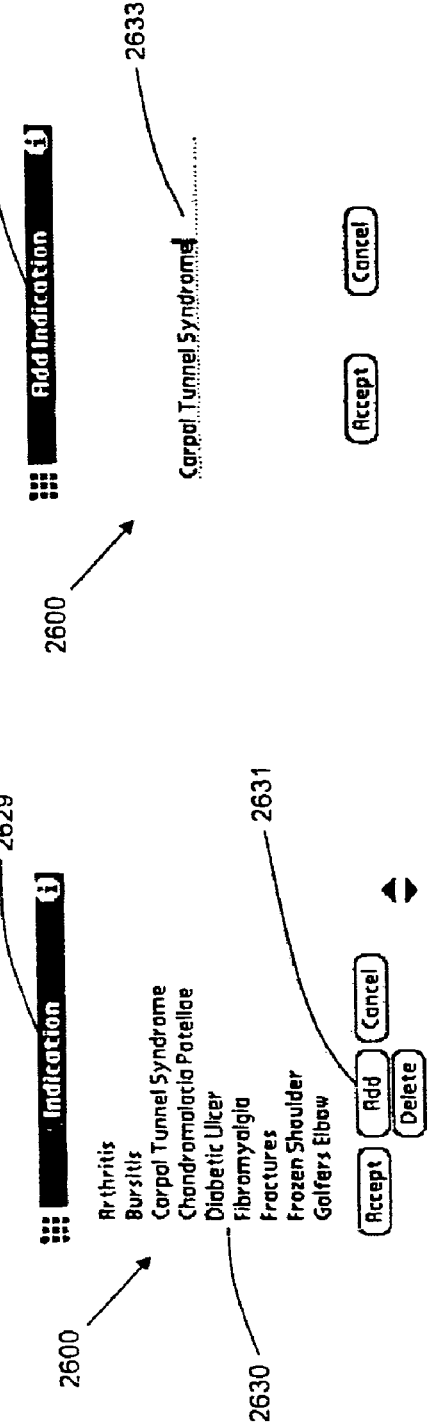
Figure 26h
Figure 26g

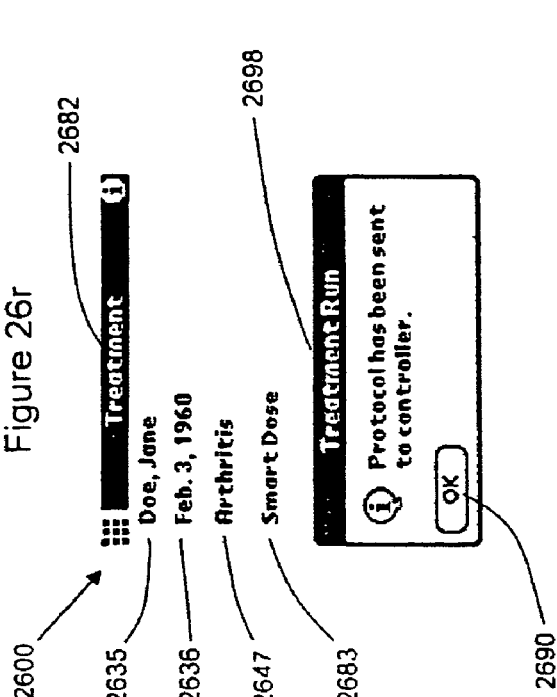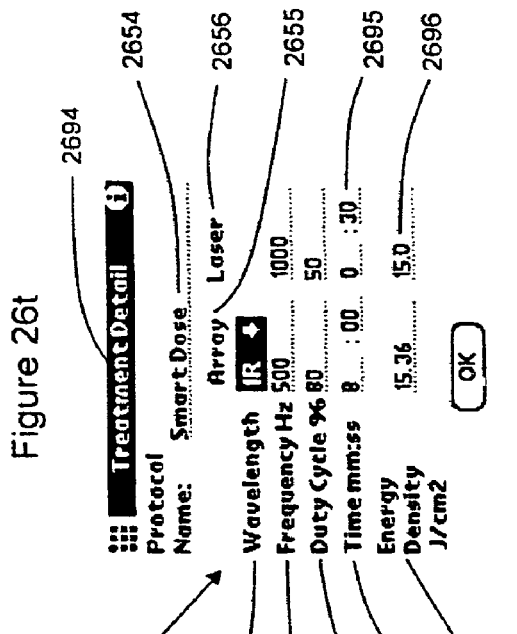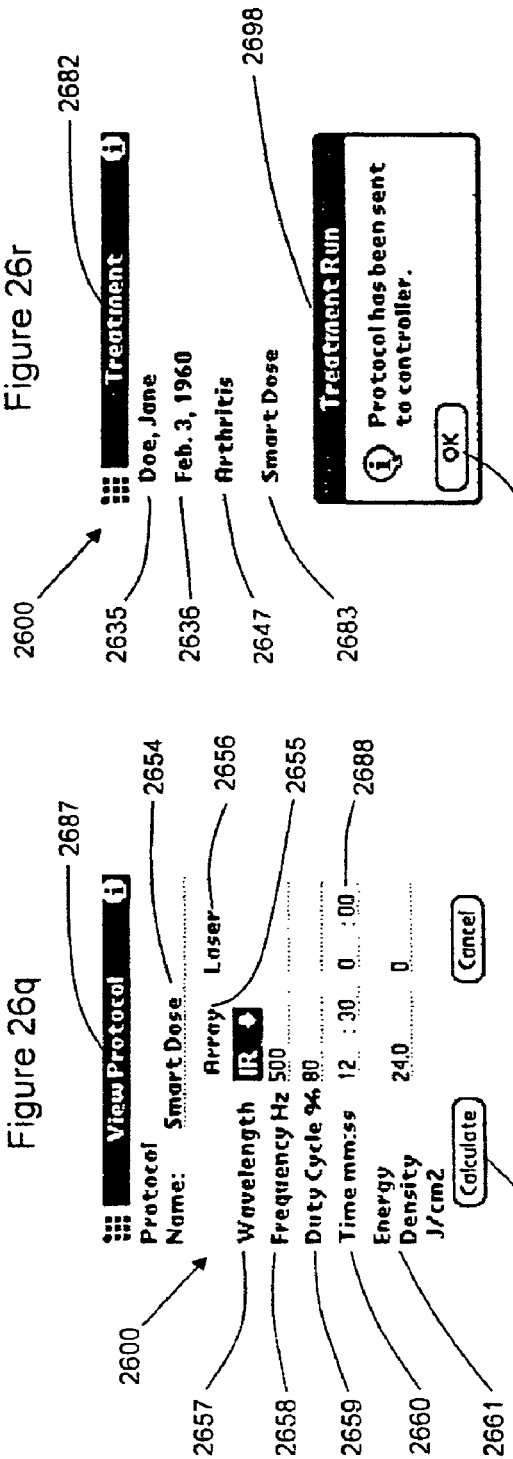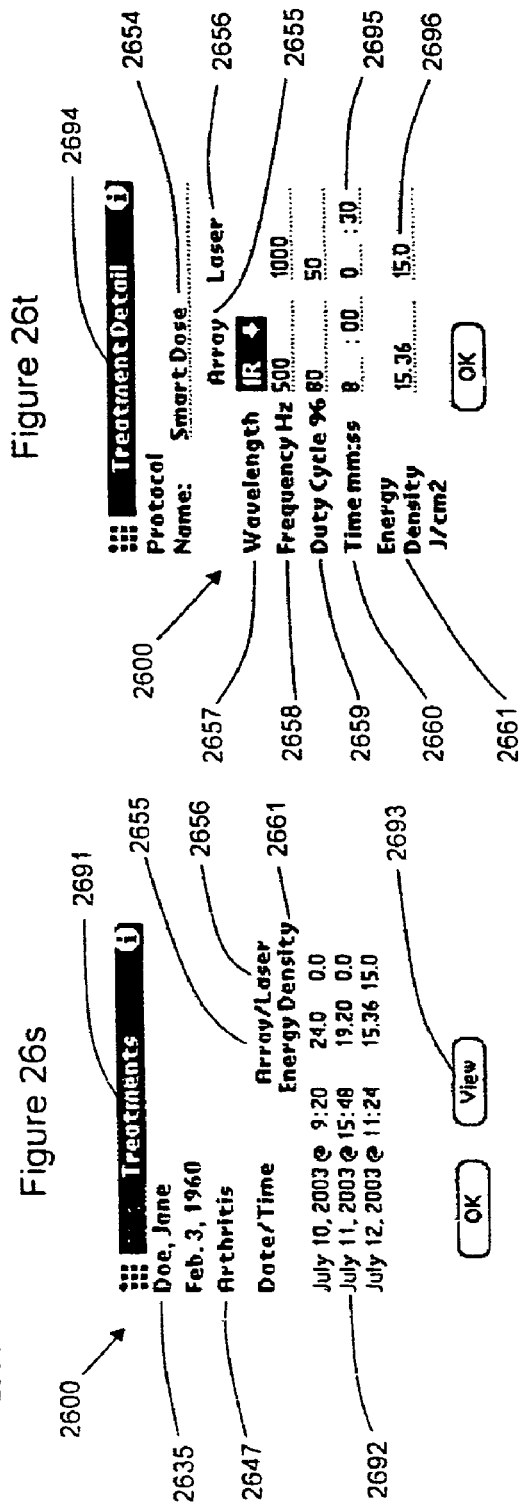

Figure 28b

Ailment Specific Parameters

Type: Musculoskeletal

| Group | Subgroup | Array | | | Laser | | |
|---|---|---|---|---|---|---|---|
| | | Freq | DC | Time | Freq | DC | Time |
| Chronicity | Acute | 1 | 0 | - | - | 0 | - |
| Chronicity | Subacute | - | +10 | - | - | +10 | - |
| Chronicity | Chronic | - | +20 | - | - | +20 | - |
| Target | Superficial | 1 | 0 | - | - | 0 | - |
| Target | Medium | 2 | 0 | 1.1 | 2 | 0 | 1.1 |
| Target | Deep | 3 | 0 | 1.3 | 3 | 0 | 1.3 |

Recovery Specific Parameters

Type: Musculoskeletal

| Group | Subgroup | Array | | | Laser | | |
|---|---|---|---|---|---|---|---|
| | | Freq | DC | Time | Freq | DC | Time |
| Response | Positive | - | 0 | - | - | 0 | - |
| Response | NoEffect | 1 | +10 | 1.1 | 1 | +10 | 1.1 |
| Response | Negative | 1 | -10 | 0.9 | - | -10 | 0.9 |

Absolute Limits

Type: Musculoskeletal

| | Array | | | Laser | | |
|---|---|---|---|---|---|---|
| | Freq | DC | Time | Freq | DC | Time |
| min | 1 | 30 | 1:00 | 10 | 50 | 0:05 |
| max | 10000 | 90 | 15:00 | 5000 | 90 | 0:40 |

NOTE: Values shown are for illustrative purposes only.

Figure 29c

| Patient Details | x |
|---|---|

Smith, John  - May 20, 1980

| Ailment | |
|---|---|
| migraines | |
| tennis elbow | |
| | |
| | |
| | |
| | |
| | |

[OK]  [Cancel]

Figure 29d

| Treatments | x |
|---|---|

Smith, John  - May 20, 1980

| Treatment Date MM/DD/YY HH:MM:SS | |
|---|---|
| 3/28/2003    14:18:40 | |
| 3/28/2003    14:19:20 | |
| 3/28/2003    14:20:15 | |
| | |
| | |
| | |
| | |

[OK]  [Cancel]

Figure 29e

| Treatment Details | | | x |
|---|---|---|---|

Smith, John   - May 20, 1980        tennis elbow

| | Array | Laser |
|---|---|---|
| Pain | 2 | |
| Disfunction | 3 | |
| Quality Of Life | 3 | |
| Previous Treatment Response | Positive | |
| Wave Length | Infrared | |
| Duty Cycle | 10 | 0 |
| Energy Density | 3.84 | 0.0 |
| Frequency | 50 | 0 |
| Treatment Time | 16:16 | 0 : 0 |

OK    Cancel

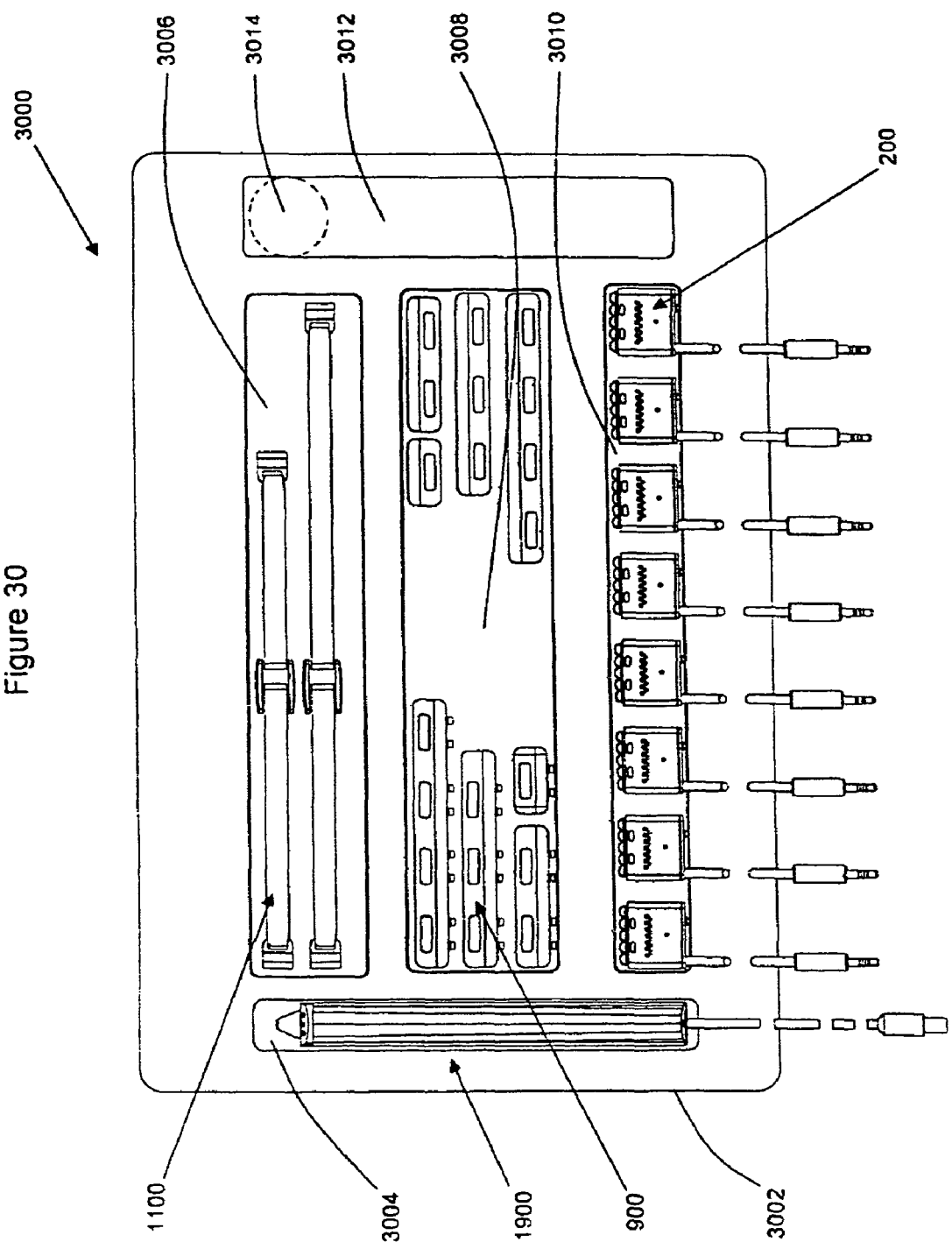

PHOTON THERAPY METHOD AND APPARATUS

CROSS-REFERENCE TO RELATED APPLICATION

This Application claims priority to U.S. Provisional Application No. 60/495,883 filed on Aug. 19, 2003, the contents of which are hereby incorporated by reference.

FIELD OF THE INVENTION

This invention relates to photon therapy and more specifically to a method and apparatus for delivering and managing the photon therapy administered to a patient.

BACKGROUND OF THE INVENTION

Photon therapy is a useful therapeutic tool available to medical practitioners for muscular skeletal disorders, wound healing, and other ailments. Photon therapy involves the application of electromagnetic energy or photons in the visible and/or infrared regions to parts of the body. These photons can cause beneficial photochemical and photobiological effects in biological tissue.

Existing systems for applying photon therapy are limited in number and have several drawbacks. Any new system and method for administering photon therapy that provides advantages over these existing systems would be most welcome.

SUMMARY

Described herein is a system for administering photon therapy to a treatment site of a patient. The system includes at least one treatment module, each of the at least one treatment module including a photon emitter, and a case for housing the photon emitter. The case includes linkers for linking treatment modules to form an arbitrary modular pattern to cover the treatment site.

Also described herein is a system and method for administering photon therapy, Smart Dose, that interactively creates treatment protocols based on a number of relevant clinical indicators, resulting in treatments that are specific to each individual, a particular ailment and their individual rate of recovery.

BRIEF DESCRIPTION OF THE DRAWINGS

Embodiments of the invention will now be described by way of example only with reference to the detailed description below and in connection with the following drawings in which

FIGS. 2(a)-(e) show a top, side, bottom, end with hooks and end with latches view respectively of a treatment module;

FIGS. 3(a)-(d) show a perspective view of a treatment module in which
FIG. 3(a) shows a top view illustrating hooks,
FIG. 3(b) shows a top view illustrating latches,
FIG. 3(c) shows a bottom view illustrating hooks,
FIG. 3(d) shows a bottom view illustrating latches;
FIGS. 8(a)-(f) show a perspective view of two treatment modules illustrating how they are linked together at various angles;
FIGS. 9(a)-(d) show a number of rails in which
FIG. 9(a) shows rails with hooks of various sizes,
FIG. 9(b) shows rails with latches of various sizes,
FIG. 9(c) shows a perspective view of a rail with hooks,
FIG. 9(d) shows a perspective view of a rail with latches;
FIGS. 10(a)-(m) show views of a matrix of treatment modules in which
FIG. 10(a) shows a top view of a 1×1 matrix of treatment modules,
FIG. 10(b) shows a top view of a 2×1 matrix of treatment modules,
FIG. 10(c) shows a top view of a 3×1 matrix of treatment modules,
FIG. 10(d) shows a side view of a 3×1 matrix of treatment modules,
FIG. 10(e) shows a top view of a 1×2 matrix of treatment modules,
FIG. 10(f) shows a top view of a 4×2 matrix of treatment modules,
FIG. 10(g) shows a side view of a 4×2 matrix of treatment modules,
FIG. 10(h) shows a top view of a 1×4 matrix of treatment modules,
FIG. 10(i) shows a side view of a 1×4 matrix of treatment modules,
FIG. 10(j) shows a top view of a 2×4 matrix of treatment modules,
FIG. 10(k) shows a side view of a 2×4 matrix of treatment modules,
FIG. 10(l) shows a top view of an irregular matrix of treatment modules,
FIG. 10(m) shows a perspective view of an irregular matrix of treatment modules;
FIGS. 11(a)-(b) show a strap assembly with rails and treatment module in which
FIG. 11(a) shows a side view,
FIG. 11(b) shows a perspective view;
FIG. 12 shows a matrix of treatment modules and a strap assembly configured for the treatment of the wrist;
FIG. 13 shows a matrix of treatment modules and a strap assembly configured for the treatment of the elbow;
FIGS. 16(a)-(d) show a number of treatment modules contained in a dish shaped holder in which
FIG. 16(a) shows a top view,
FIG. 16(b) shows a side view,
FIG. 16(c) shows a perspective view from the top,
FIG. 16(d) shows a perspective view from the bottom;
FIGS. 17(a)-(d) show a number of treatment modules contained in an angled holder in which
FIG. 17(a) shows a top view,
FIG. 17(b) shows a side view,
FIG. 17(c) shows a perspective view from the top,
FIG. 17(d) shows a perspective view from the bottom;
FIGS. 18(a)-(d) show a number of treatment modules contained in a 'C' shaped holder in which
FIG. 18(a) shows a top view,
FIG. 18(b) shows a side view,
FIG. 18(c) shows a perspective view from the top,
FIG. 18(d) shows a perspective view from the bottom;
FIGS. 19(a)-(f) show a treatment pointer in which
FIG. 19(a) shows a top view,
FIG. 19(b) shows a side view,
FIG. 19(c) shows a cable end view,
FIG. 19(d) shows nose cone sensor end view,
FIG. 19(e) shows a perspective view of the side,
FIG. 19(f) shows a perspective view of the fan side;
FIGS. 22(a)-(d) show a controller module in which
FIG. 22(a) shows a top view,
FIG. 22(b) shows an end view,
FIG. 22(c) shows a perspective view with PDA docked,
FIG. 22(d) shows a perspective view with PDA removed;
FIGS. 26(a)-(t) show PDA user interface screens in which
FIG. 26(a) shows an applications screen,
FIG. 26(e) shows a patients screen,
FIG. 26(f) shows a patient profile screen,
FIG. 26(g) shows an indication screen,
FIG. 26(h) shows an add indication screen,
FIG. 26(q) shows a view protocol screen,
FIG. 26(r) shows a treatment/treatment run screen,
FIG. 26(s) shows a treatments screen,
FIG. 26(t) shows a treatment detail screen;
FIGS. 28(a)-(b) show the smart dose algorithm main elements in which
FIG. 28(a) shows the base protocol and patient specific parameters,
FIG. 28(b) shows the ailment specific parameters, recovery specific parameters and absolute limits;
FIGS. 29(a)-(e) show PC software screens in which
FIG. 29(a) shows a representative main screen,
FIG. 29(b) shows a patient list screen,
FIG. 29(c) shows an ailment list screen,
FIG. 29(d) shows a treatment list screen,
FIG. 29(e) shows a treatment details screen;
and
FIG. 30 shows a top view of a palette.

DETAILED DESCRIPTION OF THE INVENTION

Figure 1A:
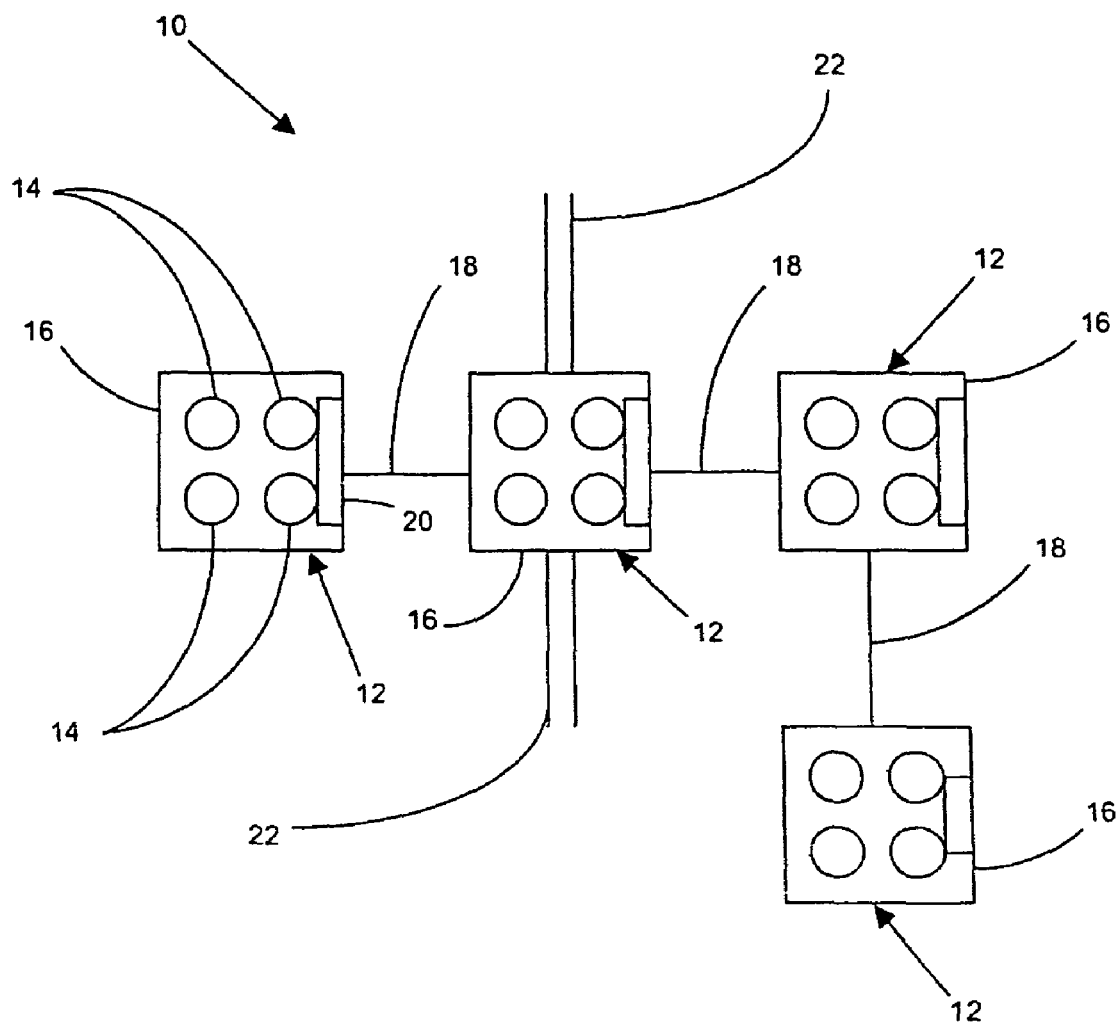
FIGS. 1(a)-1(d) show block diagrams of several aspects of the present invention dealing with administering photon therapy to a patient.

FIGS. 1(a)-1(d) show block diagrams of several aspects of the present invention dealing with administering photon therapy to a patient. In particular, FIG. 1(a) shows a block diagram of a modular system 10 for administering photon therapy to a treatment site of a patient. The modular system 10 includes a plurality of treatment modules 12, each treatment module 12 including a photon emitter 14, and a case 16 for housing the photon emitter 14. The case 16 includes at least one type of linkers 18. Further, the treatment modules 12 may also contain a cooling device 20, such as a fan. The modular system 10 can include a securing assembly 22, such as a strap or adhesive patches.

The photon emitter 14 is typically applied directly on the treatment site for therapeutic benefit. For example, for the relief of carpal tunnel syndrome, the photon emitters 14 of the treatment modules 12 are applied on the skin of the wrist. The photon emitter 14 can include an array of any light-emitting device of sufficient intensity and appropriate wavelength. For example, light emitting diodes (LEDs) and laser sources, such as laser diodes, can be used. Typical wavelengths are in the infrared to visible red region. The cooling device 20, such as a fan, vents and/or fins, help dissipate the heat generated by the photon emitters 14.

The linkers 18 permit the treatment modules 12 to be flexibly linked to each other to form an arbitrary modular pattern to cover the treatment site. In the case where the treatment modules 12 are approximately cubical, a modular pattern is any one that can be formed by placing the cubes side-by-side (or end-to-end). The linkers 18, which are described in more detail below, include a hook and latch system to connect the treatment modules 12 end-to-end and a rail assembly to connect the treatment modules 12 side-by-side.

The linkers 18 can allow any two linked treatment modules 12 to rotate over a large range of angles about a common axis, thereby allowing the system 10 to flexibly adapt or contour to a treatment site. To add more flexibility or to allow contouring in more than one plane, the rail assembly can contain a flexible material.

Figure 1B:
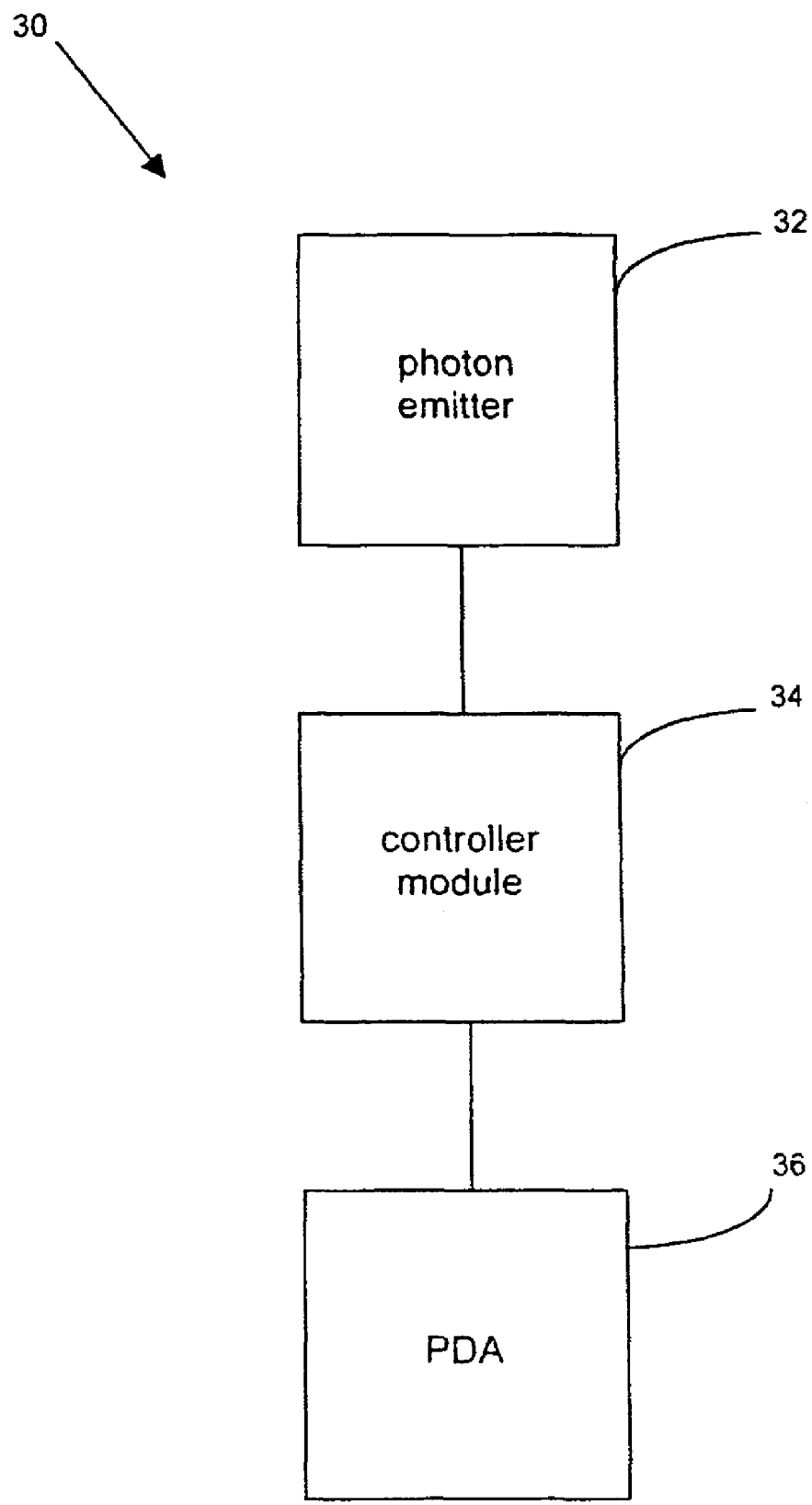

FIG. 1(b) shows a block diagram of a system 30 for administering photon therapy to a patient. The system 30 includes a photon emitter 32 with controllable properties, a controller module 34 and a personal digital assistant (PDA) 36 that is in communication with the controller module 34.

The photon emitter 32 has several controllable properties, which include at least one of pulsating frequency of the photon emitter 32, duty cycle of the photon emitter 32, and energy per unit area delivered by the photon emitter 32 at the treatment site.

The controller module 34 controls the properties of the photon emitter 32. The PDA 36 is in communication with the controller module 34 to deliver operating information thereto. The PDA 36 can communicate with the controller module 34 by a wire connection or wirelessly. The operating information is processed by the controller module 34 to control the properties of the photon emitter 32. In one embodiment, the operating information sent by the PDA 36 to the controller module 34 depends on patient information (such as age, chronicity, response to previous treatment, etc.). Thus, the properties of the photon emitter 32, and hence the photon therapy delivered to the patient, can be individually tailored to the patient. In another embodiment, the operating information sent by the PDA 36 to the controller module 34 is selected from a preset listing of fixed protocols.

In one embodiment, the operating information sent by the PDA 36 to the controller module 34 includes a signal indicative of a particular treatment protocol for the patient. The controller module 34 processes the signal and sends appropriate control instructions to the treatment module 12 that dictates the properties of the treatment module 12, such as the pulsating frequency and duty cycle of the photon emitter. In a second embodiment, the operating information sent by the PDA 36 to the controller module 34 includes the control instructions that control the properties of the treatment module 12.

Figure 1C:
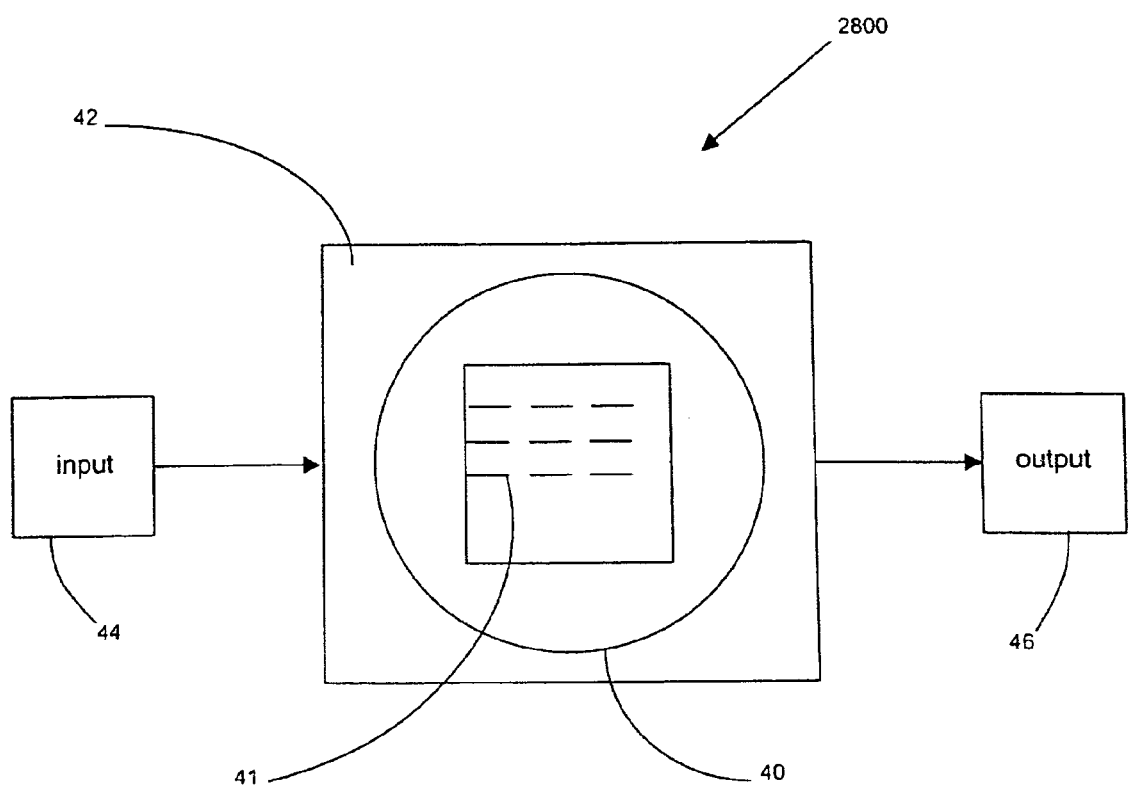

FIG. 1(c) shows a block diagram of a photon therapy system 2800, according to the principles of the present invention. The photon therapy system 2800, or Smart Dose, includes software and/or hardware for inputting personal information of a patient and outputting a treatment protocol for administering photon therapy. As herein used, Smart Dose also refers to a method for inputting personal information of a patient and outputting a treatment protocol for administering photon therapy, as described in more detail below.

A computer readable medium 40 has computer instructions 41 for administering photon therapy to a treatment site of a patient. The computer instructions 41 cause a computer 42 to input characteristics 44 of the patient, such as chronicity (acute, sub-acute, chronic, etc.) and target depth at the treatment site, which is the depth of the tissue targeted for photon therapy. For example, a superficial wound would have a smaller target depth than a joint ailment in which deep tissue is involved.

The computer instructions 41 also cause the computer 42 to output operating parameters 46 for the controller module 34 that controls the photon emitter 32 for administering the photon therapy. The operating parameters include at least one of pulsating frequency of the photon emitter 32, duty cycle of the photon emitter 32, and energy per unit area of the treatment site delivered by the photon emitter 32, for example.

Figure 1D:
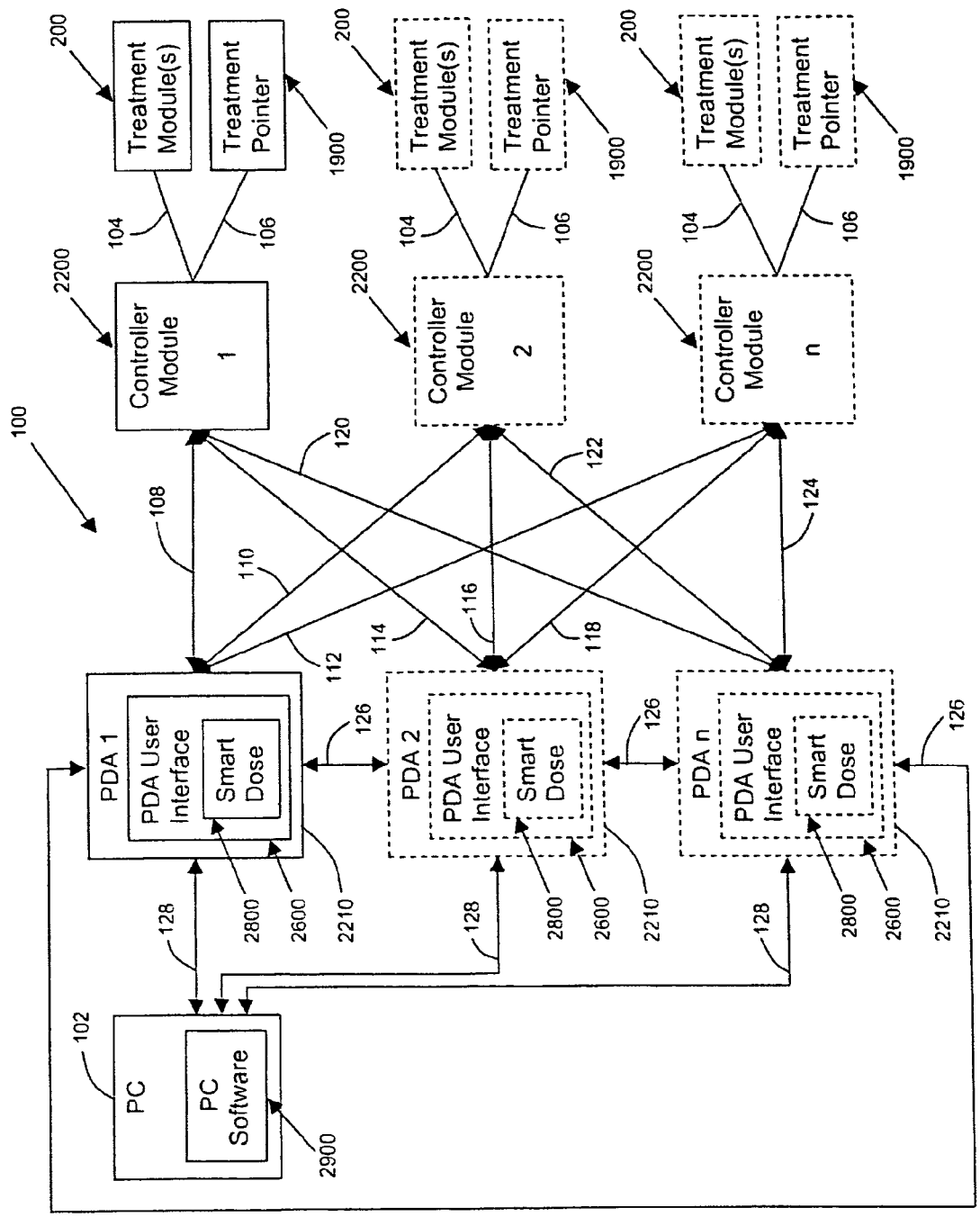

FIG. 1(d) shows a block diagram of a network system 100 for administering photon therapy. The system 100 includes treatment heads 200 and 1900, a controller module 2200, a PDA (Personal Digital Assistant) user interface 2600, an algorithm of Smart Dose 2800 and the PC (Personal Computer) software 2900. The treatment heads 200 and 1900 are designed to deliver the photon energy to the body and may include photon emitting LED (Light Emitting Diode) arrays or Laser Diodes (LD). Two physical styles of treatment heads have been designed; individual treatment modules 200 which may be linked together to cover a large surface area and a treatment pointer 1900 which can be maneuvered to target specific points. These treatment heads are controlled and powered by the controller module 2200. Control circuitry in the treatment head and/or the controller drive the photon emitters at specific optical power outputs, perform diagnostics and generate numerous treatment protocols. The controller modules communicate with the PDA user interface 2600 which runs on a PDA 2210. The PDA user interface stores and/or generates treatment protocols and downloads the information to the controller module. Treatment protocols may be generated by the Smart Dose interactive protocol generator which is embedded in the PDA User Interface. The controller module records delivered treatment parameters and uploads information to the PDA user interface. Information stored in the PDA may be transferred to the PC software 2900 which runs on a PC 102.

The architecture of the system 100 facilitates numerous configurations. The system 100 can be used standalone, using a single controller module 2200 with treatment module(s) 200 and/or treatment pointer 1900. Treatment modules are controlled via a dedicated interface 104 and treatment pointers are controlled by a dedicated interface 106. In addition, the controller module may be programmed (controlled) by the PDA 2210 running the PDA User Interface 2600 communicating via a communications interface 108. In addition, the system 100 may include the use of the PC software 2900 running on a PC 102 communicating via a communications interface 128. Any number of controller modules (1, 2 thru n) may be programmed by a single PDA via communications interface 108, 110 and 112. Alternatively, any number of PDA's (1, 2 through n) may be used with a single controller module, e.g. controller module number 1 via communications interface 108, 114 and 120. Alternatively, any number of controller modules (1 through n) can be used with any number of PDA's (1 through n) via communications interface 108-124. These communications interfaces 108-124 are labeled individually for illustrative purposes but are typically of the same type. The use of a PDA combined with the controller module includes the transfer of information for the purposes of programming and/or controlling the controller module by the PDA 2210/PDA User interface 2600. Information, such as patient information, may be exchanged directly from PDA to PDA via communications interface 126. Communications interface 108-124 may be the same as communications interface 126. A single PC can be used to communicate with any number of PDA's (1 through n) via communications interface 128.

The system architecture represented in FIG. 1(d) is ideally suited to meet the needs of a number of clinical environments. For example, a single therapist (user) with PDA 2210 using a single controller module 2200 or a single therapist with PDA using a number of controller modules, a number of therapists, each with a PDA, using a single controller module, or a number of therapists, each with a PDA, using a number of controller modules. All of the information generated and maintained by the PDA's may be transferred from PDA to PDA or to the PC software 2900. The PC software can be used to backup PDA data, merge data collected by a number of PDA's, archive data, export data to other software packages, display and print data and reload PDA's with current data. PDA manufacturer supplied software can also be used to backup PDA data on a PC 102.

Treatment Heads

Two types of treatment heads are described in the following description. FIGS. 2(a)-(e), 3(a)-(d), 4, and 5 illustrate a treatment module shown generally by numeral 200 used primarily for the treatment of large surface areas. FIGS. 19(a)-(f) and 20 illustrate a treatment pointer shown generally by numeral 1900 used primarily for the treatment of specific points.

Treatment Module(s)

Individual treatment modules house photon emitters. These photon emitters can include any number of LEDs or Laser Diodes. In FIGS. 2(a)-(e) and 3(a)-(d), in which like numerals indicate similar structures, a treatment module is shown generally by numeral 200. In this embodiment, a number of LEDs 202 are arranged as an array and protrude through the bottom of the treatment module base 204. This allows each LED 202 to make direct contact with the skin, maximizing photon penetration. The LED array is arranged by placing each individual LED as close as possible to neighboring LEDs, which maximizes the power density created by the array. This is shown in more detail by 402 of FIG. 4, a cross sectional view of the treatment module. The LEDs 202 are mounted to a printed circuit 404 board which is held in place by a number of screws 502 shown in FIG. 5, an exploded view of the treatment module. Further or alternate support may be provided by the use of an adhesive 406, which surrounds each LED 202 and bonds it to the treatment module base 204. This adhesive has the added advantage of sealing any space between the LED 202 and the base 204 in order to prevent contamination and facilitate easy cleaning of the LED array. To remove heat generated by the LED array and maintain a stable operating temperature and stable optical power output, a small cooling fan 408 is incorporated within each treatment module. The treatment module base 204 is manufactured out of a thermally conductive material such as aluminum, which will transfer heat generated by the LEDs to the base of the treatment module. A number of inlet holes 208 are provided on all sides of the treatment module, and exit holes 210 are provided on the top, allowing air flow through the treatment module, which in turn removes heat generated by the LED array. The treatment module case is made from two parts, a base 204 which contains 5 sides and a lid 206 which makes up the sixth side. The lid is designed with an internal bracket 410 which holds the fan in place within the treatment module without the use of any screws. A single screw 412 is used to hold the entire assembly together. The treatment modules may be color coded, through a process such as anodizing, to readily identify the type of LED array, so for example a treatment module containing infrared emitting LEDs may have the base 204 and lid 206 colored black while a treatment module containing red emitting LEDs may have the base 204 and lid 206 colored red.

Figure 6:
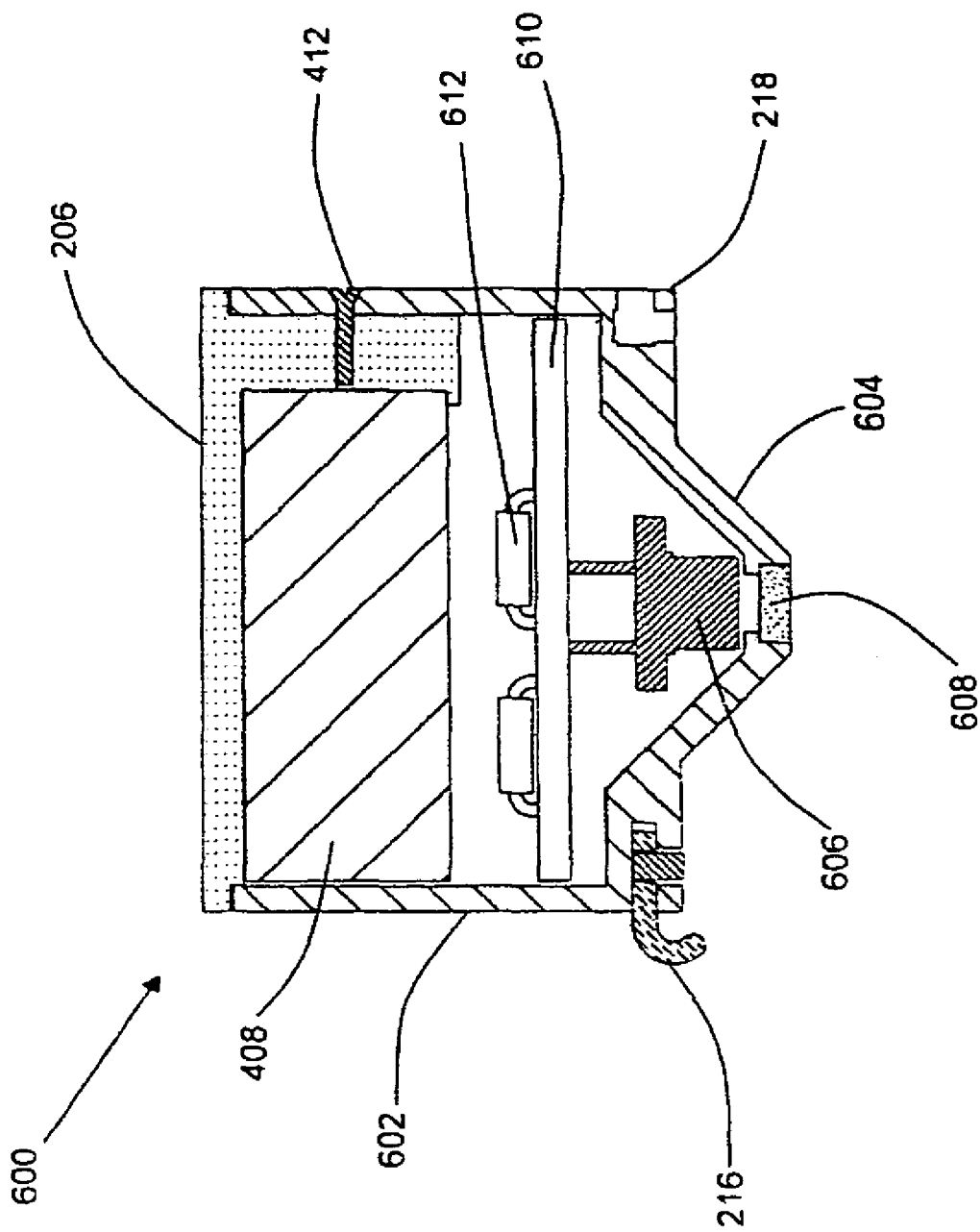
FIG. 6 shows a cross sectional view of a treatment module containing a laser diode.

In another embodiment, the treatment module contains a single laser diode 600 as shown in FIG. 6. The treatment module has on the bottom side of the base 602 a protruding cone 604, which serves to effectively move the laser diode 606 output closer to the desired target site lying below the skins surface by displacing surface skin and underlying tissue. The tip of the cone contains an optical window 608. Another embodiment may include a number of laser diodes and corresponding number of protruding cones. Circuit board 610 space is used for additional electronic driver circuitry 612 required for the laser diode. Another embodiment includes an LED array or a laser diode array, which contains an optical window covering the entire array with no protruding cone.

Figure 7:
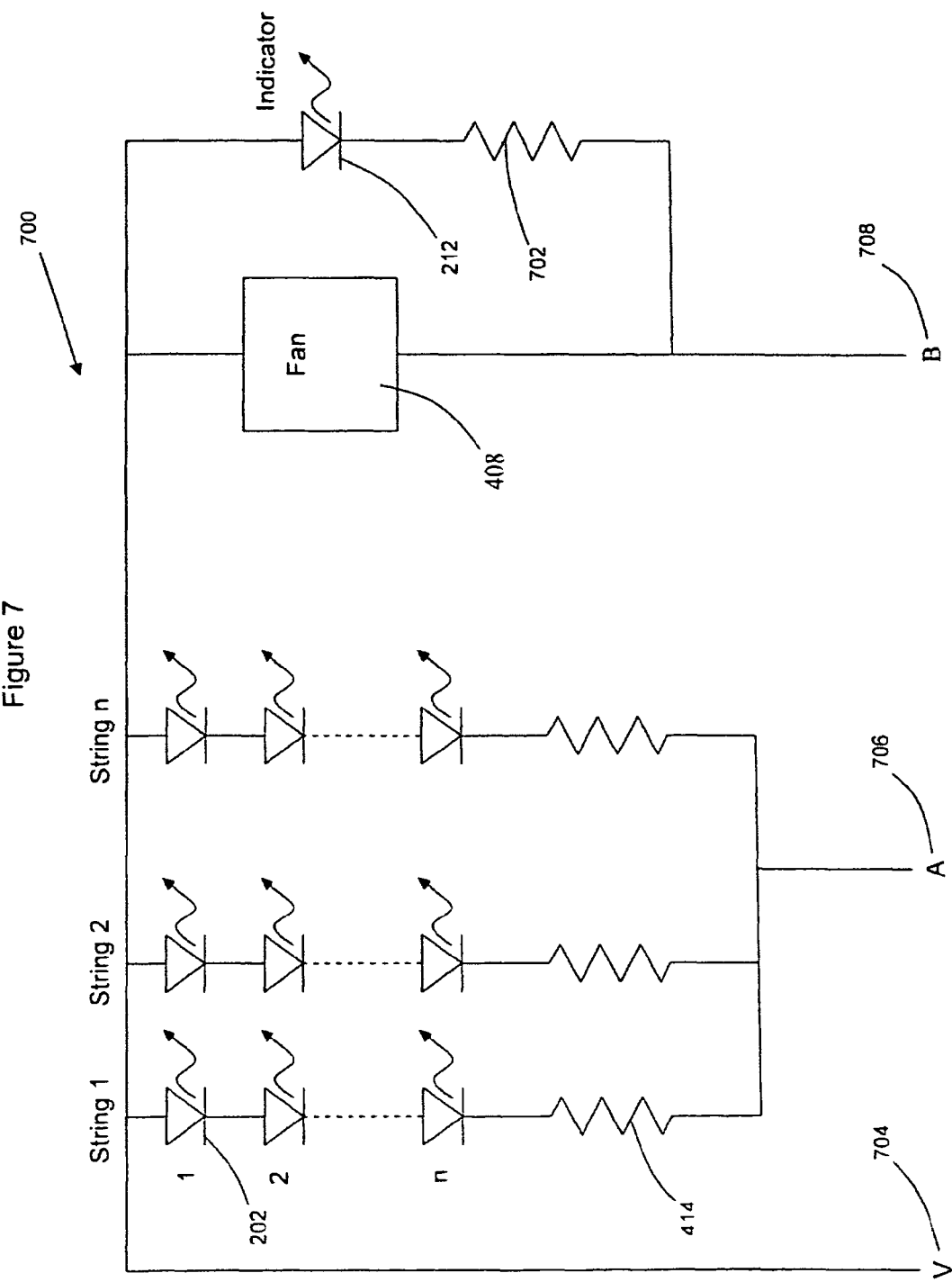
FIG. 7 is a schematic block diagram of the electronic circuitry of a treatment module.

Referring to FIG. 7, a schematic block diagram 700 of the associated electronic circuitry of the treatment module 200 is shown. Electrically, the LEDs 202 of the array are connected in series (1, 2-n) and in parallel (String1, String2-String n) allowing arrays of various sizes and LEDs of various forward voltage drops to be used. Balancing resistors 414 are used in order to compensate for variations of forward voltage between individual LEDs and between various strings of LEDs. The balancing resistors can also compensate for strings of LEDs of dissimilar numbers. The balancing resistors are mounted on the printed circuit board 404 contained within each treatment module and any heat generated by these resistors are removed by the fan 408. The LED arrays may emit photon energy, which is either red or infrared or a combination of both. Infrared arrays may include a visible LED as an indicator to show that the infrared array is active. In this embodiment, the infrared LED array contains a total of 23 diodes, 3 strings of 5 diodes and 2 strings of 4 diodes. Alternatively, the red LED array contains 5 strings of 4 diodes and 1 string of 3 diodes. Careful selection of balancing resistor 414 values allows each treatment module to have a specific total voltage drop, from 704 to 706, which can be used by the controller module for diagnostic purposes and for identification, e.g. red or infrared. Treatment modules of the same type (red or infrared) would be set to exhibit the same voltage drop. Each treatment module also contains an indicator LED 212 and associated current limiting resistor 702. The fan 408 and indicator 212 are combined in parallel reducing the number of conductors required for each treatment module. The total number of conductors required for each treatment module is 3, a supply voltage (V 704), a fan control (B 708) and LED array control (A 706). Each treatment module has a short length of cable 214 (3 conductor) of approximately 3 feet terminated with, for example, a low cost 3.5 mm male stereo phono plug 504. Note that said cable, said conductors, and associated operating sequence form the basis of the dedicated interface 104 of FIG. 1(d). LED 202 operating parameters such as optical power output, lifetime and forward voltage are temperature dependant, thus maintaining a stable operating temperature is also highly beneficial in order to maintain a stable optical power output, allow LEDs to run at higher output power levels, perform diagnostics and maintain device longevity.

Figure 4:
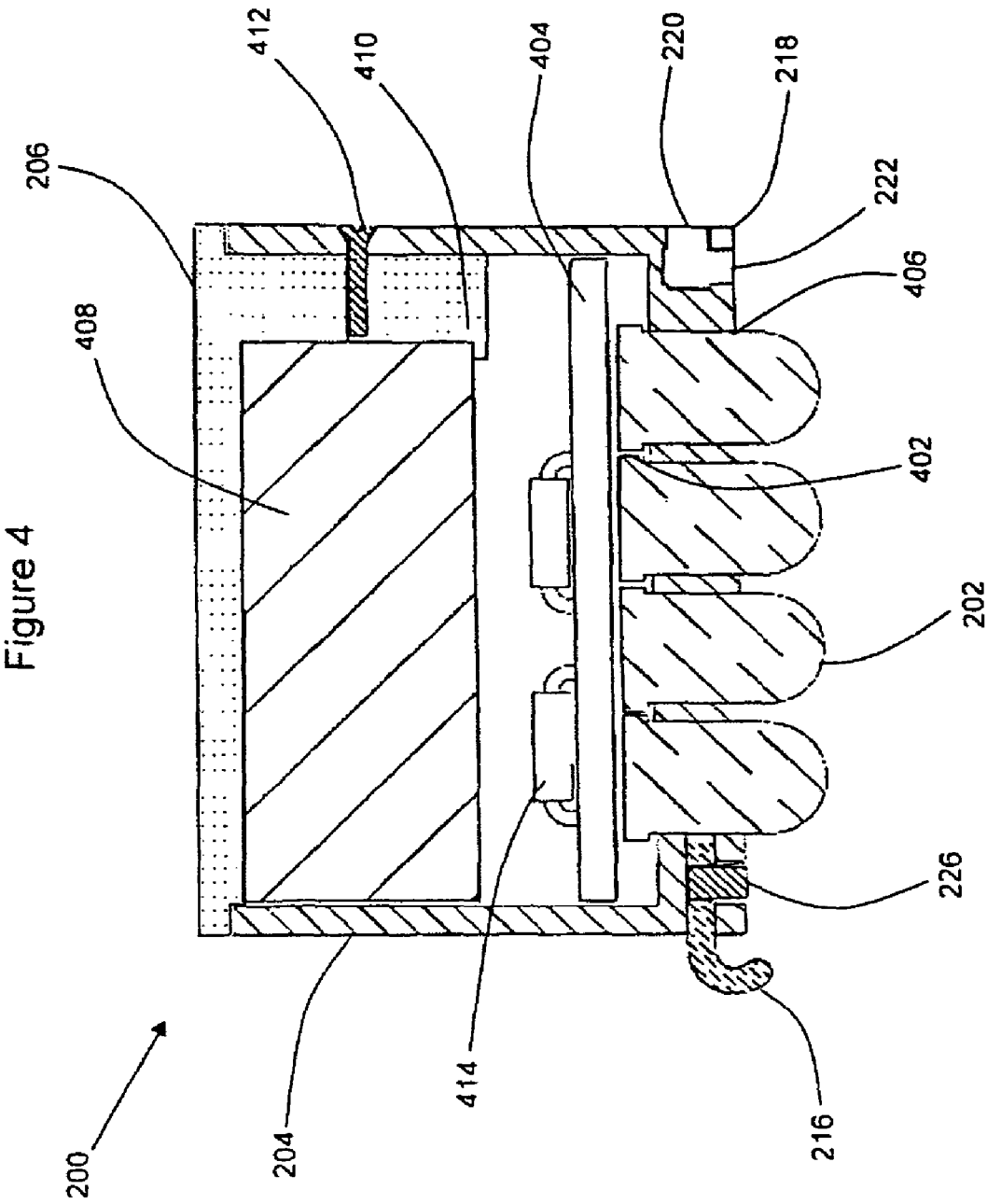
FIG. 4 shows a cross sectional view of a treatment module.
Figure 5:
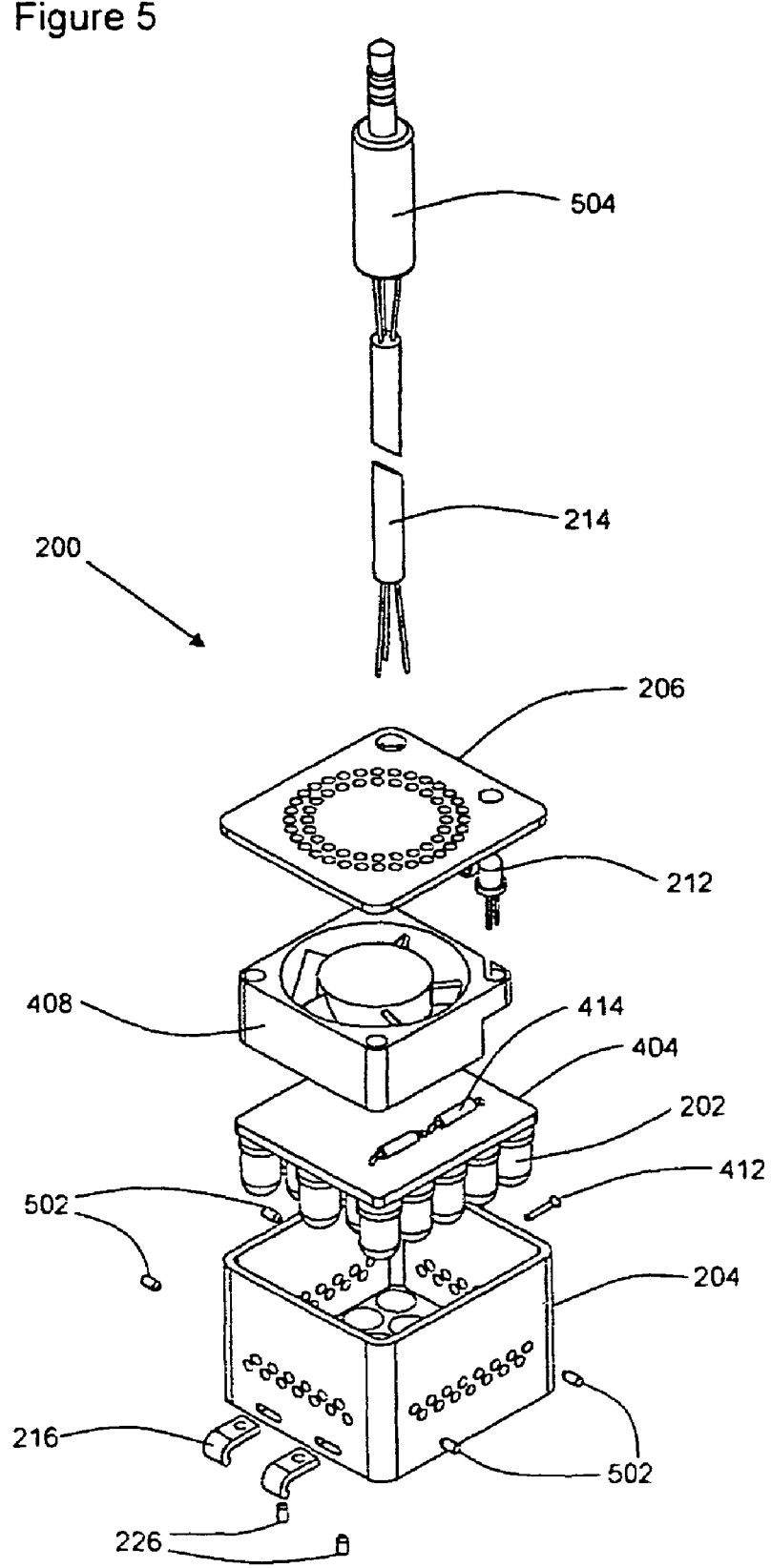
FIG. 5 shows an exploded view of a treatment module.

Individual treatment modules 200 may be linked together in numerous patterns to match the size and shape of the treatment site. This eliminates the need to supply a number of fixed size treatment heads of various predetermined sizes. Treatment modules may be connected side by side or end to end effectively creating variable sized treatment heads. The treatment modules are connected by a hook 216 and latch 218 system. In order to maintain power density as uniformly as possible from treatment module to treatment module, it is important to minimize the spacing between individual treatment modules. Thus, the size of the treatment module in proportion to the LED array is as small as possible and the hook and latch system maintains this spacing. This is accomplished by integrating the latch assembly directly into the treatment module itself. By machining a groove from two sides of the case, bottom 222 and end 220, the intersecting cavity creates a latch 218, which is best shown in FIG. 4. The hook and the latch are located in the void 224 created by the staggered configuration of the LED array located at each end of the bottom side of the treatment module, minimizing the spacing required between treatment modules when the hook and latch are engaged. Hooks 216 are made from a material such as nylon and are held in place by creating a similar cavity 220 as the latch combined with a single screw 226. Other embodiments include a hook, which is assembled with a locking mechanism, such as a wedge, in order to hold the hook in place without the use of a screw. The dimensions of the hook 216 are carefully chosen in order to allow treatment modules to be connected easily while minimizing the space between individual treatment modules. Also, the shape of the hook 216 allows adjacent treatment modules to rotate about the axis of the latch 218.

By optimizing the shape of the hook, two treatment modules 200 can be easily linked together, when tilted past their normal useable position, shown in FIG. 8(a). Once linked, the treatment modules will remain linked over a wide range of angles as shown in FIGS. 8(b)-8(f). This allows a series of treatment modules, linked together, to flex and contour to match the desired treatment site.

While individual treatment modules may be linked together end to end, they may not be linked side by side. An additional rail assembly, shown in FIGS. 9(a)-(d) generally by numeral 900, allows the treatment modules to be connected side by side. The rail replicates the hook 216 and latch 218 system of the treatment modules, as a result there are two types of rails, rails with hooks such as single width rail 902 and rails with latches such as single width rail 904. Rails can be made in various lengths in order to support various numbers of treatment modules side by side. The rails typically have a length that is approximately an integral multiple of the length of the side of the treatment module that is perpendicular to the plane of the page of FIG. 4. Single length rails 902 and 904 are used as an interface to the strap assembly 1100 shown in FIG. 11(a)-(b). Multiple length rails maintain the treatment modules as close as possible side-by-side, however, a small space is maintained in order to ease assembly, allow flexing (in the case of flexible rails) and to allow air flow for cooling. Rail lengths are designed as multiples of treatment module side widths, 1 time, single length rail 902 and 904, 2 times, double length rail 906 and 908, 3 times, triple length rails 910 and 912, 4 times, quadruple length rails 914 and 916, etc. Thus for example, linking rails 900 and treatment modules 200 together a matrix of treatment modules can be created. For example, a system composed of eight individual treatment modules, and four sized rails as per FIGS. 9(*a*) and 9(*b*) can create a matrix of treatment modules of sizes varying from 1×8 (8 end to end) to 4×2 (2 end to end) and everything in between (1×7 thought 1×1, 2×4 though 2×1, 3×2 through 3×1, 4×2 though 4×1).

FIGS. 10(*a*)-(*k*) illustrate a number of examples of a matrix of treatment modules using individual treatment modules 200 and rails 900. FIG. 10(*a*) illustrates a 1×1 matrix of treatment modules using one treatment module 200 and single length rails 902 and 904. FIG. 10(*b*) illustrates a 2×1 matrix of treatment modules using two treatment modules 200 and double length rails 906 and 908. FIG. 10(*c*) illustrates a 3×1 matrix of treatment modules using three treatment modules 200 and triple length rails 910 and 912. FIG. 10(*e*) illustrates a 1×2 matrix of treatment modules using two treatment modules 200 and single length rails 902 and 904. FIG. 10(*f*) illustrates a 4×2 matrix of treatment modules using eight treatment modules 200 and quadruple length rails 914 and 916. FIG. 10(*h*) illustrates a 1×4 matrix of treatment modules using four treatment modules 200 and single length rails 902 and 904. FIG. 10(*j*) illustrates a 2×4 matrix of treatment modules using eight treatment modules 200 and double length rails 906 and 908 (not shown). FIGS. 10(*d*), 10(*g*), 10(*i*) and 10(*k*) illustrate side views of matrix of treatment modules to demonstrate the ability to flex or contour to various shapes. FIG. 10(*i*) illustrates a matrix of treatment modules in a straight line or flat contour. FIG. 10(*g*) illustrates a matrix of treatment modules in a slight curve. FIG. 10(*k*) illustrates a matrix of treatment modules in a significant curve. FIG. 10(*l*) illustrates an irregular shaped matrix of treatment modules in the shape of an 'L' using four treatment modules 200 a triple width rail 910, a double width rail 908 and a single width rail 904. FIG. 10(*m*) illustrates a perspective view of FIG. 10(*l*). Rails 900 can be made of either a rigid material or a flexible material, the latter allowing a matrix of treatment modules to flex and contour in two directions simultaneously, end-to-end as illustrated by FIG. 10(*k*) and side-by-side.

Referring to FIG. 9(*a*)-(*b*) the rails 900 also provide an interface to a strap assembly 1100, via a large latch 918 created by slots 920, which allows the entire matrix of treatment modules, once assembled, to be affixed directly to the treatment site using the strap assembly creating a "hands free" treatment. Each rail contains a number of latches corresponding to the width multiple, for example a single width rail would contain one strap latch 918 and a quadruple width rail would contain four strap latches 918. Note that both rails with hooks FIG. 9(*a*) and rails with latches FIG. 9(*b*) contain the same style strap latch. Referring to FIG. 11(*a*)-(*b*) the strap assembly is shown generally by numeral 1100. The strap assembly is composed of a flexible fabric material 1102 and 1104 and has a hook 1106 located at each end, towards one end is a locking assembly 1108, which by pulling on the loose end 1112 will allow the strap to be tightened. The locking assembly 1108 has a release 1110, releasing the strap when desired. The strap hooks 1106 may be placed in any of the available rail latches 918 on either end of the matrix of treatment modules. For example, using a quadruple width rail, there would be four possible strap locations. This provides greater flexibility to position the array on the treatment site by selecting the appropriate strap latch location and supports the ability to use multiple straps. Also, a section of the strap assembly may contain a stretch fabric, allowing the strap assembly to apply a more uniform tension on the matrix of treatment modules.

Figure 14:
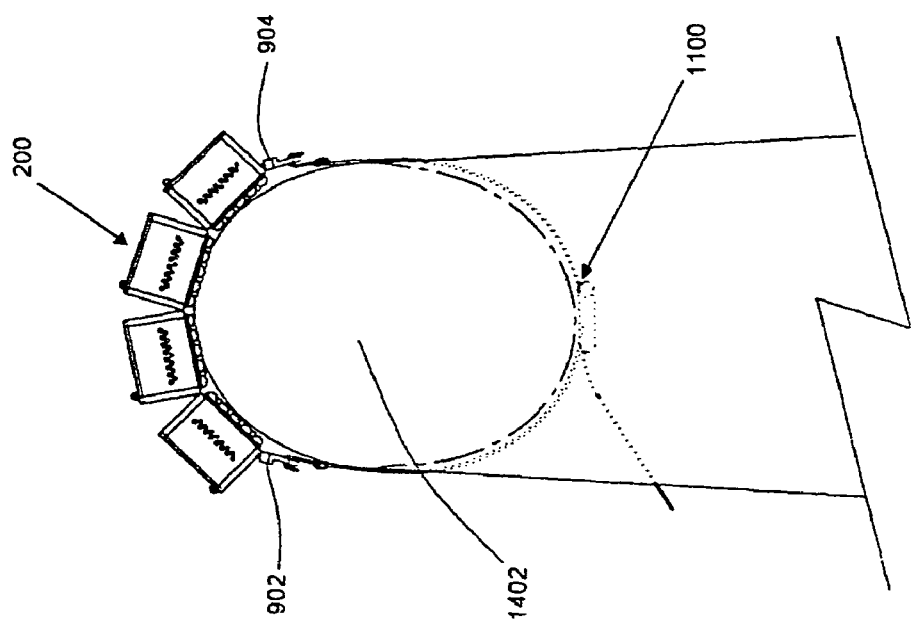
FIG. 14 shows a matrix of treatment modules and strap assembly configured for the treatment of the knee.
Figure 18C:
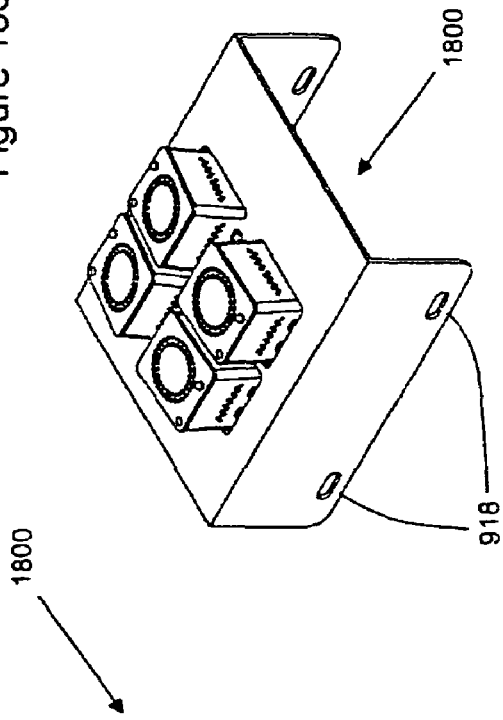
Figure 18D:
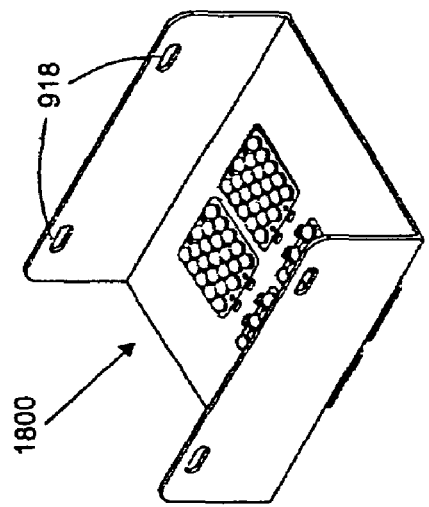
Figure 18A:
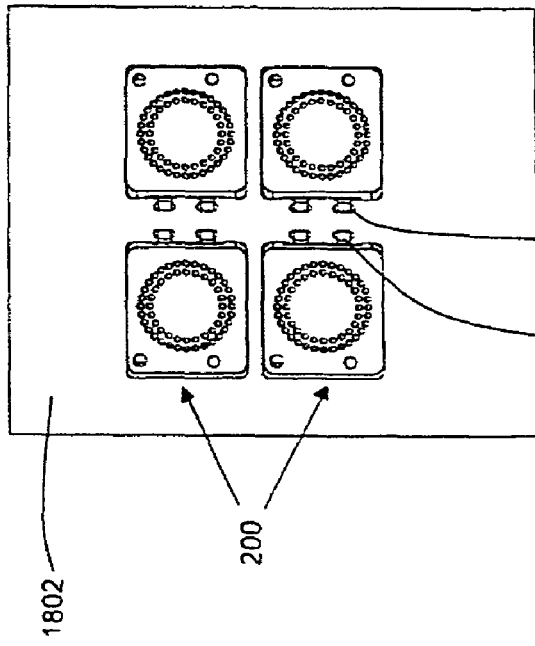
Figure 18B:
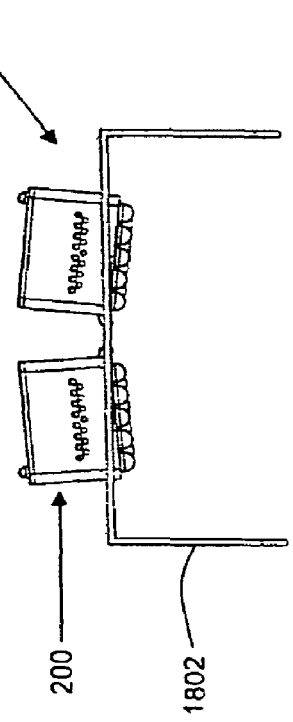
Figure 20:
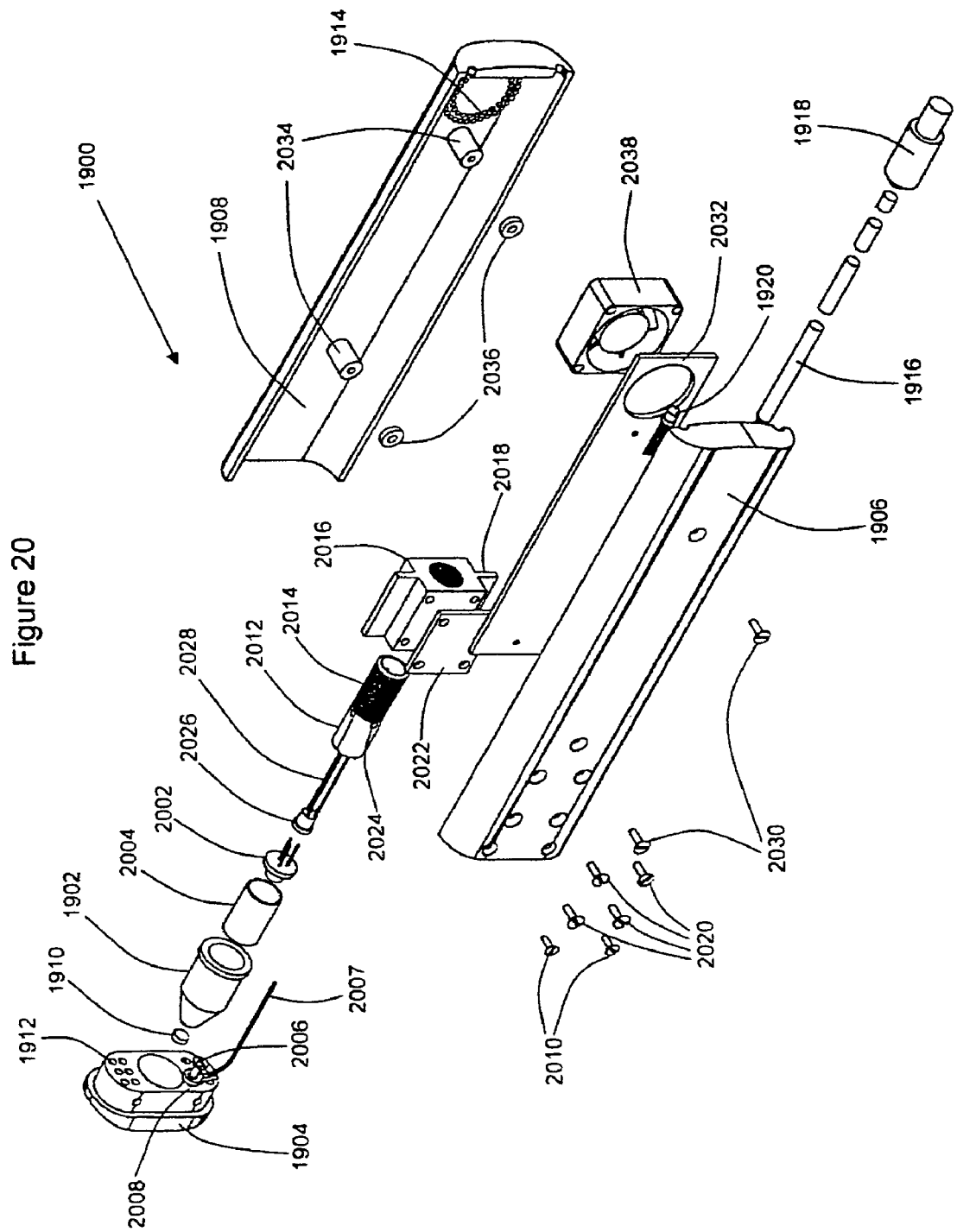
FIG. 20 shows an exploded view of a treatment pointer.

Specific clinical application examples of the matrix of treatment modules concept combined with the strap assembly 1100 is illustrated by the following; FIG. 12, a 1×1 matrix of treatment modules affixed to the wrist 1202 for the treatment of Carpal Tunnel Syndrome, FIG. 13, a 3×1 matrix of treatment modules affixed to the elbow 1302 for the treatment of tennis elbow, and FIG. 14, a 1×4 matrix of treatment modules for the treatment of the knee 1402. FIG. 10(*f*), a 4×2 matrix of treatment modules is ideally suited for the treatment of the back.

Figure 15:
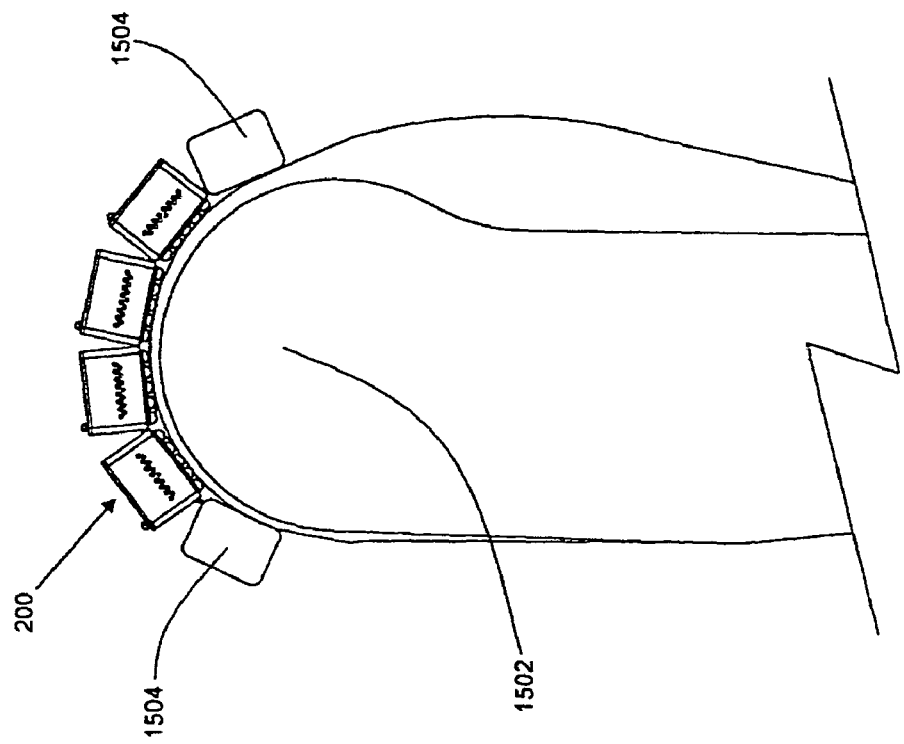
FIG. 15 shows a matrix of treatment modules and counterweights configured for the treatment of the shoulder.

A number of additional mechanisms have been designed to be used in conjunction with the treatment modules 200. Referring to FIG. 15, another method of holding the treatment modules in position on the body would encompass the use of counterweights 1504. These counterweights 1504 replicate the treatment module 200 in shape and size, including the hook 216 and latch 218 system, but are made from a solid mass. This would be particularly useful for the treatment of the shoulder 1502, as illustrated in FIG. 15 by attaching a counterweight 1504 to each end of a number of treatment modules linked together allowing the entire assembly to rest in position. This method would also be useful for treatment of the back or the neck. In another embodiment, the counterweights could be used in conjunction with the rails 900. Thus the counterweight would be a solid mass in the shape of a treatment module, or larger in size to increase the mass of the counterweight, and contain a strap assembly hook 1106. Thus the counterweights would be attached to the rails 900 of a matrix of treatment modules. Additionally, a short section of strap assembly material 1102 could be added between the counterweight and the hook 1106 allowing the weights to drape further over the treatment site.

Another mechanism used in conjunction with the treatment modules is the use of an additional holder that would house the treatment modules and maintain them at a predetermined distance from the skin, for the purposes of wound healing or on the skin for the purposes of treating areas not well suited for the strap assembly 1100 such as the hand. Additionally, the treatment modules can be angled, in one or two planes within the holder, in order to concentrate the light from a number of treatment modules to one specific area. Referring to FIGS. 16(*a*)-(*d*), a dish-shaped holder housing treatment modules is shown generally by numeral 1600. In this embodiment four treatment modules 200 are housed by the holder 1602 and are angled in one plane. The treatment modules are held in place using the hook 216 and latch 218 system, although the physical dimensions of the latch may differ resulting in latch 1604. The holder may also be held in place using the strap assembly 1100 by connecting to one of the latches 918, which are physically the same as the latches 918 of the rails 900.

Referring to FIGS. 17(*a*)-(*d*) a holder angled in shape housing treatment modules is shown generally by numeral 1700. In this embodiment four treatment modules 200 are housed by the holder 1702 and are angled in one plane. The treatment modules are held in place using the hook 216 and latch 218 system, although the physical dimensions of the latch may differ resulting in latch 1704. The holder may also be held in place using the strap assembly 1100 by connecting to one of the latches 918, which are physically the same as the latches 918 of the rails 900.

Referring to FIGS. 18(*a*)-(*d*) a holder shaped as a 'C' channel housing treatment modules is shown generally by numeral 1800. In this embodiment four treatment modules 200 are housed by the holder 1802. The treatment modules are held in place using the hook 216 and latch 218 system, although the physical dimensions of the latch may differ resulting in latch 1804. The holder may also be held in place using the strap assembly 1100 by connecting to one of the latches 918, which are physically the same as the latches 918 of the rails 900. Assemblies 1600 and 1700 are suited for the treatment of surface wounds while assembly 1800 is suited for the treatment of the hand by sliding the hand below the treatment modules.

Another mechanism used in conjunction with the treatment modules is in the form of a matt, composed of a thick rubber like material, the matt would have a centre cutout or number of cutouts to house the treatment modules. This configuration would be suited for treatment of the back, laying the matt containing treatment modules down on a patient lying in the prone position. Another mechanism would stretch the matrix of treatment modules from two points, using stretchable material in order to maintain the LED array of the treatment module in contact with irregular surfaces while maintaining uniform pressure. Alternatively, two matrix of treatment modules of example 1×4 could be stretched so that the LED array of each matrix of treatment modules would face each other. By sliding the desired treatment site, such as the hand, between the two matrix of treatment modules, the photon energy would be delivered from opposing sides.

As a result of the design of the treatment module and the matrix of treatment modules concept a number of benefits have been realized. Optical output power can be increased, allowing for deeper penetration, and improving clinical efficacy. Power density can be increased allowing for reduced treatment times. Operating parameters such as optical power output and forward voltage are stable, resulting in consistent repeatable dosages and improved self diagnosis. The lifetime of the photon emitter is less variable. A secondary stimulus, noise and vibration created by the internal fan, indicates that the silent, invisible treatment (in the case of infrared) is active. The matrix of treatment modules can vary in shape and size eliminating the need for multiple treatment heads of fixed size. Multiple sites of a patient can be treated simultaneously, an example being the wrists of a patient suffering from bilateral Carpal Tunnel Syndrome. The matrix of treatment modules and strap assembly allows for "hands free" treatment allowing a single clinician to treat multiple patients simultaneously (using multiple systems). The operating temperature of the matrix of treatment modules is maintained at safe levels (less than 40 degrees C. when in contact with the body) reducing the risk of burns. The number of treatment modules associated with a given system can vary to reduce costs. Thus, a system composed of a single or pair of treatment modules, and a simplified controller can readily be targeted towards the home/consumer market. Performance, power, power density, etc., would be identical to larger (example 8 treatment modules, complex controller) systems used by clinicians.

Treatment Pointer

In FIGS. 19(a)-(f) and 20, in which like numerals indicate similar structures, a treatment pointer is shown generally by numeral 1900. The hand held treatment pointer 1900 houses a single laser diode module 2002 and is designed to allow the clinician to direct the optical power output of the laser diode module to target specific points or targets. The physical shape of the hand held treatment pointer is designed to allow the user to comfortably hold the unit in the hand in a similar orientation as a pen or alternatively as a presentation pointer, wrapping all fingers around the unit and supporting the opposite side with the thumb. The elliptical cross section as shown in FIG. 19(d) allows increased internal space for electronic components and thermal management elements. The basis of the design is in support of the nose cone sensor 1902 and heat transfer requirements. In support of these elements the mechanical design is based on the use of electrically conductive, thermally conductive and nonconductive materials.

The nose cone sensor 1902 is designed to sense the presence of the human body or patient's skin in order to activate the laser diode module output in lieu of a mechanical switch. Electrically, this sensor is based on a common "touch switch" design, which uses the body's parasitic capacitance to change the frequency of a local oscillator. A metal sensor is required in order to serve as the contact sensor for the touch switch, thus the nose cone sensor is made of aluminum. The nose cone sensor is electrically isolated from all other system components. This is achieved by the use of an insulator 2004 between the nose cone sensor 1902 and the laser diode module 2002 as well as an insulator end cap 1904, which provides isolation between the nose cone sensor and the metal shell 1906 and 1908 of the treatment pointer. The insulators are made of a nonconductive material such as nylon or delrin. A screw 2006 hold the nose cone sensor 1902 to the insulator end cap 1904 and provides a termination point to connect the nose cone sensor to a terminal 2008 used to connect the nose cone sensor to the electronic oscillator circuit via a wire 2007. The end cap 1904 is held to the shell with the use of screws 2010. The nose cone sensor also houses an optical window 1910 which protects the laser diode module 2002 and allows the tip to be easily cleaned. The nose cone sensor may be anodized.

A heat sink is located internal to the unit in order to transfer heat away from the laser diode module 2002. The heat sink is composed of a tube 2012 which mates with the base of the laser diode module and holds the laser diode module within the insulator 2004, which in turn is within the nose cone sensor 1902. The tube is threaded at one end 2014 and screws into a larger heat sink block 2016. The heat sink block may include fins 2018 in order to increase surface area and improve heat transfer. The heat sink assembly 2012 and 2016 must also be electrically isolated from other components and is therefore mounted with the use of nylon screws 2020 and a nylon or plastic insulating plate 2022 to the shell 1906. Holes 2024 are drilled through the heat sink tube 2012 (4 holes at 0, 90, 180 and 270 degrees) near the heat sink block 2016 which are used to rotate the threaded tube with a small dowel or screwdriver, which in turn increases the pressure of the heat sink tube 2012 against the laser diode module 2002, holding the assembly firmly in place. A transistor socket 2026 feeds through the heat sink assembly 2012 and 2016 with wires 2028 in order to connect the laser diode module to the printed circuit board 2032. The shell 1906 and 1908 is held together with the use of screws 2030, which also holds in place the printed circuit board 2032 with the use of standoffs 2034 and additional spacers 2036. A cooling LD fan 2038 is also mounted to the printed circuit board. The LD fan is used to cool the laser diode module 2002 by cooling the internal heat sink assembly 2012 and 2016. Inlet holes 1912 are provided in the insulator end cap 1904, near the laser diode module, which allows air flow to pass over the internal heat sink assembly and also cool any electronic components mounted on the printed circuit board 2032 which generate heat. Outlet holes 1914 are provided on the side at the rear end of the unit, away from the area where the users hand would obstruct the air flow. The optical output of a laser diode and its useable lifespan are highly temperature dependant, thus active cooling is provided in order to maintain stable operating conditions and avoid premature failure of the laser diode. The treatment pointer 1900 also has a cable 1916 terminated with a connector 1918 exiting the rear of the unit (opposite end of the nose cone sensor) and a bi-colored indicator 1920 also on the rear of the unit readily viewable by the user.

Figure 21:
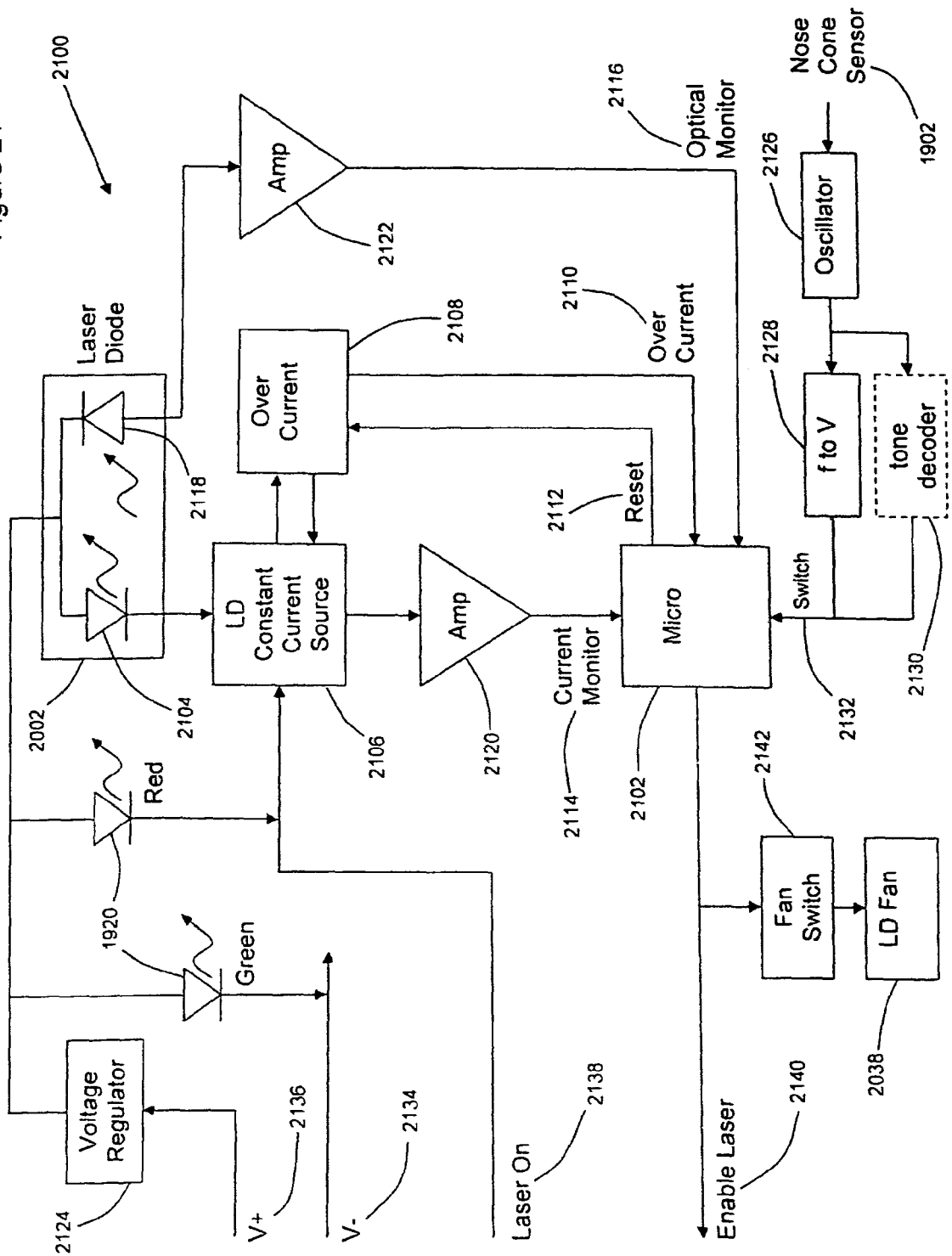
FIG. 21 is a schematic block diagram of the electronic circuitry of a treatment pointer.
Figure 22C:
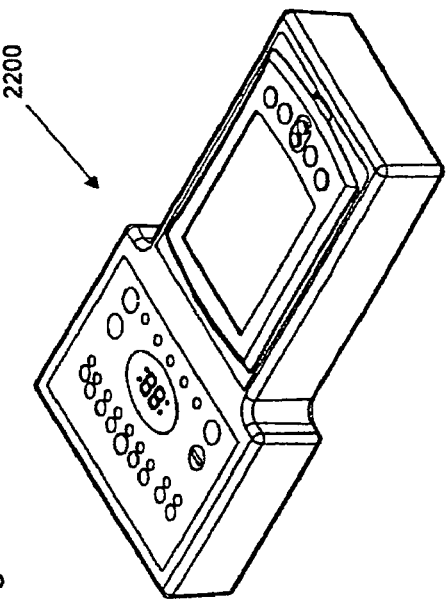
Figure 22D:
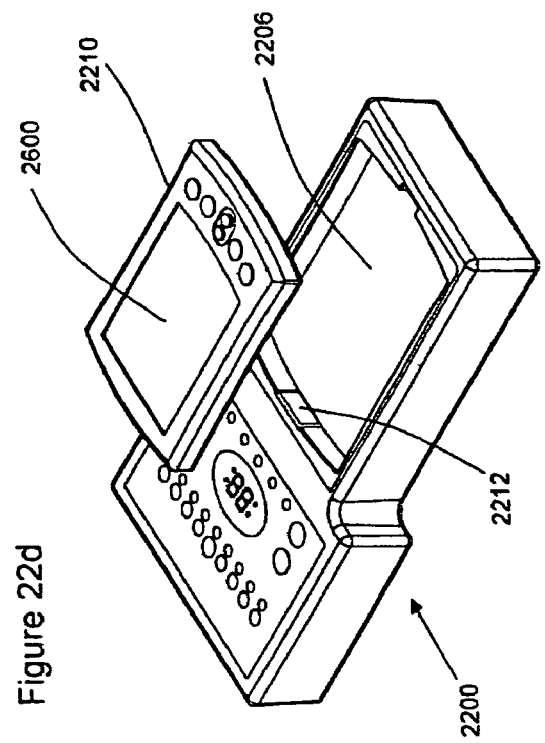
Figure 22A:
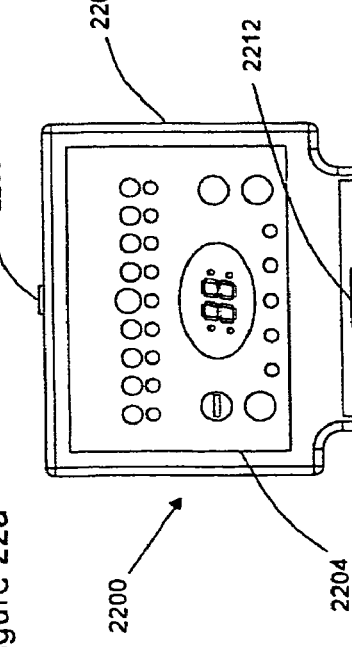
Figure 22B:

Referring to FIG. 21, a schematic block diagram of the associated electronic circuitry of the treatment pointer 1900 is shown generally by numeral 2100. A number of electronic modules are contained within the treatment pointer and in the preferred embodiment includes the use of a microprocessor (micro) 2102. In order to maintain the optical output power of the laser diode 2104 at a stable preset value a LD constant current source 2106 is used. The output of the LD constant current source can be adjusted in order to compensate for the individual characteristics of each laser diode. In order to ensure that the maximum current rating is not exceeded to the laser diode 2104 an over current 2108 trip circuit is used which can be adjusted to shut the LD constant current source down at a predetermined level. The micro monitors the over current trip circuit via over current 2110 and can reset the circuit via reset 2112. In order to ensure the optical output is accurate two separate feedback indicators are monitored by the micro prior to each use, laser diode forward current monitor 2114 and the output of the internal laser diode module 2002 monitor photodiode 2118 via optical monitor 2116. This is achieved with the use of two amplifier circuits 2120 and 2122, which scale the current monitor and photodiode signals to representative voltage levels. An on board voltage regulator 2124 supplies a reduced voltage for electronic circuitry and to supply the laser diode module 2002. The "touch switch" nose cone sensor 1902 is driven by a local oscillator 2126 followed by a frequency to voltage converter 2128 in order to enable the laser diode module output via a representative voltage, switch 2132, monitored by the micro. Alternatively, a tone decoder circuit can be used as the local oscillator and a tone decoder circuit 2130 can be used to detect when the oscillator frequency drifts outside of the pass-band, resulting in a logic signal, switch 2132, representative of sensor contact. The local micro 2102 combines analog signals (current monitor 2114, optical monitor 2116, and switch 2132) and digital signals (reset 2112, over current 2110, and enable laser 2140) in support of its software sequence of operation. The entire treatment pointer is controlled by a four wire interface, which includes a common (V− 2134) and positive (V+ 2136) supply voltage, a control signal provided from the controller module (laser on 2138) and an enable signal provided by the micro (enable laser 2140). The interface, cable 1916, and associated operating sequence form the basis of the dedicated interface 106 of FIG. 1(*d*). The treatment pointer also contains a bi-color indicator 1920 (red, green). A fan switch 2142 is used to turn the LD fan 2038 on and off.

The sequence of operation for the treatment pointer 1900 is as follows. Power is controlled by the controller module 2200, when a protocol is selected which requires the use of the treatment pointer 1900 and the start button 2312 is pressed the controller module will turn the power on to the treatment pointer via V+ 2136. When powered the bi-colored indicator 1920 of the treatment pointer will glow green. On power up, and after a short delay, the treatment pointer micro 2102 will send a reset pulse via reset 2112 to the over current 2108 trip circuit. The micro 2102 will continuously monitor the voltage/level of the switch circuit (switch 2132), when the voltage/logic level changes based on predetermined values, indicating that the "touch switch" is on (the nose cone sensor 1902 is in contact with the skin) it will send an enable (enable laser 2140) signal to the controller module. The controller module will then send a short test pulse (laser on 2138), to turn the laser diode 2104 on. The micro will then measure the optical monitor 2116 and current monitor 2114 signals and check if they are within a predefined range, if correct the enable laser 2140 signal will remain on, if not, the enable laser signal will be shut off. The laser diode 2104 will remain on until the "touch switch" goes off (the nose cone sensor 1902 is removed from the skin), then enable laser 2140 will go off and the controller module will shut off laser on 2138 which in turn shuts off the laser diode 2104. The laser on 2138 signal from the controller module also contains the modulation waveform (square wave) and therefore controls the output of the laser diode 2104 directly. If the over current 2108 trip circuit detects that the laser diode current is higher than a predetermined amount the circuit will trip, shutting off the LD constant current source immediately. The micro 2102 will monitor the over current 2110 signal at all times, when tripped, the over current 2110 level will change state, the enable laser will be shut off, the controller module will turn off laser on 2138 and the treatment will stop. The bi-color indicator 1920 is also controlled by the laser on 2138 signal. Thus, whenever the laser diode 2104 is on, the indicator glows red. A delay hold circuit may be added to hold the indicator red, for modulation waveforms which contain a square wave (delay equals one period at the lowest frequency). The LD fan is controlled by the enable laser signal via a fan switch 2142 circuit, and will be active (cooling) whenever enable laser 2140 is on.

Controller Module(s)

Referring to FIGS. 22(*a*)-(*d*) an embodiment of a controller module is shown generally by numeral 2200. The controller module 2200 is described in general terms as a number of different controller models are available, all based on the same fundamental design and operation. The most advanced controller module will be described in detail. The controller module is a hand held device composed of a case 2202, which contains a user interface 2204 and a PDA docking station 2206. The controller module may be used with or without the PDA 2210. The controller module(s) is/are used to control the treatment heads, treatment modules 200 (red and infrared) and the treatment pointer 1900. It also controls/runs treatment protocols including the length of time of treatment, which treatment head to use, performs diagnostics and generates modulation waveforms. The controller module is powered by an external power supply which connects via a power jack 2208. The PDA 2210 can communicate with the controller module via either the IR (infra red) port 2212 or the electrical interface port (not shown but typically located near 2214). A slot is provided 2214 in order to remove the PDA 2210 from the controller module 2200. The controller module can run preset treatment protocols stored locally in the controller or run treatment protocols downloaded from the PDA user interface 2600. The result of the PDA/controller module configuration is a highly portable, "bedside" friendly system which takes full advantage of all of the benefits afforded by the PDA, ease of data entry, touch screen, color display, memory, computational power, etc.

Figure 23:
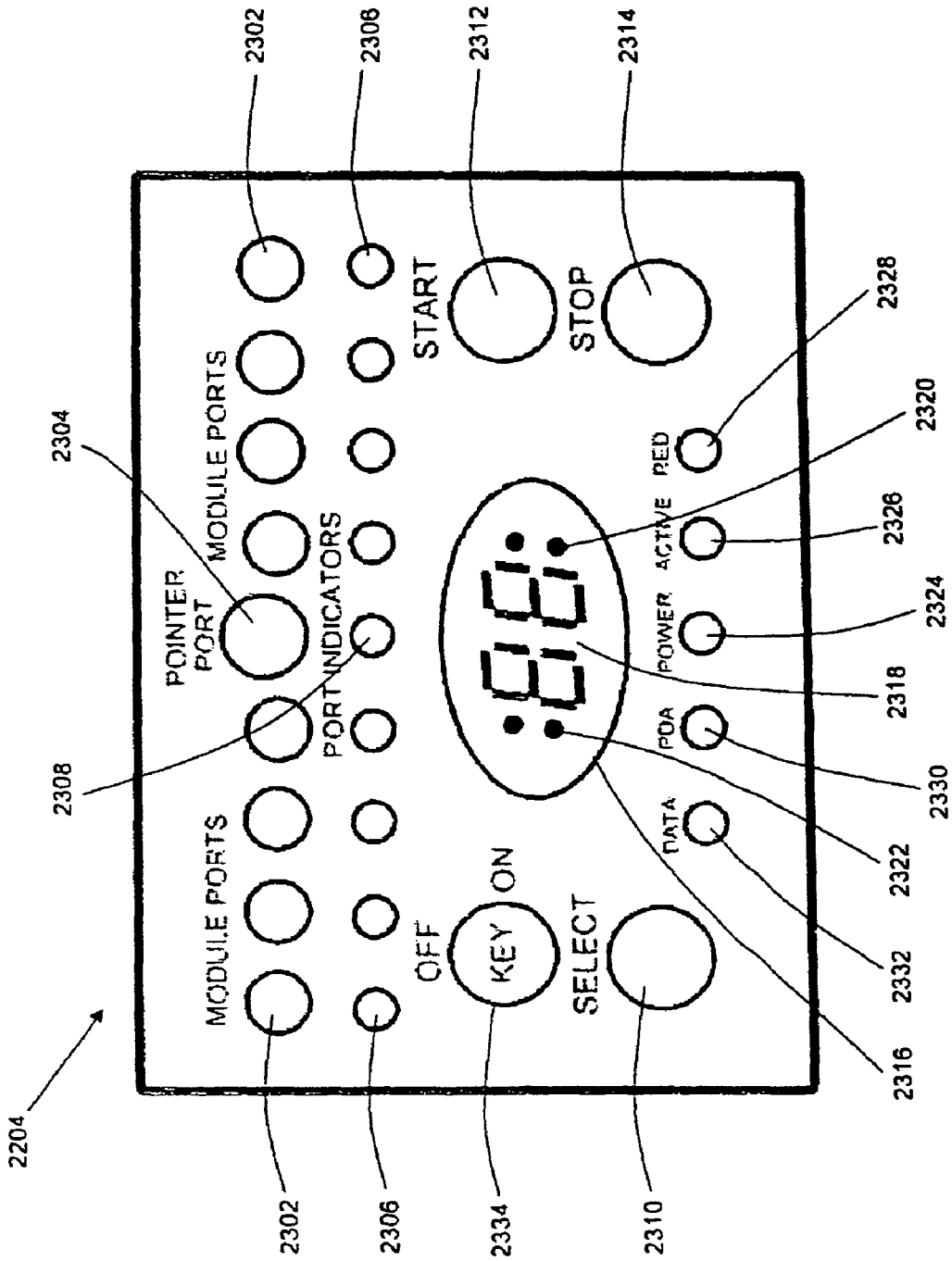
FIG. 23 shows the user interface of a controller module.
Figure 25:
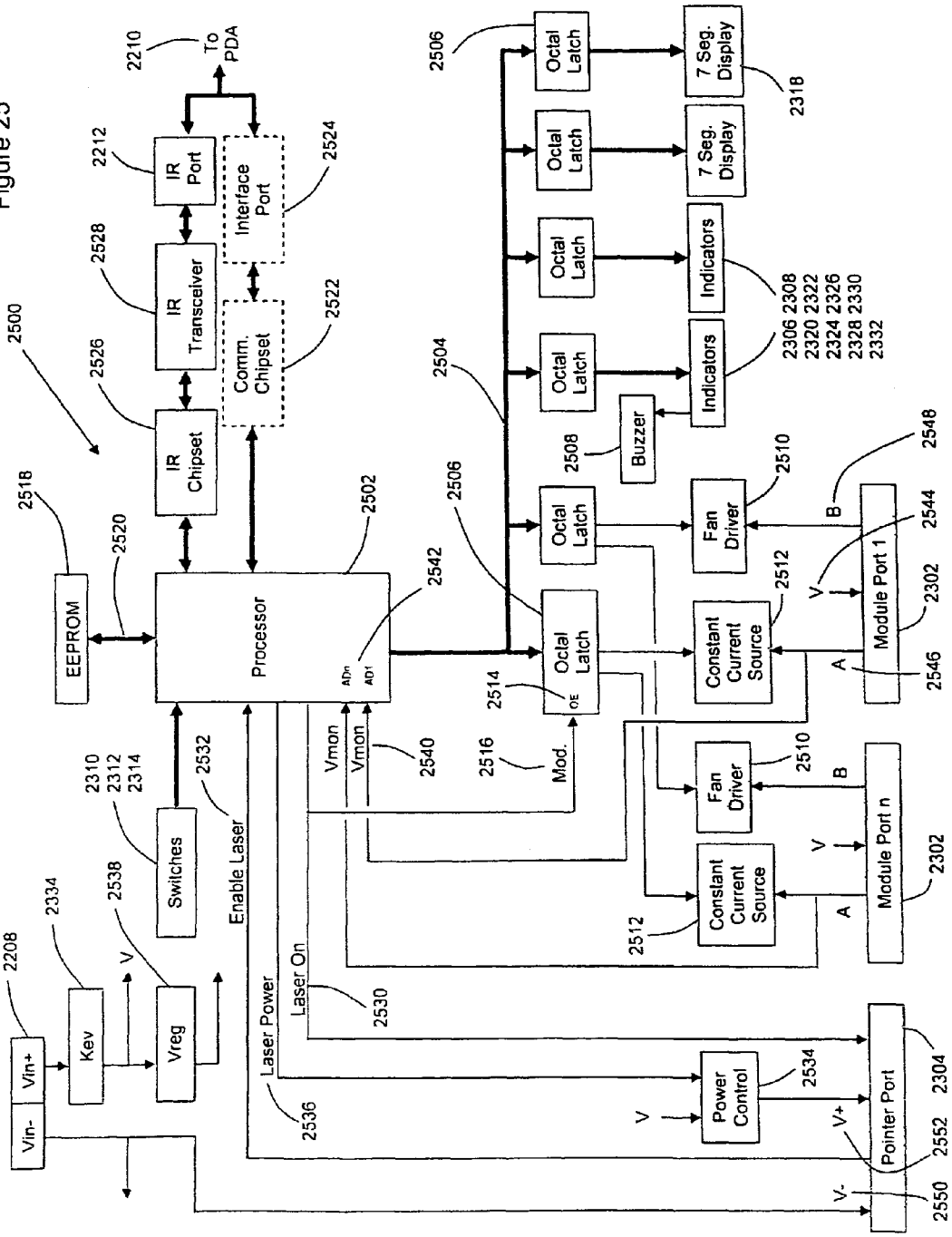
FIG. 25 is a schematic block diagram of the electronic circuitry of a controller module.
Figure 26B:
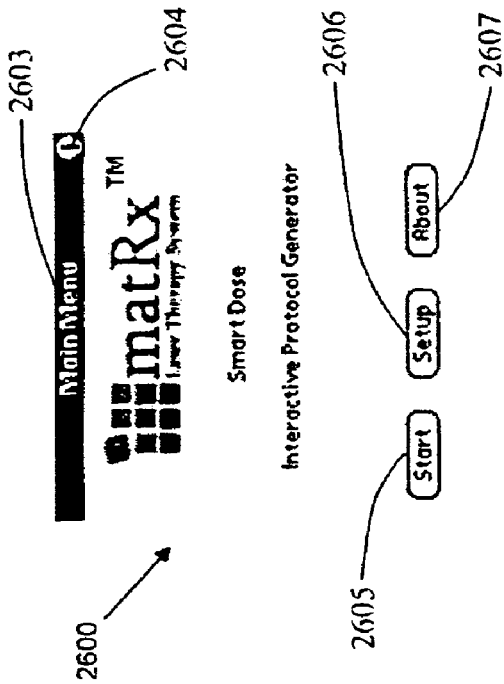
FIG. 26(b) shows a main menu screen.
Figure 26D:
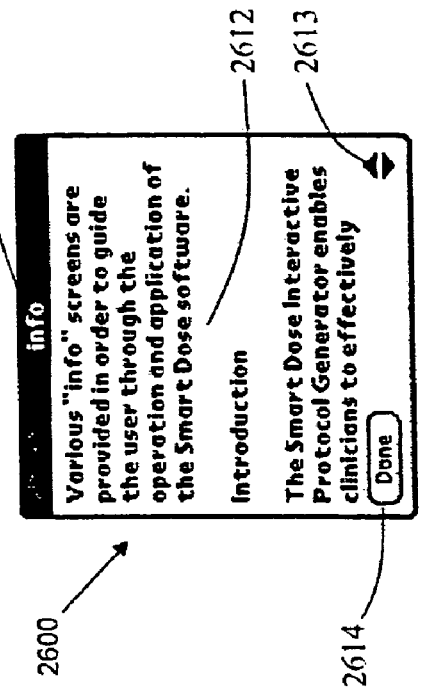
FIG. 26(d) shows an info screen.
Figure 26A:
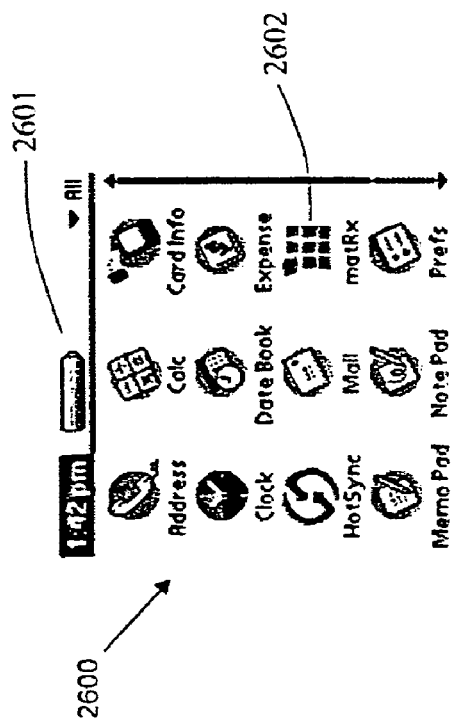
Figure 26C:
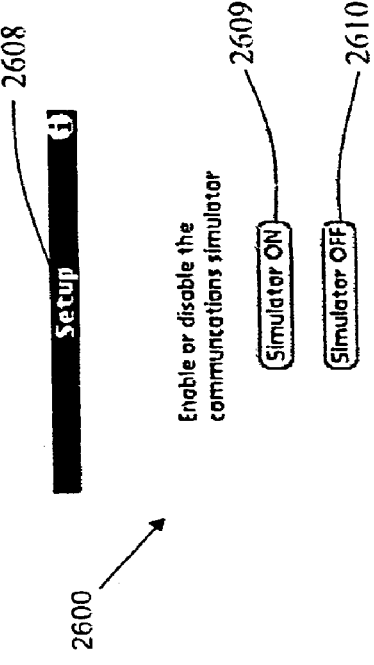
FIG. 26(c) shows a setup screen.
Figures 26I, 26J, 26K, 26L:
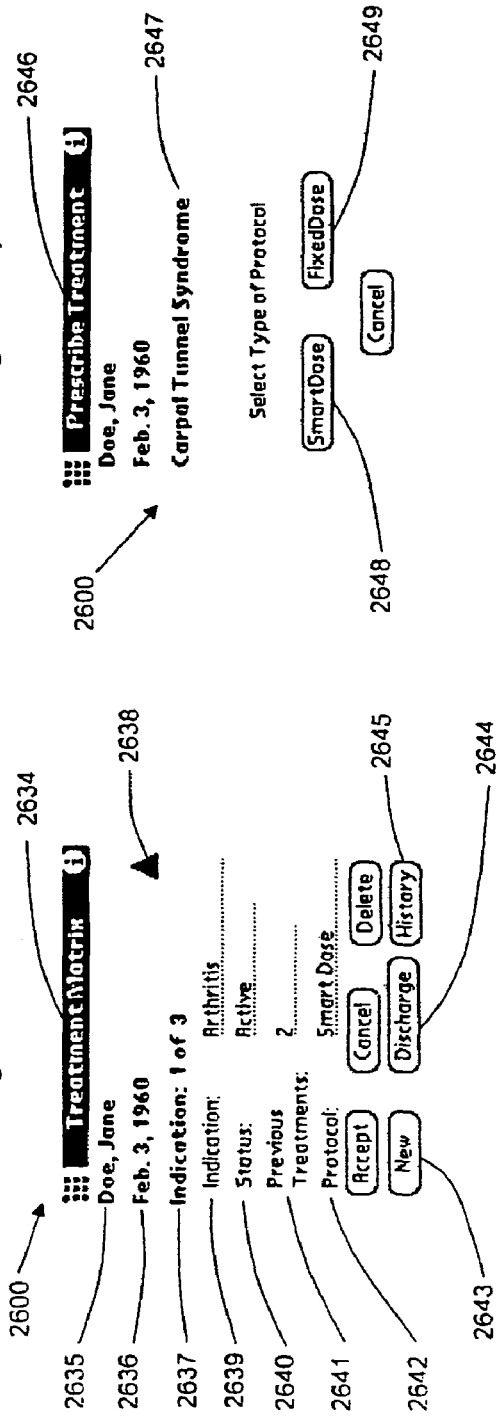
FIG. 26(i) shows a treatment matrix screen.
FIG. 26(j) shows a prescribe treatment screen.
FIG. 26(k) shows a fixed dose screen.
FIG. 26(l) shows a create fixed dose screen.
Figure 26M:
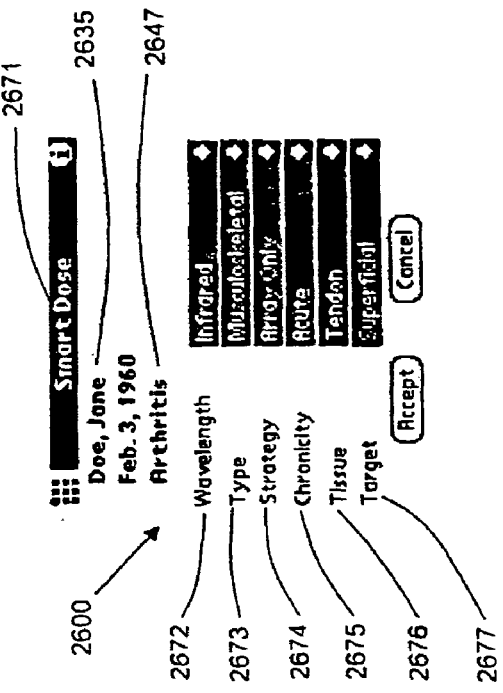
FIG. 26(m) shows a record assessment screen.
Figure 26N:
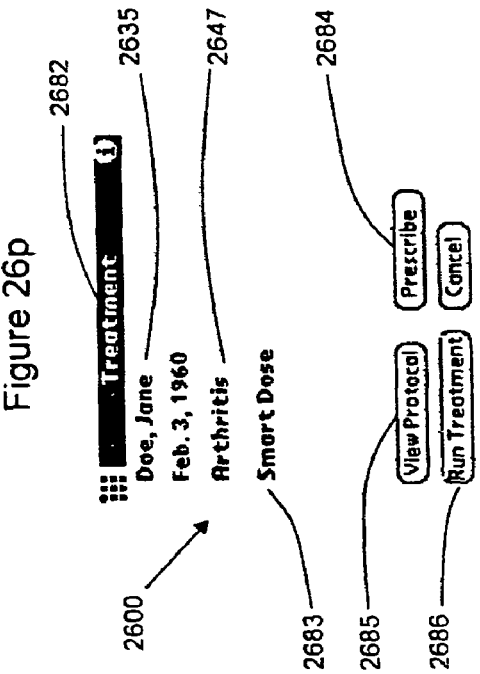
FIG. 26(n) shows a smart dose screen.
Figure 26O:
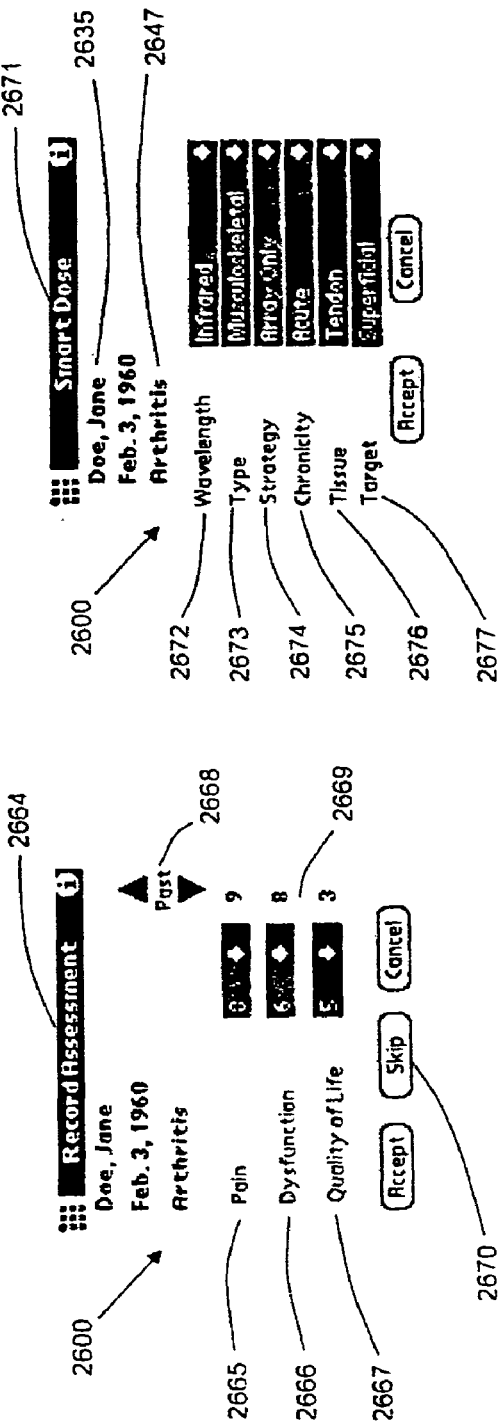
FIG. 26(o) shows a treatment response screen.
Figure 26P:
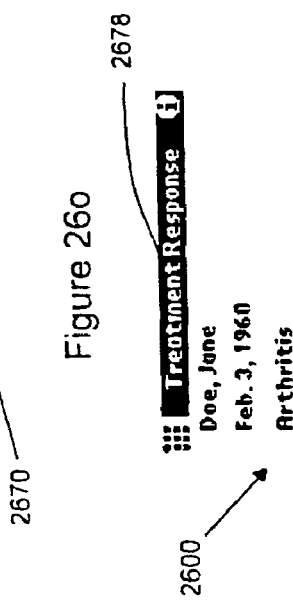
FIG. 26(p) shows a treatment screen.
Figure 27A:
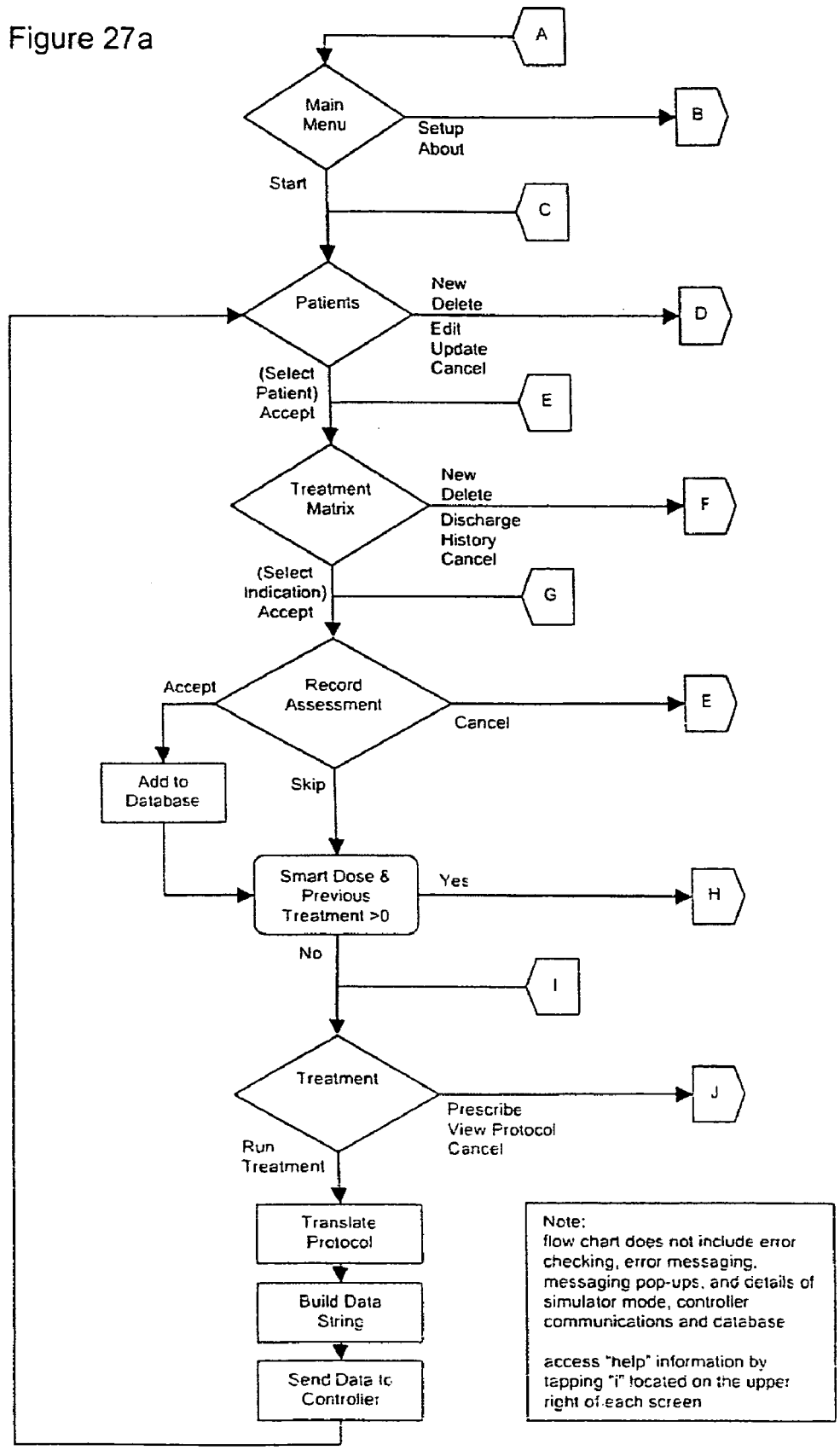
FIGS. 27(a)-(g) are flowcharts of the PDA user interface.
Figure 27B:
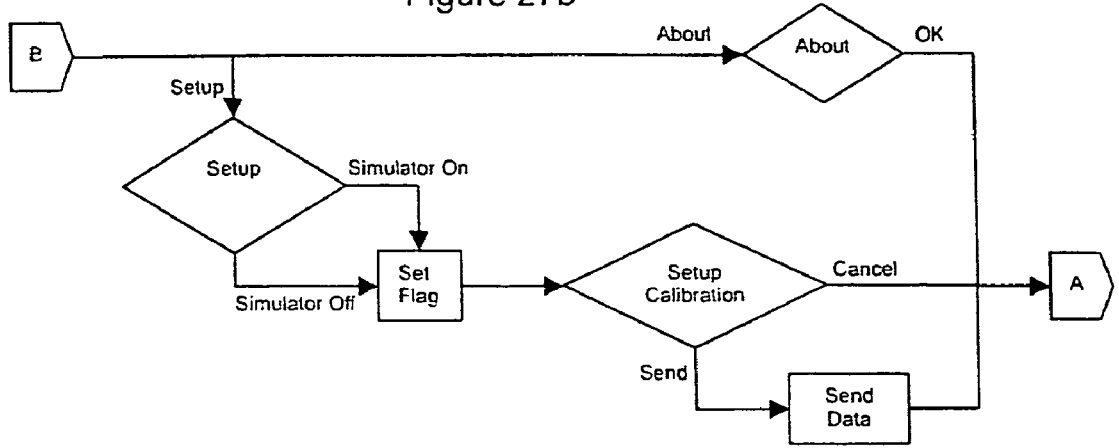
Figure 27C:
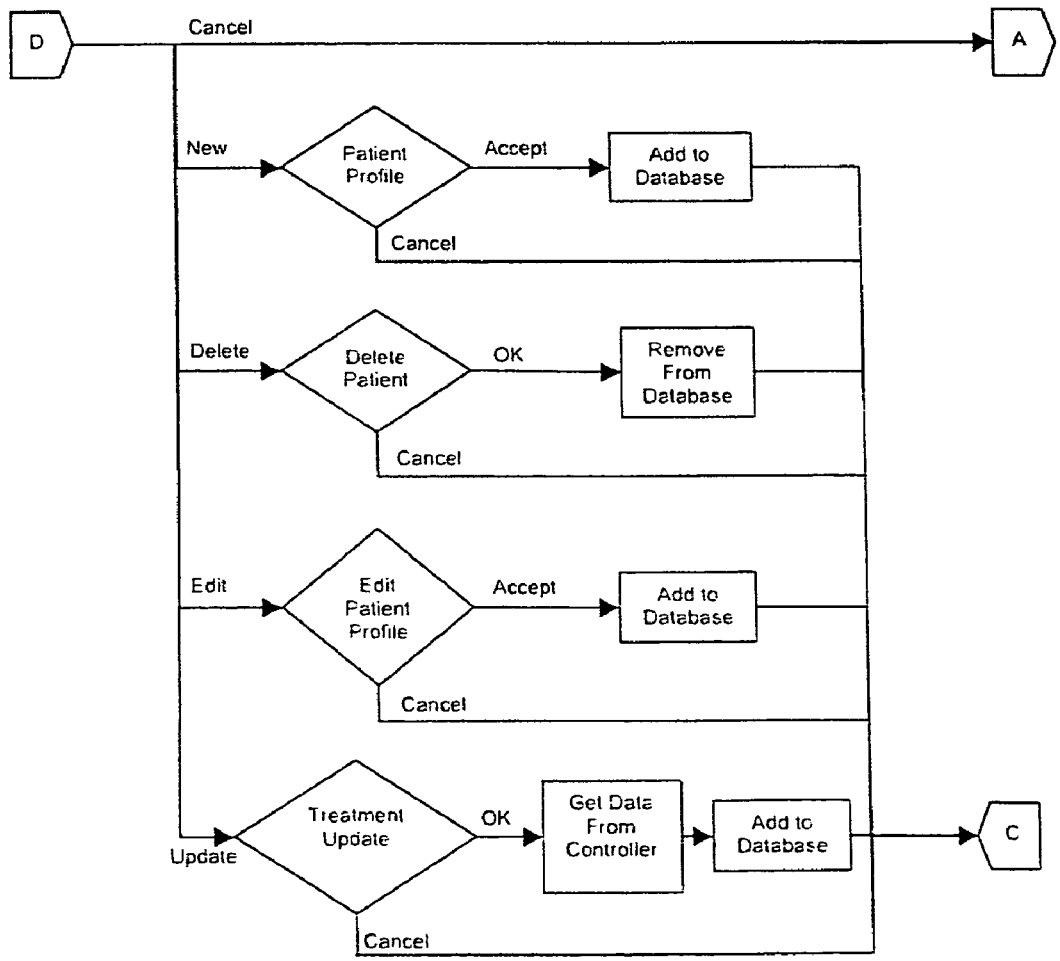
Figure 27D:
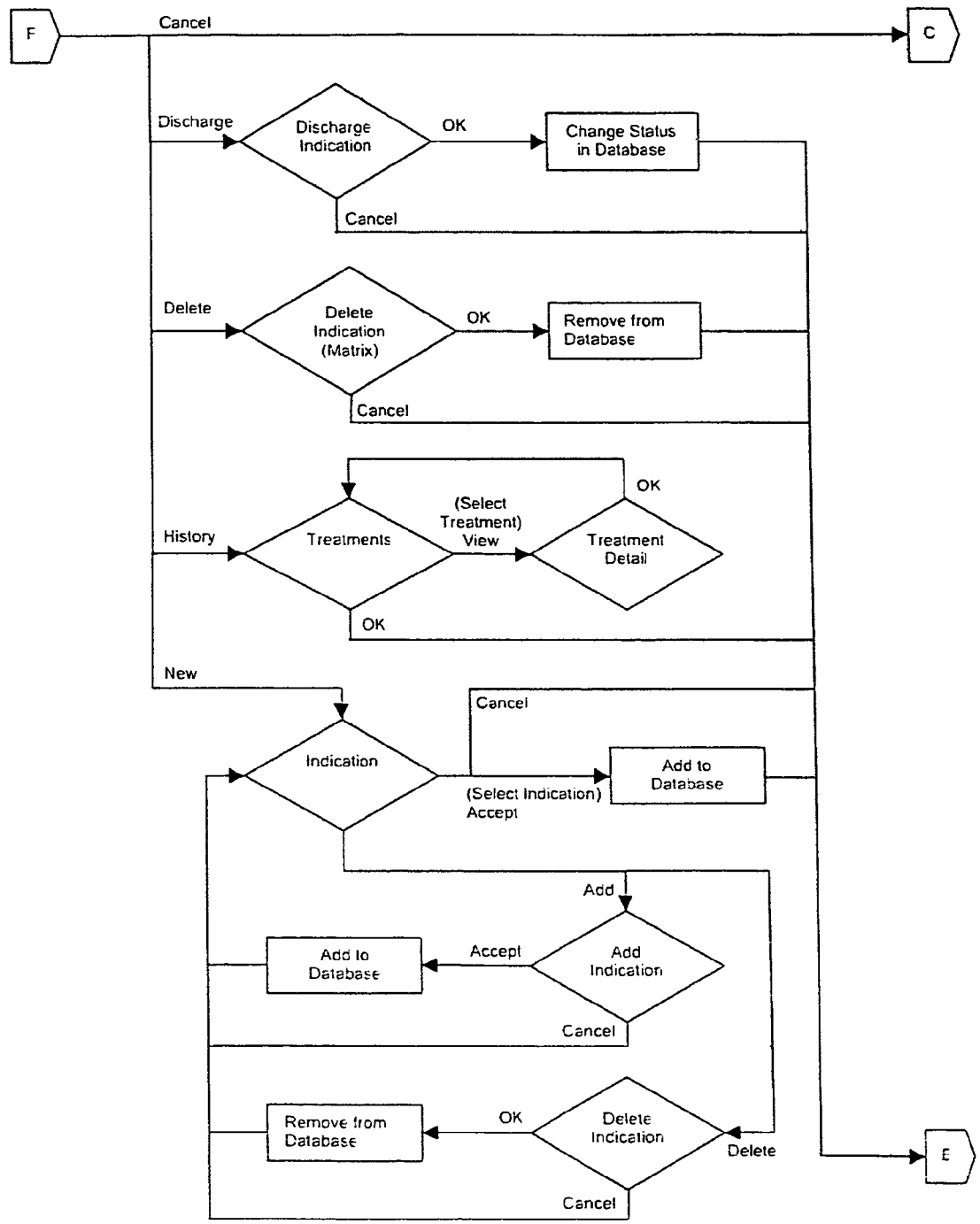
Figure 27E:
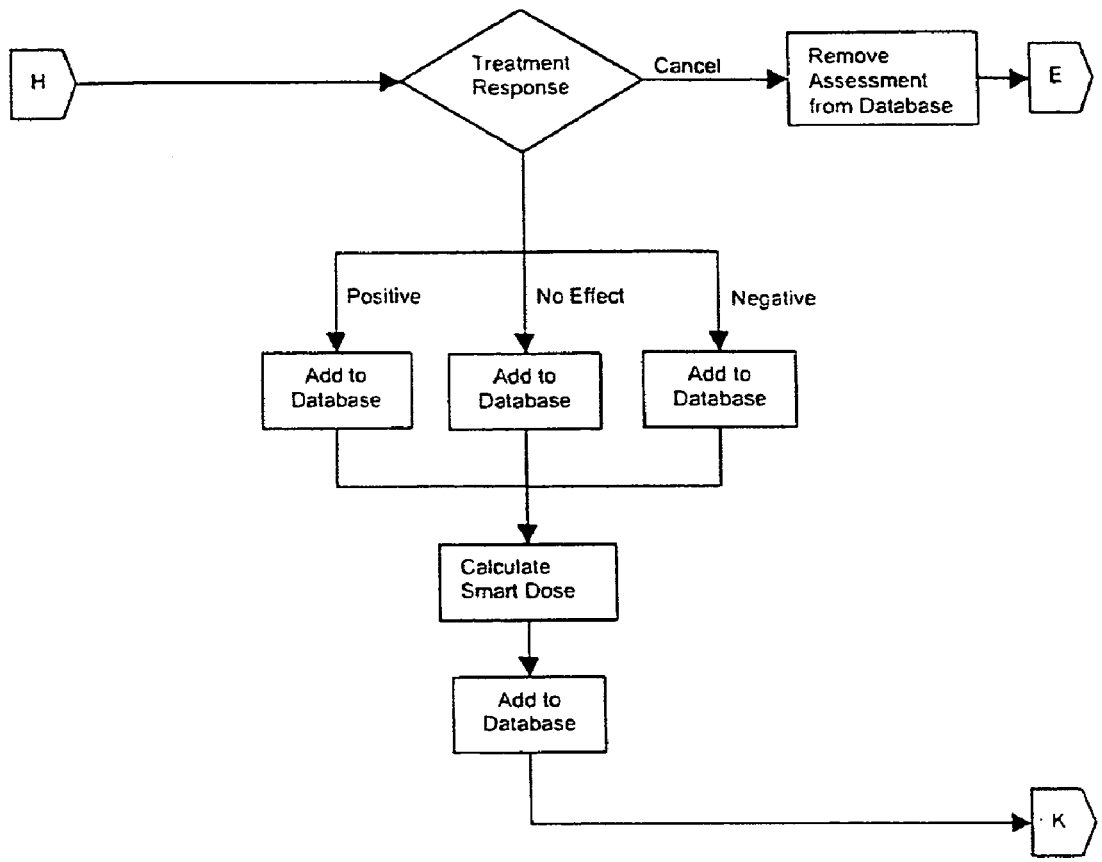
Figure 27F:
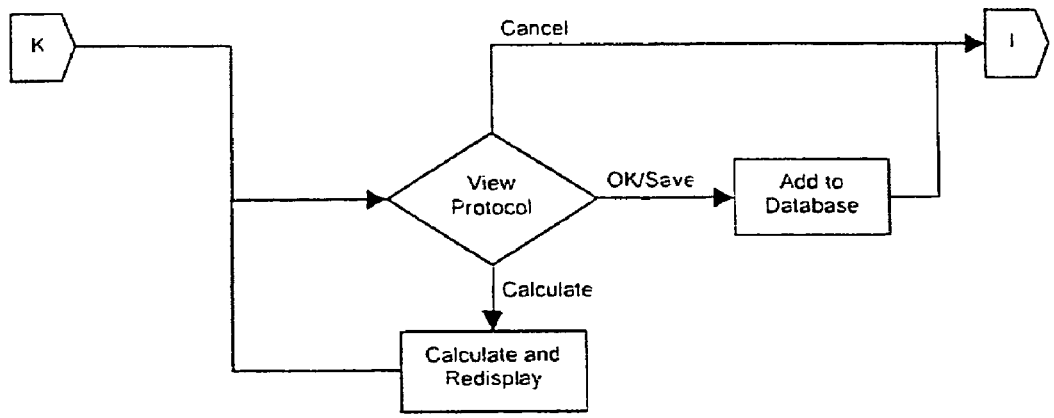
Figure 27G:
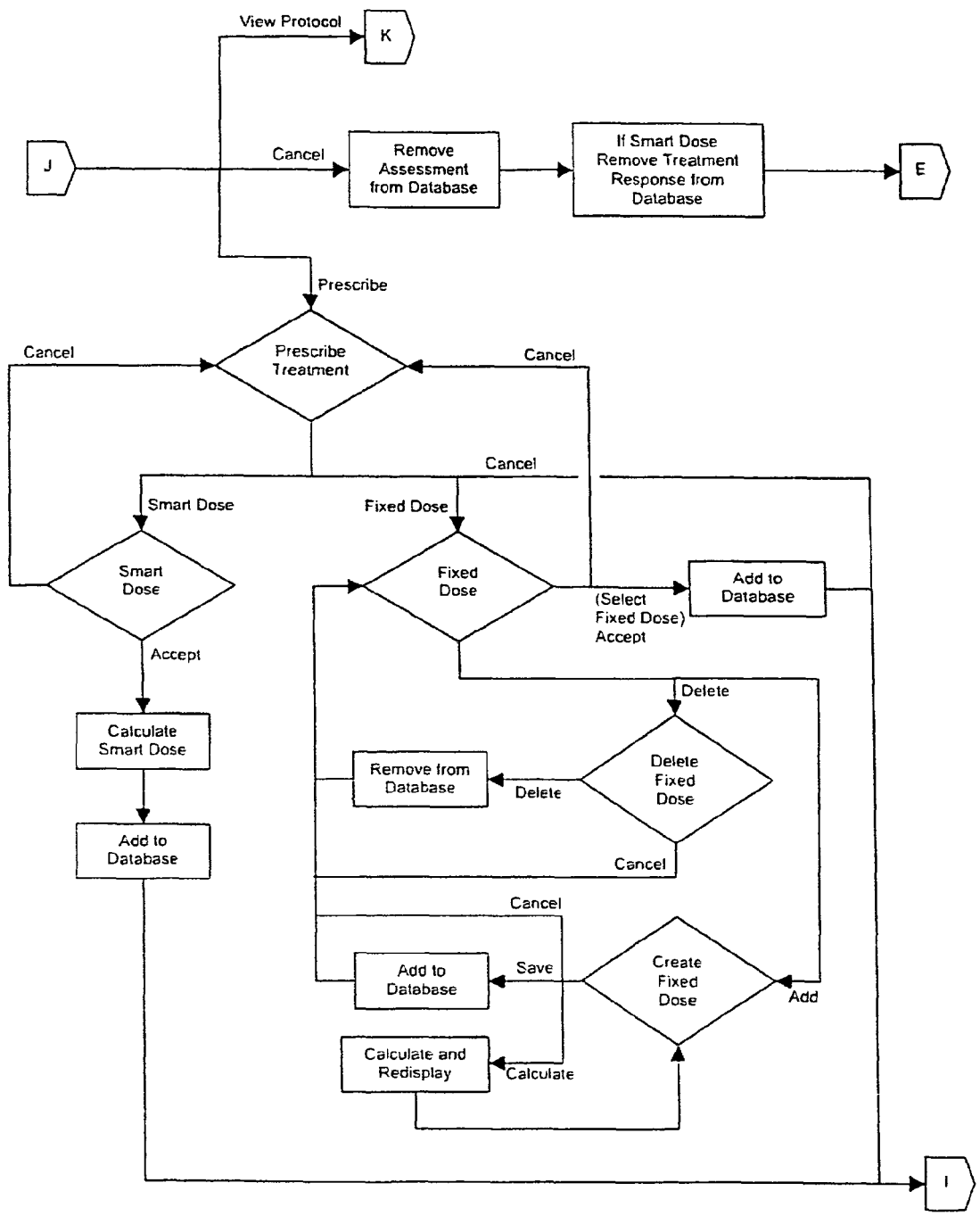

Referring to FIG. 23, the controller module 2200 user interface shown generally by numeral 2204 contains a number of LED indicators, ports (sockets) for treatment modules 200 and treatment pointers 1900, a digital display, a number of switches and a buzzer 2508 as shown in FIG. 25. In this example 8 module ports 2302 are available for treatment modules and one pointer port 2304 for a treatment pointer. Each port has a corresponding indictor to illustrate the status of that port, module port indicator 2306 for module ports and pointer port indicator 2308 for pointer ports. All switches are momentary push button types. A select switch 2310 allows the user to perform a number of functions including the ability to select from a number of preset treatment protocols stored locally. There is also a start switch 2312 and stop switch 2314 to run treatments. The display 2316 contains two LED 7 segment displays 2318 of large size in order to be viewed from a distance. LED colons are provided on either side of the two 7 segment displays 2318 which allows the digits to display either minutes or seconds, the minutes colon 2320 and the seconds colon 2322. A number of other indicators are used such as power indicator 2324, active indicator 2326, red indicator 2328, and communications status with PDA including PDA indicator 2330 and data indicator 2332. Power to the unit can be tuned on and off via a key switch 2334, the key for which can only be removed when in the off position. As well as time, the display 2316 can also show preset treatment protocols via a combination of letters and numbers, for example P0 through P9, and PDA treatment protocols such as A for LED array (treatment module) and L for laser (treatment pointer).

The sequence of operation of the controller module 2200 is as follows. Connect the power supply to the controller module power jack 2208. Turn the key 2334 to on to power up the controller module. Select a preset treatment protocol by pressing the select switch 2310 repeatedly, cycling through the preset treatment protocols from P0 to P9 until the desired preset treatment protocol P0-P9 is reached. If the preset treatment protocol uses treatment modules 200, the corresponding module port indicator(s) 2306 will flash. If the preset treatment protocol uses a treatment pointer 1900, the corresponding pointer port indicator 2308 will flash. In the case of treatment modules, plug in the desired number of treatment modules required for treatment, any number between 1 and 8, in any module port 2302. Press start switch 2312, the controller module will activate all module ports, which turns on the LED array of the treatment module(s), performs a diagnostic test on each individual port, and then deactivates all module ports. Only module ports that pass the test will be used for the treatment and each associated module port indicator will glow solid, other module port indicators will go off. Note that if a treatment module is not plugged in a module port or is defective it will not pass the test and the module port will remain inactive until the next test. Press the start switch 2312 again and the treatment will be active as per the preset treatment protocol. An "emission delay" of predefined time such as two seconds will set all indicators as active, (controller 2326 and treatment modules 212) prior to commencing treatment and activation of LED array emission. The time is shown on the display 2316 and counts down using the following sequence; for any time greater than one minute, minutes are displayed, for any time less than one minute, seconds are displayed. The active treatment indicator flashes when the treatment is active. The treatment may be stopped/paused at any time by pressing the stop button. Pressing start continues the treatment. The treatment stops automatically when the timer reaches zero, however, the user may run the preset treatment protocol as many times as desired by pressing start again. Press select switch 2310 to complete treatment and return to select preset treatment protocol. Note that if the preset treatment protocol calls for a red treatment module, the red indicator 2328 will glow. If the preset treatment protocol users the treatment pointer 1900, plug in the treatment pointer to the pointer port 2304. Note that the port sockets are physically different for treatment modules and treatment pointers. Press the start switch 2312, the treatment pointer will power up, the corresponding pointer port indicator 2308 glows solid. Direct the treatment pointers' nose cone sensor 1902 against the skin of the desired target and the treatment will be active, the timer will count down and the active indicator 2326 will flash. If the treatment pointer does not pass the self test (performed in the pointer module itself the treatment will not proceed. The treatment may be paused or stopped by simply removing the nose cone sensor away from the skin or by pressing the stop switch 2314. The treatment stops when the counter reaches zero and may be repeated as many times as necessary. When the treatment is complete, pressing the select switch 2310 shuts off power to the treatment pointer and results in a return to a select preset treatment protocol. The buzzer 2508 beeps briefly with each switch press and will beep for an extended period when the timer reaches zero.

If a treatment protocol is sent from the PDA user interface 2600 the controller module will go into PDA mode, the PDA indicator 2330 will glow, and the controller module will only run the PDA treatment protocol (preset treatment protocols will be unavailable). The PDA treatment protocol may contain either of a treatment module (array) protocol, a treatment pointer (laser) protocol or both, indicated on the display 2316 as an A (for array) or L (for laser) respectively. The user can select between the two using the select switch 2310. The sequence of operation to run a PDA treatment protocol is as described for the preset treatment protocol. The user may run as many of each of the two protocols (array protocol, laser protocol) as desired. The actual total time each of the laser and array treatments was run is stored independently in memory. Once completed, the PDA user interface will request completed treatment info including actual total time and will update patient treatment information accordingly.

Referring to FIG. 25, a schematic block diagram of the associated electronic circuitry of the controller module 2200 is shown generally by numeral 2500. The core of the controller module system is a single chip microprocessor, processor 2502. A pseudo data bus 2504 has been created in order to control a number of octal latches 2506. Octal latches 2506 are used to control the seven segment displays 2318, the indicators 2306, 2308, 2320, 2322, 2324, 2326, 2328, 2330 and 2332 and the buzzer 2508. Octal latches 2506 are also used to control the individual fan driver 2510 and the constant current source 2512. Each module port 2302 is controlled by an individual constant current source 2512 and individual fan driver 2510. Each constant current source can be individually adjusted to the desired drive current. When the treatment module 200 is connected to the module port 2302, the constant current source 2512 connects via A 2546 to the LED array control A 706, the fan driver 2510 connects via B 2548 to the fan circuit B 708 and V 2544 connects to V 704. The output enable 2514 of the octal latch used to control the constant current sources is driven by the modulation signal, mod. 2516. This allows the pre-selected group of treatment modules (ones which pass the diagnostic test) to be modulated by the modulation waveform together. Additional memory is provided using an EEPROM 2518 and the IIC data bus 2520 providing storage of relevant data even during power off.

A communication interface provides communication between a PDA and the controller module. In operation, the controller module receives operating information from the PDA, which information is processed by the controller module 2200 to control the properties of the photon emitter, such as the LED, and to thereby administer the photon therapy to the patient. The communication interface can include at least one of an electromagnetic wave interface and a physical connector. For example, communications between the PDA 2210 and controller module 2200 can occur via either the IR port 2212 or electrical interface port 2524. The electrical interface port 2524 supports either RS-232 or USB communication standards. The electrical interface port can also support charging by the controller module of the internal batteries of the PDA. The electrical interface port 2524 is supported by chipsets including RS-232/USB drivers (comm. chipset 2522). The IR port 2212 is supported by IR encoders/decoders/protocol stack handlers (IR chipset 2526) and an IR transceiver module (IR transceiver 2528). The IR port or the electrical interface port and associated cabling, and associated communications protocols form the basis of the communications interface 108-124 and 126 of FIG. 1(*d*). Three switch inputs, or switches, are provided to the processor: select switch 2310, start switch 2312 and stop switch 2314. Control signals are provided to the pointer port 2304, laser on 2530 and enable laser 2532. A power control 2534 circuit is used to turn the power on and off to the pointer port 2304 via V+ 2552 and is controlled by laser power 2536. When the treatment pointer 1900 is connected to the pointer port 2304, the power V+ 2552 connects to the V+ 2136, V− 2550 connects to V− 2134, laser on 2530 connects to laser on 2138 and enable laser 2532 connects to enable laser 2140. Power required by the controller module 2200 is a low 12 V DC voltage (Vin− Vin+ from power jack 2208) supplied by an external independent power supply. A key lock (key 2334) turns the controller module power on and off. A voltage regulator (Vreg 2538) supplies a low voltage (5 V) for logic circuitry.

Referring to FIG. 7 the diagnostic test for each treatment module 200 is performed by monitoring the total voltage drop across the LED 202 array and balancing resistors 414, from V 704 to A 706. These points are represented in the controller module by V 2544 and Vmon 2540. This voltage drop is carefully set by the balancing resistors to be a specific value and can be set to be unique for each type (red or infrared) of treatment module. A number of possible fault conditions can be identified should the specific voltage differ from the norm including total failure due to broken circuits or cables, failure of an individual diode resulting in the loss of a string of LEDs. Also, deviation in optical power output can be determined as it is proportional to total current; any variation in forward current will alter the forward voltage drop and can therefore be detected. Thus the controller module 2200, referring to FIG. 25, by monitoring a single voltage point, Vmon 2540, can ensure the individual treatment module is fully functional and its' output is within a predefined operating range. Eight individual analog to digital converters AD1-ADn 2542 are located in the processor 2502 to monitor the operation of 8 treatment modules simultaneously. Preset upper and lower values are used to determine whether the output of the analog to digital converters is within range identifying the treatment module as fully functional and at the correct operating level. This diagnostic method also has the ability to identify types (red or infrared) of treatment modules, and may be used to inhibit operation if the correct treatment module specified by the treatment protocol is not used. This method also enables the system to determine the absence of treatment modules from individual module ports. The preset upper and lower limits may be reprogrammed by the PDA user interface 2600 allowing users to fine tune the diagnostic algorithms in the field.

The processor 2502 is responsible for implementing the sequence of operation, running treatment protocols, memory management, communications and the generation of protocol waveforms. Treatment protocols supported include CW (continuous wave), and square wave modulation with duty cycles of 0 to 100% in predefined steps such as 10% and frequencies in the range of 1-10,000 Hz. Protocols are generated by a combination of the internal Pulse Width Modulator (for higher frequencies) and software algorithms (for lower frequencies). Time is in the range of 0-99 minutes. A dedicated communications protocol has been developed in order to upload and download data between the controller module and PDA user interface. The information included in this protocol includes patients last name, patient first name, patient date of birth, a number representative of indication, a number representative of previous treatments plus one, array protocol including wavelength (red or infrared), frequency, duty cycle, time, and actual time and laser protocol including frequency, duty cycle, time and actual time.

Figure 24:
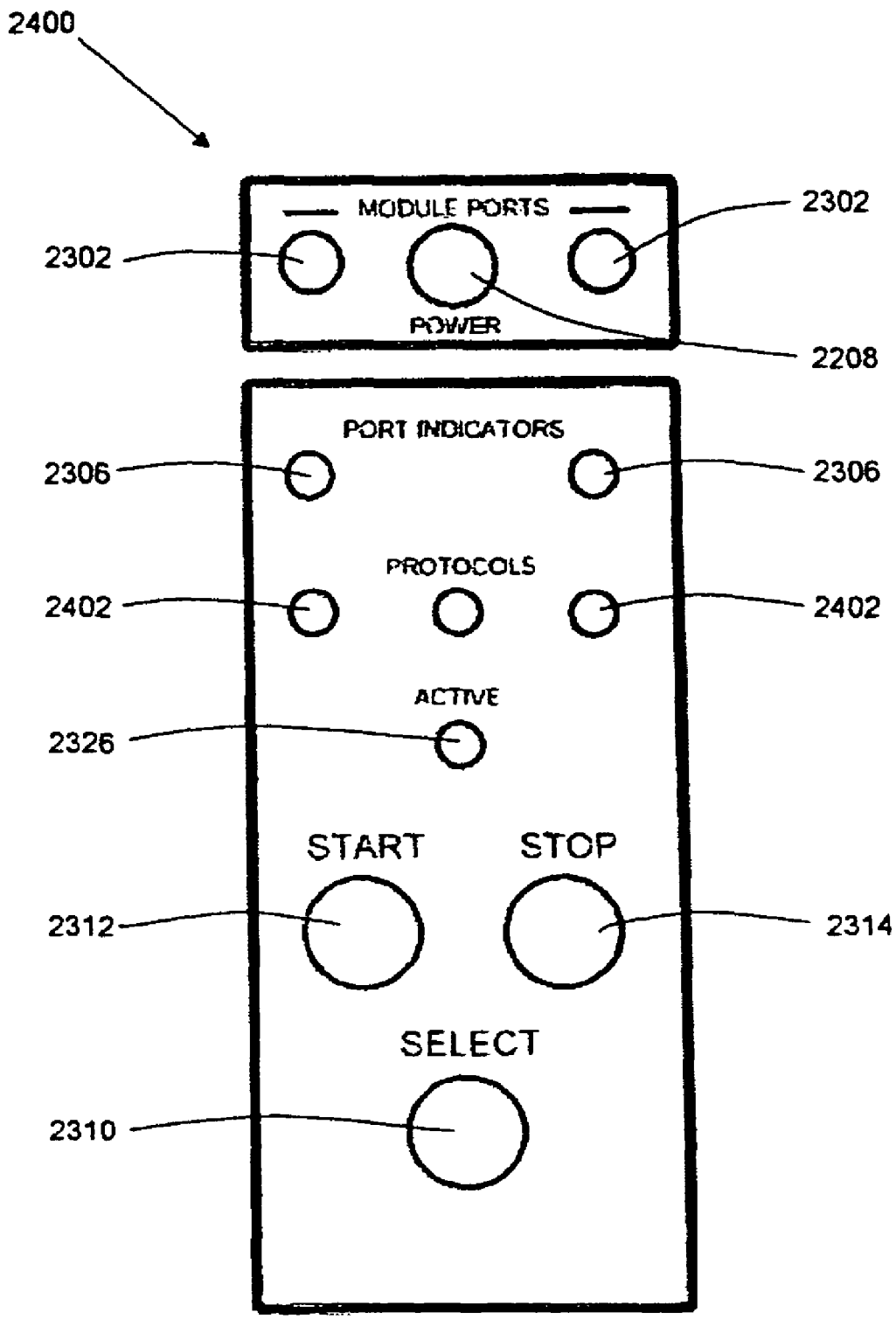
FIG. 24 shows an alternate user interface of a controller module.

Other controller modules are based on the same design as stated above with the following variations. The PDA 2210 does not dock or is not housed by the controller module, rather each are used as two independent modules. As with the above system, the PDA can communicate to the controller module via the IR port 2212 or the electrical interface port 2524 using a cable. The controller module operates totally standalone, with preset treatment protocols and therefore does not interface with a PDA. The controller module supports treatment modules 200 only or a treatment pointer 1900 only. The controller module may support only a limited number of treatment modules such as 1, 2 or 4. Thus, for example, a controller module may contain only two module ports. The controller module supports infrared or red treatment modules only. The display 2316 may be omitted. All of these variations can be used in combination to create a wide range of controller modules of varying capabilities. These simplified controller modules with reduced functionality are ideally suited for the personal use, home use and commercial markets. Referring to FIG. 24, one such simplified controller module user interface is shown generally by numeral 2400. This simplified controller module user interface could be housed in a case of similar size as a TV remote control. In the absence of the display 2316, additional LED indicators 2402 are used to indicate which preset treatment protocol (protocols) has been selected. For example, by providing 3 LED indicators 2402 the user can select between one of three preset treatment protocols, by pressing the select switch 2310 repeatedly. Other switches and indicators as well as general functionality remain the same. Thus there is a select switch 2310, a start switch 2312, a stop switch 2314, an active indicator 2326 and module port indicators 2306. Also included are a power jack 2208 and two module ports 2302, which may be located on the side of the case.

PDA User Interface

The PDA user interface 2600 is a software program designed to run on a Personal Digital Assistant (PDA) 2210, such as a Palm™ or Sony clie™, and is specifically designed to support the application of photon therapy. It provides a highly portable, simple and fast means to access large amounts of information. It is designed specifically to communicate with the controller module 2200 in order to exchange relevant protocol information and completed treatment data. The PDA user interface enables clinicians to effectively administer photon therapy with limited knowledge of the underlying protocol parameters, guiding them through the treatment processes, while clearly defining treatment parameters automatically. The PDA user interface performs a number of tasks including patient management, ailment (indication) management, records and monitors patient progress, creates and saves user defined treatment protocols and indications, contains a library of "fixed" dosage (fixed dose) treatment protocols and implements the "smart" dosage (smart dose) interactive protocol generator.

Referring to FIGS. 26(*a*)-(*t*) an embodiment of a PDA user interface is shown generally by numeral 2600. The screens shown in FIGS. 26(*a*)-(*t*) are a representation of the PDA user interface and do not depict all screens, functions and underlying support structures. The PDA user interface is arranged into numerous screens each of which performs a specific function. As the amount of data and information is limited by the small size of the screen, numerous screens are provided, breaking up tasks into specific groups. The user is guided through the process of administering photon therapy and enters data by responding to the available options presented on each screen. This is accomplished by tapping the various software buttons and arrows with a stylus. Data entry, such as patients name and date of birth, may be accomplished using either the graffiti writing area or the onscreen keyboard. Thus the PDA user interface utilizes standard techniques incorporated within the PDA operating system.

A flow chart FIGS. 27(a)-(g) is shown to illustrate how the PDA user interface is organized, functions and based on specific user entries how one moves from screen to screen. Also shown in the flow chart are background actions such as communications and database functions. Flow chart 'decision' elements are used to represent individual screens, available selections for each screen are represented and show which screen or function will be carried out next as a result of choosing a particular selection. Thus there is a direct correlation between the screens and the individual flow chart elements.

The PDA user interface is represented by an icon 2602 on the main display 2601 of available programs. Tapping the icon runs the PDA user interface software program. The Main Menu screen 2603 allows the user to start 2605 the program, setup 2606 specific operating parameters or conditions for the PDA user interface and/or send specific calibration, preset protocols and setup parameters to the controller module. About 2607 displays information such as version information and copyright information. One feature of the software is a simulator mode which allows treatments to be run without the use of a controller module. The user can enter actual treatment times to simulate the completion of a treatment. This feature is of particular use for debugging purposes, training and demonstration purposes. One of the setup screens 2608 is shown allowing the user to turn the simulator ON 2609 or turn the simulator OFF 2610. Other setup screens include the ability to send specific parameters to the controller module 2200 which for example may include preset levels used by the processor 2502 to perform diagnostic tests.

Relevant information regarding the PDA user interface operation and clinical application is available by tapping the 'i' 2604 located on the top right of each screen. This information is screen specific, thus each screen will contain unique information. For example tapping 'i' on screen 2603 calls up info screen 2611, which contains information text 2612. Arrows 2613 are provided to allow the user to scroll page up and page down. Tapping "Done" 2614 returns the user to the previous screen.

Generally, for all screens pressing cancel 2618 will return to the previous screen while accept 2617 advances to the next screen and Delete 2619 will remove the selected item from the database, as detailed in flow chart FIGS. 27(a)-(g).

A Patients screen 2615 is provided to display a list of patients 2616 which has been entered in the data base by the user. Tapping New 2621 brings up the Patient Profile screen 2623 which allows a new patient to be entered into the database. Data for each patient includes their last name 2624, their first name 2625, entered as a text string and their date of birth 2626, which includes month, day and year, their build 2627 which is divided into three subgroups, under, normal (shown), over, and their complexion 2628, which is divided into three subgroups, light (shown), medium and dark. Pressing accept enters the new patient into the database and returns to Patients screen 2615. Patients may be deleted from the database by tapping on their name followed by tapping Delete 2619. Previously entered patient information may be edited by tapping on their name followed by tapping Edit 2620, which brings up a similar screen as the patient profile 2623. In order to update the database with previously run treatment information from the controller module 2200 tap Update 2622, the PDA 2210 will then communicate with the controller module, upload protocol information including the patients name, date of birth, a number representative of indication, a number representative of previous treatments plus one, and the actual treatment times (array and laser) followed by updating the appropriate patient record in the database. To continue, tap the desired patient from the list of patients 2616 and tap accept 2617. Note, arrow keys (not shown) similar to 2613 will become available when the list of patients exceeds a single screen, allowing the user to scroll page up and page down.

A list of indications 2630 typically treated with photon therapy is provided on indication screen 2629. Note arrow keys similar to 2613 will become available when the list of indications exceeds a single screen, allowing the user to scroll page up and page down. Tapping Add 2631 brings up the Add Indications screen 2632 allowing the user to add to the database a new indication by entering a text string 2633. Two independent sets of indications may be maintained in the database, ones which cannot be deleted by the user from the database and are supplied with the software and ones which are created by the user and may be deleted.

The treatment matrix screen 2634 is patient specific, thus displaying the previously selected (active) patient 2635 and their date of birth 2636 at the top of the screen. The PDA user interface will maintain multiple indications for a given patient, thus the patient may have carpal tunnel syndrome and arthritis. These are display as Indication number of total number 2637. Arrow keys 2638 are made available when the number of indications is greater than 1, allowing the user to select a given indication. Each of the indications is managed independently. For each indication a name is provided to identify the indication 2639, a status is provided 2640 to show if an indication is new, active or discharged. The user has the ability to discharge an indication at any time by tapping Discharge 2644. A status of discharge indicates to the user that the course of treatments for that indication has been completed and no further treatments are allowed. The previous number of treatments 2641 for each indication is displayed. The protocol 2642 previously assigned for this indication is displayed, which would either be an entry from the fixed dose library or the smart dose algorithm. New indications may be added to the treatment matrix for the active patient by tapping 2643, which brings up the Indications screen 2629. A list of previously performed treatments for the active patient and indication may be viewed by tapping History 2645 which brings up the Treatments screen 2691. To continue, select the desired indication 2637 and tap accept.

For each patient and indication, and prior to each treatment, the option is available to record the patient's progress via the Record Assessment screen 2664. A number of relevant indicators may be presented such as pain 2665, dysfunction 2666 and quality of life 2667. Each of these parameters may be rated by the patient on, for example, a scale of 1-10 and the response entered by the user and stored in the database. Definitions for these indicators are defined in the info screens, along with appropriately worded questions for the user in order to query the patient with consistent definitions. The user may also view the patients' previous (past) responses to these indicators by using the arrow keys 2668 (made available when data is present). Past responses 2669 are displayed chronologically, with the most recent response shown first.

By tapping the down arrow repeatedly, previous responses are shown set by set in reverse order. Tapping the up arrow repeatedly, responses are shown chronologically. Arrows appear and disappear as required when the end of the record is reached, for example, when the first entry is reached, the down arrow disappears. When the last entry appears, the up arrow disappears. The past responses record includes a blank set of data for the current assessment, used as a marker to indicate to the user a known position within the set of data. The user has the option of bypassing the assessment by tapping Skip 2670, skipped data will be entered into the database and displayed as an 'x'.

The Treatment screen-2682 allows the user to prescribe a new treatment protocol (if not already prescribed), view the details of the protocol and run the treatment for an active patient 2635 and active indication 2647. Once prescribed the protocol is displayed as the active protocol 2683. The active protocol will be either an entry from the fixed dose library or the smart dose algorithm. Thus as the user moves through the PDA user interface a list is built and displayed at the top of each screen summarizing the active patient 2635, their date of birth 2636, the active indication 2647 and the active protocol 2683. Tapping Prescribe Treatment 2684 brings you to the Prescribe Treatment screen 2646. Tapping View Protocol 2685 brings you to the View Protocol screen 2687. Tapping Run Treatment 2686 translates the treatment protocol to processor 2502 specific parameters, builds a data string including patients last name, patient first name, patient date of birth, a number representative of indication, a number representative of previous treatments plus one, array protocol including wavelength (red or infrared), frequency, duty cycle, time, and actual time and laser protocol including frequency, duty cycle, time and actual time. Note that time and actual time are downloaded and uploaded to maintain the data string at the same size and order of parameters, simplifying data string interpretation. Actual time will be downloaded as zeros, and uploaded upon completion of treatment with stored time values representing the actual time of treatment. Refer to Update 2622 for details of uploading data. Once the data string has been sent to the controller module 2200 the results of the download are displayed to the user. For example, upon successful transmission of data, message screen 2698 is displayed. Pressing OK 2690 returns to the Patients screen 2615.

The actual numbers used by the processor 2502 of the controller module 2200 to implement the frequency 2658 and duty cycle 2659 of the modulation waveform are software and hardware dependant. They are software dependant for lower frequencies as the modulation waveform is generated by the code itself while for higher frequencies the modulation waveform is generated by the internal Pulse Width Modulator. For example, for frequencies in the range of 1-1250 Hz, frequency number=(1/protocol frequency)*50,000 duty cycle number=frequency number*protocol duty cycle/100

For higher frequencies equations are derived from the manufacturer of the processor 2502. For example, for frequencies in the range of 4881-10,000, frequency number=[(1.25*10E6/protocol frequency]−1 duty cycle number=2E(resolution)*protocol duty cycle/100 resolution=Log[5*10E6/protocol frequency]/Log2

It is far easier for the PDA 2210 to perform these calculations than the processor 2502 since it has higher processing power, more memory and the software is written using a high level language. Thus the PDA user interface 2600, translates the protocol by determining which set of calculations should be used for specific frequency range and performs the necessary calculations. Thus, when sending protocol parameters to the controller module, the parameters are in a format suitable to the processor.

When a treatment is 'run', treatment protocol information is sent to the controller module 2200 at which time the user performs the treatment by applying the appropriate treatment head(s), either treatment modules 200 and/or treatment pointer 1900, implements the treatment using the user interface 2204 of the controller module 2200. Once complete, the user can update 2622 the patients' record which includes the actual time of treatment (both array 2655 and laser 2656) into the PDA user interface 2600 data base. The PDA user interface structure is setup in such a way that a single PDA 2210 can send out treatment protocols to a number of controller modules, allowing a clinician to treat a number of patients at the same time. Data transfer includes information about the patient, (last name 2624, first name 2625 and date of birth 2626), and a number representative of indication 2637, a number representative of previous treatments 2641 plus one. Thus each treatment protocol is uniquely identifiable and the PDA user interface can update the data base with completed treatment details at the users' convenience. The PDA user interface and communications protocol ensures that outstanding data is not lost.

The View Protocol screen 2687 allows the user to view the details of the active protocol. Included is the protocol name 2654, which will either be an entry from the fixed dose library or the smart dose algorithm and all of the parameters associated with the active treatment protocol. The protocol is composed of two separate sets of parameters, array protocol 2655 (for treatment modules 200) and laser protocol 2656 (for treatment pointer 1900). For the array protocol only, the wavelength 2657 is shown either IR (infrared) or red. For both the array and laser protocol the following parameters are displayed, Frequency 2658, Duty Cycle 2659, Time 2660 and Energy Density 2661. Frequency and Duty Cycle define the modulation waveform used to control the photon emitter (LED or Laser Diode) and is a square wave in the range of 1-10,000 Hz, 0-100% duty cycle in 10% increments. The time represents the treatment time of treatment. The energy density is provided as a typical measure of delivered dosage. Note that in order to select a CW (continuous wave) protocol, the duty cycle is set to 100% and frequency will not be displayed. Note that a time of zero 2688 is used to represent the fact that the array or laser (as is shown in this case) is not used for that particular protocol. Note that the energy density is calculated by the PDA user interface based on the following calculation: the power density (in Watts per centimeter squared) of the treatment head (currently hard coded as 0.020 W/cm$^2$ for red LED array, 0.040 W/cm$^2$ for IR LED array, and 1.0 W/cm$^2$ for the laser) multiplied by the time (in seconds) multiplied by the duty cycle (in percent) divided by 100. Referring to FIG. 26(*q*) the calculation for Array 2655 is as follows: 0.040× ((12×60)+30)×80/100=24.0 Wsec/cm$^2$=24.0 J/cm$^2$. The user has the ability to edit the active protocol by changing any of the parameters wavelength 2657, frequency 2658, duty cycle 2659 and one of time 2660 or energy density 2661. Tapping Calculate 2662 will recalculate the other one of time or energy density. Should a protocol be edited by the user, a Save button 2663 will appear, tapping Save will update the database with the new protocol.

The Prescribe Treatment screen 2646 allows the user to select the type of protocol used for treatment. Tapping Fixed Dose 2649 brings you to screen Fixed Dose 2650. Tapping Smart Dose 2648 brings you to the Smart Dose screen 2671.

The Fixed Dose screen 2650 allows the user to select a fixed dose protocol from a list of protocols 2651. Note arrow keys similar to 2613 will become available when the list of fixed dose protocols exceeds a single screen, allowing the user to scroll page up and page down. Tapping Add 2652 brings up the Create Fixed Dose screen 2653 allowing the user to add to the database a new fixed dose protocol. Two independent sets of fixed dose protocols may be maintained in the database, ones which cannot be deleted by the user from the database and are supplied with the software and ones which are created by the user and may be deleted. To continue, tap the desired fixed dose protocol from the list of protocols 2651 and tap accept.

The Create Fixed Dose screen 2653 allows the user to create and save to the database a new fixed dose protocol 2651. A Protocol Name may be entered as a text string 2654 followed by parameters associated with the treatment protocol. The treatment protocol is composed of two separate sets of parameters, array protocol 2655 (for treatment modules 200) and laser protocol 2656 (for treatment pointer 1900). For the array protocol only, select the desired wavelength 2657, which is either of two categories, IR (infrared) (shown) or red. For both the array and laser protocol enter desired parameters as follows, Frequency 2658, Duty Cycle 2659, and either Time 2660 or Energy Density 2661. Frequency and Duty Cycle define the modulation waveform used to control the photon emitter (Array or Laser) and is a square wave in the range of 1-10,000 Hz, 0-100% duty cycle in 10% increments. The time entered in minutes and seconds represents the time of treatment and can range from 0-99 minutes. The energy density is provided as a typical measure of delivered dosage. If the user enters time the energy density will be calculated by the PDA user interface. If the user enters the energy density, the time will be calculated. The PDA user interface will not permit both values to entered. Once the user has entered the desired parameters tapping Calculate 2662 will check all data values for validity and calculate one of time or energy density for each of Array and Laser. Once complete tapping Save 2663 will store the fixed dose protocol in the data base and return to Fixed Dose screen 2650. In order to select a CW (continuous wave) protocol, the duty cycle will be set to 100% and frequency will not be displayed. A time of zero is used to represent the fact that the array or laser (as shown for laser 2656 by 0:00 2688) is not used for that particular protocol.

The Smart Dose screen 2671 allows the user to enter relevant clinical information regarding the active patient 2635 and active indication 2647 which will be used by the algorithm of Smart Dose 2800 to calculate an appropriate treatment protocol. Data fields include the wavelength 2672, either Infrared (shown) or Red, the type 2673 of indication, divided into four types, Musculoskeletal (shown), Neurological, Wounds, Acupuncture, the desired strategy 2674, divided into three subgroups, Array only (shown), Laser only, Array and Laser, the degree of Chronicity 2675, divided into three subgroups, Acute (shown), Sub-acute and Chronic, the Tissue 2676 type, divided into four subgroups, Tendon (shown), Ligament, Muscle, Joint, and depth to the Target 2677, divided into three subgroups, Superficial (shown), Medium and Deep. Once complete tap accept, the PDA user interface will implement the smart dose algorithm and calculate the treatment protocol, save it in the data base and return to the Treatment screen 2682.

When the active protocol 2647 is a Smart Dose protocol and the previous treatments 2641 is greater than zero a Treatment Response screen 2678 is presented to the user prior to the Treatment Screen 2682. This screen allows the user to assess the patients' response to the previous treatment, divided into three subgroups, positive 2679, no effect 2680 or negative 2681. Upon selecting one of the three types, the PDA user interface will implement the smart dose algorithm and calculate the treatment protocol, save it in the data base and continue to the Treatment screen 2682.

The Treatments screen 2691 displays a list of previously completed treatments 2692 for the active patient 2635 and active indication 2647. The list of previously completed treatments includes the date and time of treatment and the actual energy density 2661 delivered for each of array 2655 and laser 2656. To view the previously completed treatment protocol details tap on the desired previously completed treatment and tap View 2693 which brings you to the screen Treatment Detail 2694.

The Treatment Detail screen 2694 allows the user to view the specific protocol details of a previously completed treatment. This includes the protocol name 2654 and the treatment protocol including the same set of parameters as View Protocol 2687. The time 2695 represents the actual treatment time of the previously delivered treatment and the resultant energy density 2696.

Smart Dose

The smart dosage (Smart Dose) interactive protocol generator creates treatment protocols based on an algorithm which is dynamic, and based on a number of relevant clinical indicators resulting in treatments that are specific to each individual, a particular ailment and their individual rate of recovery.

Relevant clinical indicators include an individual's physical characteristics, ailment specific parameters and recovery specific parameters. Other clinical indicators may be used. Physical characteristics can include age, complexion and build or other measures such as general health. Ailment specific parameters can include the type of tissue to be treated, the degree of chronicity and the depth to the target site. Recovery specific parameters may include a patient's response to previous treatments or other measures such as the degree of pain and range of motion. Relevant clinical indicators are clinical indicators that are relevant to the type of ailment the patient has or is trying to prevent. For example, types of ailment can include musculoskeletal, wound or neurological, for which the set of relevant clinical indicators may differ as required.

While in one embodiment, the algorithm of Smart Dose 2800 is embedded within the PDA user interface 2600, it could be used as a standalone entity and is not system (hardware or software) dependant and is not dependant on the photon therapy system used. Thus, in simple terms the algorithm of Smart Dose 2800 inputs relevant clinical data and outputs treatment protocols.

In one embodiment, each type of ailment is associated with a base protocol, although the association need not be one-to-one (two types of ailments may be associated with the same base protocol, for example). A protocol is a set of data that specifies the controllable properties of the treatment modules exhibited during the photon therapy. Treatment protocols include but are not limited to the wavelength of photon energy, generally fixed by the specific treatment head, a pulsing of the photon emission (turning the emission on and off at predetermined rates) generally defined by a frequency and duty cycle, the length of time of treatment and the energy density which is to some degree a summary of the total dosage as it includes the power of the source, the spot size or surface area of the source, the length of time of the treatment and the duty cycle.

As described in more detail below, a clinical indicator is associated with one or more modifying factors that act on the base protocol to yield a modified protocol. The clinical indicators are input by the user of the Smart Dose system to tailor the photon therapy to the patient. Compared to a traditional library of preset 'fixed protocols,' the algorithm of Smart Dose 2800 is dynamic, changing treatment protocol parameters with every patient, ailment and treatment based on a number of input criteria, and is interactive as it acquires feedback from the patient.

Figure 28A:
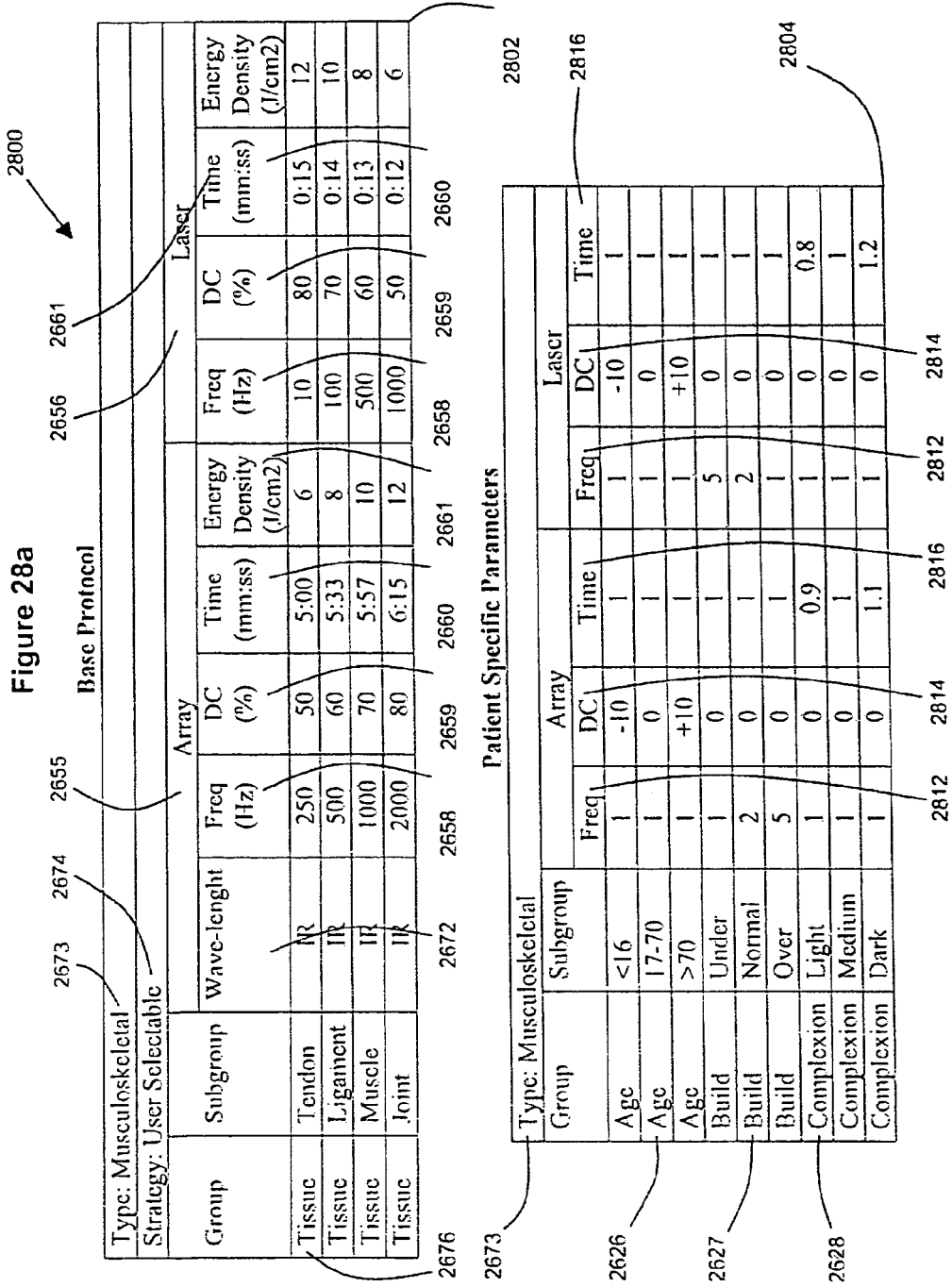

Referring to FIGS. 28(a)-(b), the smart dose algorithm is based on a number of main elements; these include the base protocol 2802, patient specific parameters 2804, ailment specific parameters 2806, recovery specific parameters 2808 and absolute limits 2810. The smart dose algorithm acquires its input data from the PDA user interface 2600. Thus, there is a direct correlation of parameters between the two entities. The smart dose algorithm outputs its treatment protocol parameters to the PDA user interface. Thus, there is a direct correlation of parameters between the two entities.

Referring to the Base Protocol 2802 a set of treatment protocols are based on the tissue type of the ailment. The tissue type 2676 is divided into four subgroups tendon, ligament, muscle and joint. Each of these subgroups contains a set of treatment protocol parameters. The treatment protocols are subdivided into two sets, one for array 2655 (treatment modules 200) and one for laser 2656 (treatment pointer 1900). For the array parameters include the wavelength 2672 (either red or infrared), the frequency 2658, the duty cycle 2659, the time 2660 and the energy density 2661. For the laser parameters include the frequency 2658, the duty cycle 2659, the time 2660 and the energy density 2661. Selecting a specific tissue subgroup loads a set of treatment protocols, the 'base' protocol, into the smart dose algorithm.

For some elements of the smart dose algorithm the user may select the desired result, rather than it being determined automatically by the smart dose algorithm. This is the case for the strategy 2674, which is divided into three subgroups, array only, laser only and array and laser. Since the strategy is user selectable, the user has the ability to select one of the three subgroups. Thus even though treatment protocols exist for both the array and laser, if the user selects for example laser only, then the array treatment protocols will be ignored. This ability is particularly useful for musculoskeletal conditions, allowing the user to choose their preferred treatment strategy. In other cases, using wound healing as an example, the smart dose algorithm may force the user to use the array only. A number of sets of base protocols are available based on the type 2673 of ailment that is being treated, thus there are four types of ailments, Musculoskeletal, Neurological, Wounds and Acupuncture. Thus for each type the entire table 2802 would have independent sets of base protocols. This holds true for all parameters associated with the smart dose algorithm, thus patient specific parameters 2804, ailment specific parameters 2806, recovery specific parameters 2808 and absolute limits 2810 are all specific for type 2673 musculoskeletal. For each type of ailment, a complete set of data is available, allowing a separate smart dose algorithm to be created.

Referring to the Patient Specific Parameters 2804 a set of scale or modifying factors are based on the age, build and complexion of the patient. The age 2626 is divided into three subgroups under 16, 17-70 and over 70 years of age. Based on the date of birth of the patient the appropriate age subgroup is determined by the PDA user interface. The build 2627 subgroup is divided into three subgroups, under, normal and over, referring to the weight of the patient. The complexion 2628 is divided into three subgroups, light, medium and dark. Each of these subgroups contains a set of scale or modifying factors. There are three scale factors, frequency 2812, duty cycle 2814 and time 2816. The numerical operator for frequency and duty cycle is multiplication and for duty cycle is addition. A scale factor of 1 for frequency and time, and a scale factor of 0 for duty cycle, will be neutral, have no effect on the treatment protocol. The scale factors are subdivided into two sets, one for array 2655 (treatment modules 200) and one for laser 2656 (treatment pointer 1900). The treatment parameters of the base protocol 2802 are scaled by the scale factors by performing the associated numerical operator of the patient specific parameters 2804 for each of frequency, duty cycle and time for each of array and laser based on the subgroups chosen by the user. Examples of calculations are as follows, for frequency a base protocol of 500, a scale factor of 2, the numerical operator is multiplication, and the resultant frequency is 500×2=1000. For a duty cycle base protocol of 70, a scale factor of −10, the numerical operator is addition, the resultant duty cycle is 70+(−10)=60. For time a base protocol of 5:33 (5 minutes and 33 seconds), a scale factor of 0.8, the numerical operator is multiplication, the resultant time is ((5×60)+33)×0.8=266 seconds=4:26. Thus for every treatment, the treatment protocol is tailored according to the patients individual characteristics.

Referring to the Ailment Specific Parameters 2806, a set of scale factors are based on the chronicity 2675, and depth to target 2677. The chronicity 2675 is divided into three subgroups acute, subacute and chronic. The target 2677 is divided into three subgroups, superficial, medium and deep. Each of these subgroups contains a set of scale factors. There are three scale factors, frequency 2812, duty cycle 2814 and time 2816. The numerical operator for frequency and duty cycle is multiplication and for duty cycle is addition. A scale factor of 1 for frequency and time, and a scale factor of 0 for duty cycle, will be neutral, have no effect on the treatment protocol. The scale factors are subdivided into two sets, one for array 2655 (treatment modules 200) and one for laser 2656 (treatment pointer 1900). The resultant (base protocol 2802 scaled by patient specific parameters 2804) treatment protocol is scaled by the scale factors by performing the associated numerical operator of the ailment specific parameters for each of frequency, duty cycle and time for each of array and laser based on the subgroups chosen by the user. Thus for every treatment, the treatment protocol is tailored according to the patients individual ailment.

Prior to each subsequent treatment the patient is queried with regard to their previous treatment response. Referring to the Recovery Specific Parameters 2808 a set of scale factors are based on the response to previous treatment. The response is divided into three subgroups positive 2679, no effect 2680 and negative 2681. Each of these subgroups contains a set of scale factors. There are three scale factors, frequency 2812, duty cycle 2814 and time 2816. The numerical operator for frequency and duty cycle is multiplication and for duty cycle is addition. A scale factor of 1 for frequency and time, and a scale factor of 0 for duty cycle, will be neutral, have no effect on the treatment protocol. The scale factors are subdivided into two sets, one for array 2655 (treatment modules 200) and one for laser 2656 (treatment pointer 1900). The resultant (base protocol 2802 scaled by patient specific parameters 2804 and scaled by ailment specific parameters 2806) treatment protocol is scaled by the scale factors by performing the associated numerical operator of the recovery specific parameters for each of frequency, duty cycle and time for each of array and laser based on the subgroups chosen by the user. Thus for every treatment, the treatment protocol is tailored according to the patients individual rate of recovery.

In summary, a base protocol 2802 is modified by a set of user selected patient specific parameters 2804, which is then modified by a set of user selected ailment specific parameters 2806, which is then modified by a set of user selected (based on patient response) recovery specific parameters 2808 resulting in an appropriate treatment protocol.

To ensure that treatment protocols do not exceed certain predefined limits, the results of all calculations are checked with a set of absolute limits 2810. Should any values fall beyond the absolute limits the smart dose calculations will default to the absolute limits. A set of limits are available for both minimum (min 2818) and maximum (max 2820) values. A set of limits includes frequency (Freq 2822), duty cycle (DC 2824) and time (Time 2826) for each of array 2655 and laser 2856.

The values shown for base protocols 2802, patient, ailment and recovery specific parameters, 2804, 2806 and 2808 respectively and absolute limits 2810 are for illustrative purposes only and do not contain any clinical relevance. Smart Dose 2800 is not fixed; additional input groups may be added or removed, subgroups can be increased or decreased, and definitions can be altered. Also output categories may be added or removed. Smart Dose can include a methodology for administering photon therapy, as well as a specific method for carrying out same.

The values shown for base protocols 2802, patient, ailment and recovery specific parameters, 2804, 2806 and 2808 respectively can be self determined in a similar fashion as individual treatment protocols are defined for each treatment by relevant clinical indicators via smart dose. The system architecture (PDA 2210, PDA user interface 2600, Smart Dose 2800, PC software and Exporting Data) has the means of collecting and storing clinical outcomes and delivered treatment data on a treatment by treatment basis. By compiling a large body of treatment data from multiple users this data can be analyzed and used to redefine the smart dose values. For example, should the data demonstrate that a large number of musculoskeletal conditions requiring the treatment of a ligament resulted in a treatment response 2678 of negative 2681 the base protocol 2802 could be altered accordingly, reducing for example the time 2660. For example, should the data demonstrate that a large number of musculoskeletal conditions which are chronic resulted in a treatment response of no effect 2680, the ailment specific parameters could be altered accordingly, increasing for example frequency 2812 scale factor for subgroup chronic. This method can be further enhanced by adding data obtained by the record assessment 2664. For example, should the data demonstrate that a large number of patients whose build 2627 is over are not realizing a significant reduction in pain 2665, the patient specific parameters 2804 could be altered accordingly, increasing for example the duty cycle 2814 scale factor for subgroup over. Thus the system provides a means of determining the smart dose values.

In another embodiment of the present invention, all the types of ailments are associated with just one base protocol. Thus, in this embodiment, only one base protocol is used. This one base protocol may then be modified with modifying factors associated with the clinical indicators relevant to a particular type of ailment. In yet another embodiment, again only one base protocol is used, and no type of ailment is specified. In this embodiment, clinical indicators that would be relevant to one or any type of ailment could then be selected by the user to modify the base protocol.

The smart dose interactive protocol generator has been designed to address one of the major concerns facing the industry, repeatability. While demonstrating significant benefit for a wide range of individuals and a wide range of ailments, photon therapy often demonstrates little of no effect for others. This is primarily due to the fact that individual response to photon therapy differs from patient to patient and the number of ailments treated is extensive. The development of a set of preset fixed treatment protocols capable of satisfying all known requirements is daunting. The smart dose algorithm essentially takes the essence of how fixed dose protocols are created and automates the process. This in part is achieved by using known effects of specific parameters in order to alter specific parameters within a given treatment protocol. Furthermore, by obtaining feedback from the patient with regard to their response to the previous treatment, the protocol is adjusted accordingly, creating dynamic protocols and automating the thought process normally performed by the clinician. For example, chronic injuries are generally treated with higher modulation frequencies than acute conditions, deeper target sites require a longer treatment time as less of the photon energy is reaching the desired target. Darker skin will absorb more of the photon energy, leaving less energy at the target site below the skin. Elderly people respond less to photon therapy than do younger people. The target site of overweight people is more difficult to reach due to a barrier of fat tissue, thus the time of treatment should be increased. Increasing the duty cycle is an effective means of increasing the dosage without increasing the length of time of treatment. If a patient is not responding to treatment, the dosage is generally increased. Thus the smart dose algorithm provides an alternative means of administering photon therapy.

PC Software

Figure 29A:
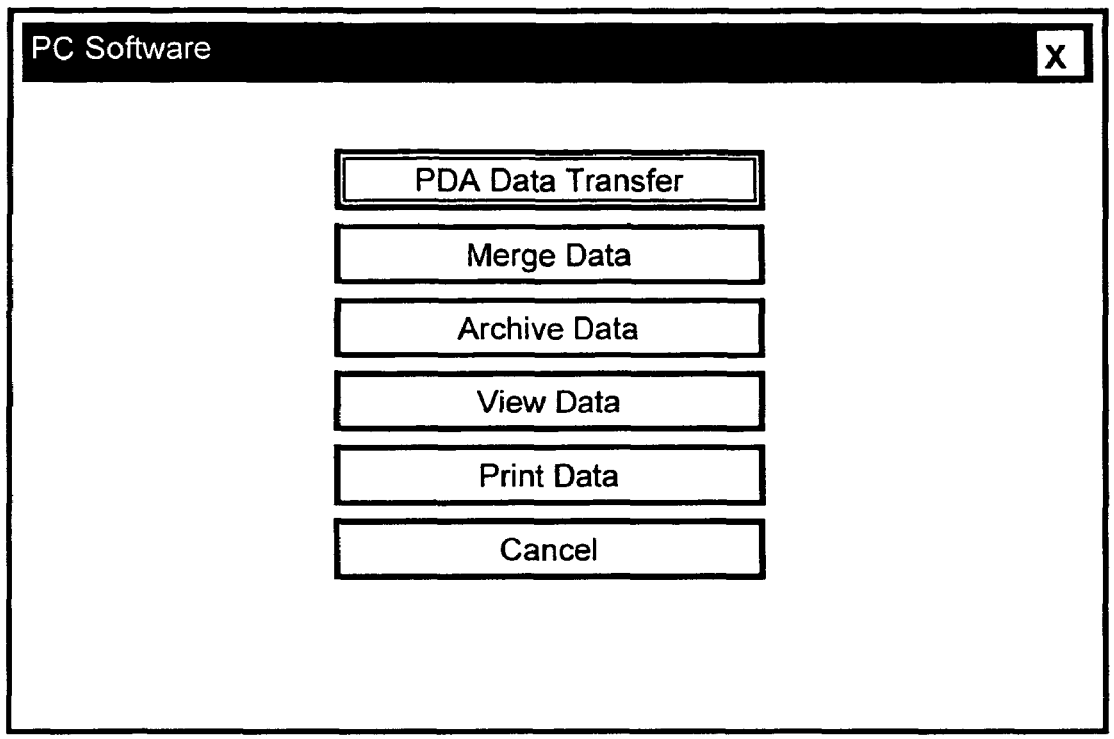

The PC software program is designed to manage data generated by the PDA user interface 2600. Data transfer is achieved using the hardware supplied by the PDA manufacturer such as a cradle or interface cable forming the basis of the communications interface 128 of FIG. 1. The actual transfer of data can be achieved using either PDA supplied software or communications software integrated within the PC software program. A number of data files are relevant to the PDA user interface and include such files as the indication database, the fixed dose treatment protocols data base, the smart dose base protocols, scale factors and absolute limits and the patient data base. Referring to FIG. 29(*a*), a representative main screen, the PC software can perform a number of functions such as PDA Data Transfer, Merge Data, Archive Data, View Data and Print Data. PDA Data Transfer facilitates the transfer of PDA user interface data files to and from the PC as a means of backing up data generated by the PDA user interface and loading the PDA user interface with updated versions of data files. Another function of the PC software is to Merge Data from a number of PDA user interfaces. If a user site is using a number of PDA user interfaces simultaneously, data entries for each of the PDA user interfaces would be unique. The software would compile all of the data from a number of PDA user interfaces and combine them into a single database. As a result all PDA user interfaces could be updated with all of the latest patient information. This would allow any number of users to treat any number of patients while maintaining data integrity. In order to free up memory space within the PDA 2210, the PC software has the ability to Archive Data. Specific patient entries, for example patients who have not had an active treatment for some time, may be removed from the current active patient data base and stored in a separate archive data base. These entries could be returned to the active database if required. View Data enables data base information obtained from the PDA user interface to be displayed via a number of screens. Another function (not shown) of the PC software is to Export Data. Data files generated by the PDA user interface can be reformatted by the PC software (using simple delimiters between data fields for example) and exported to other applications such as Microsoft Excel™ and Microsoft Access™.

Figure 29B:
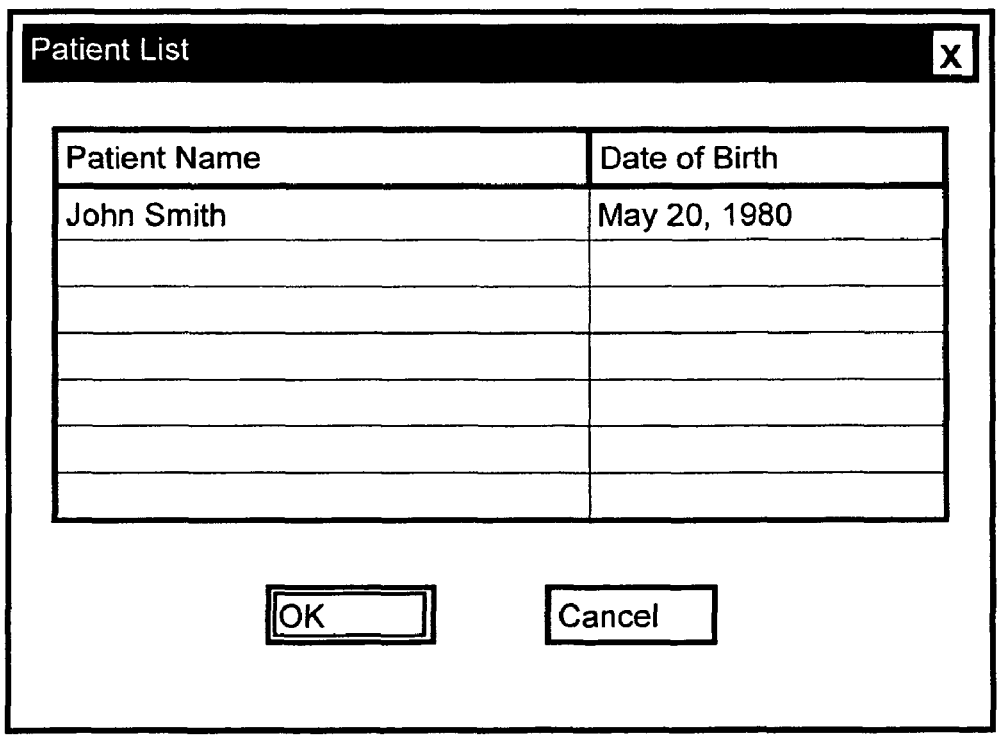

FIGS. 29(b)-(e) illustrate an example of viewing patient data. FIG. 29(b) provides a list of patients, selecting a patient from the list would bring up a list of indications (ailments) FIG. 29(c). Selecting an ailment would bring up a list of previously performed treatments FIG. 29(d). Selecting a treatment would bring up the details of that treatment FIG. 29(e). Preformatted pages containing patient information and other data base information may be sent to a printer.

In operation, a first user applies a first at least one treatment module to a first patient. The first user administers a first photon therapy to the first patient with a first PDA connected to the first at least one treatment module. First data pertaining to the first photon therapy is recorded on the first PDA, and downloaded to a PC computer or central computing device using the PC software. A second user likewise applies a second at least one treatment module to a second patient, and administers a second photon therapy to the second patient with a second personal digital assistant (PDA) connected to the second at least one treatment module. Second data pertaining to the second photon therapy is recorded on the second PDA, and downloaded from the second PDA to the central computing device. The PC or central computing device forms merged data containing at least a first portion of the first data and at least a second portion of the second data, and the central computing device sends the merged data to the first and second PDAs for updating.

Palette

In FIG. 30 a palette is shown generally by numeral 3000. In order to store and manage the use of the photon therapy system components a tray or palette is shown. The palette base 3002 contains dedicated slots/spaces for each of a number of system components. Slots may support individual elements or combine a number of elements in a single slot. Cables are oriented in the same direction and are allowed to drape over the edge of the palette, thus if the palette is aligned with the edge of a table the cables would hang freely down the side. A slot is provided 3004 for placement of the treatment pointer 1900. A slot 3006 is provided for the placement of strap assemblies 1100. A slot 3008 is provided for the placement of rails 900. A slot 3010 is provided for the placement of treatment modules 200. A slot 3012 may be available which is capable of holding a liquid such as alcohol, creating a reservoir, allowing treatment modules 200, to be cleaned prior to or after each treatment, by dipping or soaking in the slot 3012. This slot 3012 may be fed by an optional inverted storage tank 3014. The depth of the reservoir may be controlled by adding a second overflow reservoir, and a dam, allowing excess liquid to drain into the overflow, maintaining the desired depth of liquid within the cleaning reservoir. Note also that a similar palette may be created in order to house a cleaning reservoir exclusively.

It should be understood that various modifications could be made to the embodiments described and illustrated herein, without departing from the present invention, the scope of which is defined in the appended claims.

What is claimed is:

1. A system for administering photon therapy to a treatment site of a patient, the system comprising a plurality of treatment modules, each of the treatment modules including at least one photon emitter, and a case for housing the at least one photon emitter, wherein the case includes complementary first and second linkers for flexibly linking the treatment modules to form an arbitrary modular pattern to cover the treatment site, the first linker of the case being adapted to engage and disengage from the second linker of the case of another treatment module, wherein the linkers are selected from a hook and latch system and a rail assembly.

2. The system of claim 1, wherein the photon emitter includes at least one of a light emitting diode and a laser diode.

3. The system of claim 1, wherein the linkers include a hook and latch system to connect the treatment modules end-to-end.

4. The system of claim 3, wherein the hook and latch system includes latches on each case that form an integral part thereof.

5. The system of claim 3, wherein the hook and latch system includes latches and a pair of hooks on each treatment module that enable two neighboring treatment modules to rotate about a nominal axis that connects the pair of hooks.

6. The system of claim 1, wherein the linkers include a rail assembly to connect the treatment modules side-by-side.

7. The system of claim 6, wherein the rail assembly is composed of a flexible material.

8. The system of claim 6, further comprising a securing assembly adapted for securing the system to the patient.

9. The system of claim 1, wherein the case includes a protrusion capable of displacing tissue of the patient at the treatment site.

10. The system of claim 9, wherein the protrusion is a protruding cone.

11. The system of claim 1, wherein the treatment module includes a plurality of photon emitters arranged in horizontal rows, such that even numbered rows are vertically aligned and odd numbered rows are vertically aligned and offset from the even numbered rows.

12. The system of claim 1, further comprising a holder to which the plurality of treatment modules are secured at angles to direct the light produced by the photon emitters.

13. The system of claim 12, such that the holder is dish-shaped and includes a base and a rim, wherein, in operation, the rim is in contact with the patient to maintain the photon emitters above the treatment site without touching the treatment site.

14. The system of claim 12, wherein the holder is an angled bracket.

15. The system of claim 12, wherein the holder is C-channeled.

16. The system of claim 1, further comprising a positive feedback device that produces at least one of vibration and audible noise to indicate to the patient that the system is operating.

17. The system of claim 16, wherein the positive feedback device is a fan.

18. The system of claim 1, further comprising a controller module configured to perform diagnostics of the at least one photon emitter by monitoring a voltage drop.

19. The system of claim 18, further comprising at least one balancing resistor electrically coupled to the at least one photon emitter, the voltage drop resulting from a drop in voltage across the at least one photon emitter and the at least one balancing resistor.

20. The system of claim 19, wherein the value of the voltage drop is a function of the wavelength of light being emitted by the at least one photon emitter, which value can be used to selectively disable or enable at least one of the photon emitters emitting a particular wavelength.

21. The system of claim 1, further comprising a palette having a slot filled with a cleaning fluid for cleaning the at least one treatment module.

22. The system of claim 21, further comprising a storage tank connected to the slot to replenish the slot with the cleaning fluid.

23. A system for administering photon therapy to a treatment site of a patient, the system comprising a plurality of treatment modules, each of the treatment modules including at least one photon emitter, and a case for housing the at least one photon emitter, wherein the case includes complementary first and second linkers for flexibly linking the treatment modules to form an arbitrary modular pattern to cover the treatment site, the first linker of the case being adapted to engage and disengage from the second linker of the case of another treatment module, wherein the linkers are selected from a hook and latch system and a rail assembly, wherein each treatment module further includes a cooling device for cooling the treatment module.

24. The system of claim 23, wherein the cooling device includes a fan.

25. The system of claim 24, wherein the case includes a lid having an internal bracket for securing the fan.

26. The system of claim 25, wherein the internal bracket secures the fan without a screw.

27. A system for administering photon therapy to a treatment site of a patient, the system comprising a plurality of treatment modules, each of the treatment modules including at least one photon emitter, and a case for housing the at least one photon emitter, wherein the case includes complementary first and second linkers for flexibly linking the treatment modules to form an arbitrary modular pattern to cover the treatment site, the first linker of the case being adapted to engage and disengage from the second linker of the case of another treatment module, the system further comprising an adhesive that surrounds a portion of the photon emitter and that bonds the photon emitter to a base of the case, said adhesive sealing any space between the photon emitter and the base to prevent contamination and facilitate cleaning.

28. A system for administering photon therapy to a treatment site of a patient, the system comprising a plurality of treatment modules, each of the treatment modules including at least one photon emitter, and a case for housing the at least one photon emitter, wherein the case includes complementary first and second linkers for flexibly linking the treatment modules to form an arbitrary modular pattern to cover the treatment site, the first linker of the case being adapted to engage and disengage from the second linker of the case of another treatment module, the system further comprising a rail assembly for connecting a plurality of treatment modules side by side, wherein the rail assembly includes at least one slot for attaching a securing assembly adapted for securing the system to a patient.

29. The system of claim 28, wherein the at least one slot consists of a plurality of slots to provide several options for attaching the securing assembly.

30. A system for administering photon therapy to a treatment site of a patient, the system comprising a plurality of treatment modules, each of the treatment modules including at least one photon emitter, and a case for housing the at least one photon emitter, wherein the case includes complementary first and second linkers for linking the treatment modules to form an arbitrary modular pattern to cover the treatment site, the first linker of the case being adapted to engage and disengage from the second linker of the case of another treatment module, the system further comprising at least one counterweight to position the system on the treatment site, each counterweight weighing more than any one treatment module.

31. The system of claim 30, wherein each counterweight and each treatment module is approximately the same shape and size.

32. The system of claim 30, wherein each counterweight has a hook and latch system for linking with treatment modules.

* * * * *